(12) United States Patent
Stephan et al.

(10) Patent No.: US 9,750,552 B2
(45) Date of Patent: Sep. 5, 2017

(54) EXPANDABLE FIXATION ASSEMBLIES

(71) Applicant: DePuy Synthes Products, Inc., Raynham, MA (US)

(72) Inventors: Kai Stephan, Basel (CH); Bryan J. Griffiths, West Chester, PA (US); Samuel Leuenberger, Oberdorf (CH); Robert J. Schoutens, Oberdorf (CH); Marcello Memmolo, Reinach (CH); Daniela Pricope, Oberdorf (CH); Rainer Ponzer, Oberdorf (CH); Andre Schlienger, Basel (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/615,898

(22) Filed: Feb. 6, 2015

(65) Prior Publication Data
US 2015/0150612 A1 Jun. 4, 2015

Related U.S. Application Data

(62) Division of application No. 12/831,144, filed on Jul. 6, 2010, now Pat. No. 8,974,508.
(Continued)

(51) Int. Cl.
*A61F 2/44* (2006.01)
*A61B 17/84* (2006.01)
(Continued)

(52) U.S. Cl.
CPC .......... *A61B 17/844* (2013.01); *A61B 17/686* (2013.01); *A61B 17/688* (2013.01);
(Continued)

(58) Field of Classification Search
CPC ......................................... A61F 2/4455–2/447
See application file for complete search history.

(56) References Cited

U.S. PATENT DOCUMENTS

| 2,381,050 A | 8/1945 | Harding |
|---|---|---|
| 2,490,364 A | 12/1949 | Livingston |

(Continued)

FOREIGN PATENT DOCUMENTS

| CN | 101073513 A | 11/2007 |
|---|---|---|
| CN | 101909548 A | 12/2010 |

(Continued)

OTHER PUBLICATIONS

U.S. Appl. No. 61/675,975, filed Jul. 26, 2012, Lechmann et al.
(Continued)

*Primary Examiner* — David Bates
*Assistant Examiner* — Olivia C Chang
(74) *Attorney, Agent, or Firm* — Baker & Hostetler LLP

(57) ABSTRACT

Expandable fixation assemblies, expandable cranial fixation assemblies, and expandable intervertebral implant assemblies are provided for securing structures to bone and for securing bones and/or bone segments with respect to each other. An expansion member can be moved through at least a portion of an expandable fixation body, thereby causing expansion of the expandable fixation body, such that bone engagement features of the expandable fixation body engage surrounding structure, such as bone.

19 Claims, 48 Drawing Sheets

Related U.S. Application Data

(60) Provisional application No. 61/223,261, filed on Jul. 6, 2009.

(51) Int. Cl.
    *A61B 17/68*           (2006.01)
    *A61B 17/70*           (2006.01)
    *A61B 17/86*           (2006.01)

(52) U.S. Cl.
    CPC ............ *A61B 17/84* (2013.01); *A61B 17/864* (2013.01); *A61B 17/8635* (2013.01); *A61B 17/8685* (2013.01); *A61B 17/683* (2013.01); *A61B 17/7001* (2013.01); *A61B 17/7062* (2013.01); *A61B 17/863* (2013.01); *A61F 2/442* (2013.01)

(56) References Cited

U.S. PATENT DOCUMENTS

| | | |
|---|---|---|
| 2,746,385 A | 5/1956 | Muller |
| 3,867,728 A | 2/1975 | Stubstad et al. |
| 4,349,921 A | 9/1982 | Kuntz |
| 4,701,993 A | 10/1987 | Bradley et al. |
| 4,759,766 A | 7/1988 | Buettner-Janz et al. |
| 4,856,950 A | 8/1989 | Bushnell et al. |
| 4,863,476 A | 9/1989 | Shepperd |
| 5,059,193 A | 10/1991 | Kuslich |
| 5,123,926 A | 6/1992 | Pisharodi |
| 5,167,665 A | 12/1992 | McKinney et al. |
| 5,290,312 A | 3/1994 | Kojimoto et al. |
| 5,314,477 A | 5/1994 | Marnay |
| 5,344,252 A | 9/1994 | Kakimoto |
| 5,354,298 A | 10/1994 | Lee et al. |
| 5,370,697 A | 12/1994 | Baumgartner |
| 5,390,683 A | 2/1995 | Pisharodi |
| 5,401,269 A | 3/1995 | Buttner-Janz et al. |
| 5,425,773 A | 6/1995 | Boyd et al. |
| 5,443,514 A | 8/1995 | Steffee |
| 5,507,816 A | 4/1996 | Bullivant |
| 5,522,899 A | 6/1996 | Michelson |
| 5,534,029 A | 7/1996 | Shima |
| 5,554,191 A | 9/1996 | Lahille et al. |
| 5,556,431 A | 9/1996 | Buttner-Janz |
| 5,562,738 A | 10/1996 | Boyd et al. |
| 5,609,635 A | 3/1997 | Michelson |
| 5,653,763 A | 8/1997 | Errico |
| 5,658,335 A | 8/1997 | Allen |
| 5,662,658 A | 9/1997 | Wenstrom et al. |
| 5,665,122 A | 9/1997 | Kambin |
| 5,676,701 A | 10/1997 | Yuan et al. |
| 5,683,465 A | 11/1997 | Shinn et al. |
| 5,697,977 A | 12/1997 | Pisharodi |
| 5,716,415 A | 2/1998 | Steffee |
| 5,772,661 A | 6/1998 | Michelson |
| 5,782,832 A | 7/1998 | Larsen et al. |
| 5,860,973 A | 1/1999 | Michelson |
| 5,865,848 A | 2/1999 | Baker |
| 5,888,224 A | 3/1999 | Beckers et al. |
| 5,888,226 A | 3/1999 | Rogozinski |
| 5,893,889 A | 4/1999 | Harrington |
| 5,893,890 A | 4/1999 | Pisharodi |
| 5,980,522 A | 11/1999 | Koros et al. |
| 5,989,291 A | 11/1999 | Ralph et al. |
| 6,039,761 A | 3/2000 | Li |
| 6,039,763 A | 3/2000 | Shelokov |
| 6,045,579 A | 4/2000 | Hochshuler |
| 6,099,531 A | 8/2000 | Bonutti |
| 6,102,950 A | 8/2000 | Vaccaro |
| 6,106,557 A | 8/2000 | Robioneck et al. |
| 6,113,637 A | 9/2000 | Gill et al. |
| 6,113,638 A | 9/2000 | Williams et al. |
| 6,117,174 A | 9/2000 | Nolan |
| 6,127,597 A | 10/2000 | Beyar et al. |
| 6,129,763 A | 10/2000 | Chauvin et al. |
| 6,146,387 A | 11/2000 | Trott et al. |
| 6,176,882 B1 | 1/2001 | Biedermann et al. |
| 6,179,794 B1 | 1/2001 | Burras |
| 6,179,873 B1 | 1/2001 | Zientek |
| 6,183,517 B1 | 2/2001 | Suddaby |
| 6,193,757 B1 | 2/2001 | Foley et al. |
| 6,241,732 B1 | 6/2001 | Overaker et al. |
| 6,273,893 B1 | 8/2001 | McAllen et al. |
| 6,290,701 B1 | 9/2001 | Enayati et al. |
| 6,296,647 B1 | 10/2001 | Robioneck et al. |
| 6,302,914 B1 | 10/2001 | Michelson |
| 6,319,252 B1 | 11/2001 | McDevitt et al. |
| 6,332,895 B1 | 12/2001 | Suddaby |
| 6,368,350 B1 | 4/2002 | Erickson et al. |
| 6,368,351 B1 | 4/2002 | Glenn |
| 6,375,682 B1 | 4/2002 | Fleischmann et al. |
| 6,387,130 B1 | 5/2002 | Stone |
| 6,406,234 B2 | 6/2002 | Frigg et al. |
| 6,409,766 B1 | 6/2002 | Brett |
| 6,419,705 B1 | 7/2002 | Erickson |
| 6,419,706 B1 | 7/2002 | Graf |
| 6,436,140 B1 | 8/2002 | Liu et al. |
| 6,454,806 B1 | 9/2002 | Cohen et al. |
| 6,454,807 B1 | 9/2002 | Jackson |
| 6,468,310 B1 | 10/2002 | Ralph et al. |
| 6,488,710 B2 | 12/2002 | Besselink |
| 6,517,580 B1 | 2/2003 | Ramadan et al. |
| 6,527,772 B2 | 3/2003 | Enayati et al. |
| 6,527,804 B1 | 3/2003 | Gauchet et al. |
| 6,558,424 B2 | 5/2003 | Thalgott |
| 6,562,074 B2 | 5/2003 | Gerbec et al. |
| 6,582,468 B1 | 6/2003 | Gauchet |
| 6,589,244 B1 | 7/2003 | Sevrain et al. |
| 6,610,094 B2 | 8/2003 | Husson |
| 6,641,614 B1 | 11/2003 | Wagner et al. |
| 6,648,917 B2 | 11/2003 | Gerbec et al. |
| 6,676,665 B2 | 1/2004 | Foley et al. |
| 6,706,070 B1 | 3/2004 | Wagner et al. |
| 6,719,796 B2 | 4/2004 | Cohen et al. |
| 6,723,126 B1 | 4/2004 | Berry |
| 6,733,532 B1 | 5/2004 | Gauchet et al. |
| 6,740,117 B2 | 5/2004 | Ralph et al. |
| 6,743,255 B2 | 6/2004 | Ferree |
| 6,773,460 B2 | 8/2004 | Jackson |
| 6,793,678 B2 | 9/2004 | Hawkins |
| 6,805,714 B2 | 10/2004 | Sutcliffe |
| 6,855,167 B2 | 2/2005 | Shimp |
| 6,863,673 B2 | 3/2005 | Gerbec et al. |
| 6,881,229 B2 | 4/2005 | Khandkar et al. |
| 6,893,464 B2 | 5/2005 | Kiester |
| 6,936,071 B1 | 8/2005 | Marnay et al. |
| 6,953,477 B2 | 10/2005 | Berry |
| 6,955,691 B2 | 10/2005 | Chae et al. |
| 6,969,404 B2 | 11/2005 | Ferree |
| 6,969,405 B2 | 11/2005 | Suddaby |
| 7,018,412 B2 | 3/2006 | Ferreira et al. |
| 7,018,416 B2 | 3/2006 | Hanson et al. |
| 7,037,339 B2 | 5/2006 | Houfburg et al. |
| 7,074,203 B1 | 7/2006 | Johanson et al. |
| 7,083,650 B2 | 8/2006 | Moskowitz et al. |
| 7,094,257 B2 | 8/2006 | Mujwid et al. |
| 7,128,744 B2 | 10/2006 | Weaver et al. |
| 7,156,876 B2 | 1/2007 | Moumene et al. |
| 7,211,112 B2 | 5/2007 | Baynham et al. |
| 7,217,293 B2 | 5/2007 | Branch |
| 7,220,280 B2 | 5/2007 | Kast et al. |
| 7,223,292 B2 | 5/2007 | Messerli et al. |
| 7,226,483 B2 | 6/2007 | Gerber et al. |
| 7,235,101 B2 | 6/2007 | Berry et al. |
| 7,237,424 B2 | 7/2007 | Crutchley et al. |
| 7,326,248 B2 | 2/2008 | Michelson |
| 7,341,413 B2 | 3/2008 | Morris et al. |
| 7,341,589 B2 | 3/2008 | Weaver et al. |
| 7,485,135 B2 | 2/2009 | Steiger et al. |
| 7,503,933 B2 | 3/2009 | Michelson |
| 7,507,241 B2 | 3/2009 | Levy et al. |
| 7,517,363 B2 | 4/2009 | Rogers |
| 7,569,074 B2 | 8/2009 | Eisermann et al. |
| 7,618,458 B2 | 11/2009 | Biedermann et al. |

(56) References Cited

U.S. PATENT DOCUMENTS

| | | |
|---|---|---|
| 7,621,950 B1 | 11/2009 | Globerman et al. |
| 7,621,960 B2 | 11/2009 | Boyd et al. |
| 7,637,949 B2 | 12/2009 | Hart |
| 7,691,147 B2 | 4/2010 | Gutlin et al. |
| 7,703,727 B2 | 4/2010 | Selness |
| 7,722,612 B2 | 5/2010 | Sala et al. |
| 7,722,674 B1 | 5/2010 | Grotz |
| 7,749,270 B2 | 7/2010 | Peterman |
| 7,771,473 B2 | 8/2010 | Thramann |
| 7,785,368 B2 | 8/2010 | Schaller |
| 7,789,914 B2 | 9/2010 | Michelson |
| 7,819,921 B2 | 10/2010 | Grotz |
| 7,824,445 B2 | 11/2010 | Biro et al. |
| 7,837,734 B2 | 11/2010 | Zucherman et al. |
| 7,846,206 B2 | 12/2010 | Oglaza et al. |
| 7,850,733 B2 | 12/2010 | Baynham et al. |
| 7,854,766 B2 | 12/2010 | Moskowitz et al. |
| 7,874,980 B2 | 1/2011 | Sonnenschein et al. |
| 7,879,098 B1 | 2/2011 | Simmons |
| 7,887,589 B2 | 2/2011 | Glenn et al. |
| 7,909,870 B2 | 3/2011 | Kraus |
| 7,922,729 B2 | 4/2011 | Michelson |
| 7,951,199 B2 | 5/2011 | Miller |
| 7,985,231 B2 | 7/2011 | Sankaran |
| 7,993,403 B2 | 8/2011 | Foley et al. |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,043,381 B2 | 10/2011 | Hestad et al. |
| 8,062,375 B2 | 11/2011 | Glerum et al. |
| 8,075,621 B2 | 12/2011 | Michelson |
| 8,105,382 B2 | 1/2012 | Olmos et al. |
| 8,177,812 B2 | 5/2012 | Sankaran |
| 8,192,495 B2 | 6/2012 | Simpson et al. |
| 8,221,501 B2 | 7/2012 | Eisermann et al. |
| 8,221,502 B2 | 7/2012 | Branch |
| 8,231,681 B2 | 7/2012 | Castleman et al. |
| 8,236,058 B2 | 8/2012 | Fabian et al. |
| 8,241,358 B2 | 8/2012 | Butler et al. |
| 8,257,442 B2 | 9/2012 | Edie et al. |
| 8,262,666 B2 | 9/2012 | Baynham et al. |
| 8,267,939 B2 | 9/2012 | Cipoletti et al. |
| 8,273,128 B2 | 9/2012 | Oh et al. |
| 8,287,599 B2 | 10/2012 | McGuckin |
| 8,303,663 B2 | 11/2012 | Jimenez et al. |
| 8,323,345 B2 | 12/2012 | Sledge |
| 8,328,852 B2 | 12/2012 | Zehavi et al. |
| 8,337,559 B2 | 12/2012 | Hansell et al. |
| 8,353,961 B2 | 1/2013 | McClintock |
| 8,382,842 B2 | 2/2013 | Greenhalgh et al. |
| 8,398,713 B2 | 3/2013 | Weiman |
| 8,403,990 B2 | 3/2013 | Dryer et al. |
| 8,409,291 B2 | 4/2013 | Blackwell et al. |
| 8,435,298 B2 | 5/2013 | Weiman |
| 8,454,617 B2 | 6/2013 | Schaller |
| 8,486,148 B2 | 7/2013 | Butler et al. |
| 8,491,657 B2 | 7/2013 | Attia et al. |
| 8,491,659 B2 | 7/2013 | Weiman |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim |
| 8,591,585 B2 | 11/2013 | McLaughlin |
| 8,603,170 B2 | 12/2013 | Cipoletti et al. |
| 8,623,091 B2 | 1/2014 | Suedkamp et al. |
| 8,628,576 B2 | 1/2014 | Triplett et al. |
| 8,628,578 B2 | 1/2014 | Miller et al. |
| 8,632,595 B2 | 1/2014 | Weiman |
| 8,663,329 B2 | 3/2014 | Ernst |
| 8,668,740 B2 | 3/2014 | Rhoda et al. |
| 8,679,183 B2 | 3/2014 | Glerum et al. |
| 8,685,098 B2 | 4/2014 | Glerum et al. |
| 8,696,751 B2 | 4/2014 | Ashley et al. |
| 8,709,086 B2 | 4/2014 | Glerum et al. |
| 8,715,351 B1 | 5/2014 | Pinto |
| 8,721,723 B2 | 5/2014 | Hansell et al. |
| 8,728,160 B2 | 5/2014 | Globerman et al. |
| 8,753,398 B2 | 6/2014 | Gordon et al. |
| 8,771,360 B2 | 7/2014 | Jimenez et al. |
| 8,778,025 B2 | 7/2014 | Ragab et al. |
| 8,795,366 B2 | 8/2014 | Varela |
| 8,828,085 B1 | 9/2014 | Jensen |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,307 B2 | 12/2014 | Hawkins et al. |
| 8,926,704 B2 | 1/2015 | Glerum |
| 8,936,641 B2 | 1/2015 | Cain |
| 8,940,052 B2 | 1/2015 | Lechmann et al. |
| 8,974,508 B2 | 3/2015 | Stephan et al. |
| 8,986,387 B1 | 3/2015 | To et al. |
| 9,005,291 B2 | 4/2015 | Loebl et al. |
| 9,039,767 B2 | 5/2015 | Raymond et al. |
| 9,039,771 B2 | 5/2015 | Glerum et al. |
| 9,060,876 B1 | 6/2015 | To et al. |
| 9,078,767 B1 | 7/2015 | McLean |
| 9,095,446 B2 | 8/2015 | Landry et al. |
| 9,095,447 B2 | 8/2015 | Barreiro et al. |
| 9,101,488 B2 | 8/2015 | Malandain |
| 9,101,489 B2 | 8/2015 | Protopsaltis et al. |
| 9,107,766 B1 | 8/2015 | Mclean et al. |
| 2002/0010070 A1 | 1/2002 | Cales et al. |
| 2002/0068976 A1 | 6/2002 | Jackson |
| 2002/0068977 A1 | 6/2002 | Jackson |
| 2002/0128715 A1 | 9/2002 | Bryan et al. |
| 2002/0128716 A1 | 9/2002 | Cohen et al. |
| 2002/0138146 A1 | 9/2002 | Jackson |
| 2002/0151976 A1 | 10/2002 | Foley et al. |
| 2002/0165612 A1 | 11/2002 | Gerber et al. |
| 2003/0004575 A1 | 1/2003 | Erickson |
| 2003/0004576 A1 | 1/2003 | Thalgott |
| 2003/0023305 A1 | 1/2003 | McKay |
| 2003/0040799 A1 | 2/2003 | Boyd et al. |
| 2003/0065396 A1 | 4/2003 | Michelson |
| 2003/0078667 A1 | 4/2003 | Manasas et al. |
| 2003/0130739 A1 | 7/2003 | Gerbec et al. |
| 2003/0135275 A1 | 7/2003 | Garcia |
| 2003/0139812 A1 | 7/2003 | Garcia |
| 2003/0139813 A1 | 7/2003 | Messerli et al. |
| 2003/0233145 A1 | 12/2003 | Landry et al. |
| 2004/0030387 A1 | 2/2004 | Landry et al. |
| 2004/0064144 A1 | 4/2004 | Johnson et al. |
| 2004/0087947 A1 | 5/2004 | Lim |
| 2004/0088055 A1 | 5/2004 | Hanson et al. |
| 2004/0127991 A1 | 7/2004 | Ferree |
| 2004/0133280 A1 | 7/2004 | Trieu |
| 2004/0153065 A1 | 8/2004 | Lim |
| 2004/0153156 A1 | 8/2004 | Cohen et al. |
| 2004/0162618 A1 | 8/2004 | Mujwid et al. |
| 2004/0172133 A1 | 9/2004 | Gerber et al. |
| 2004/0186570 A1 | 9/2004 | Rapp |
| 2004/0186577 A1 | 9/2004 | Ferree |
| 2004/0230309 A1 | 11/2004 | DiMauro |
| 2005/0038515 A1 | 2/2005 | Kunzler |
| 2005/0113916 A1 | 5/2005 | Branch |
| 2005/0113917 A1 | 5/2005 | Chae et al. |
| 2005/0125062 A1 | 6/2005 | Biedermann et al. |
| 2005/0143818 A1 | 6/2005 | Yuan et al. |
| 2005/0165485 A1 | 7/2005 | Trieu |
| 2005/0222681 A1 | 10/2005 | Richley et al. |
| 2005/0256576 A1 | 11/2005 | Moskowitz et al. |
| 2005/0261769 A1 | 11/2005 | Moskowitz et al. |
| 2005/0278026 A1 | 12/2005 | Gordon et al. |
| 2006/0052788 A1 | 3/2006 | Thelen et al. |
| 2006/0058876 A1 | 3/2006 | McKinley |

(56) References Cited

U.S. PATENT DOCUMENTS

| | | |
|---|---|---|
| 2006/0058880 A1 | 3/2006 | Wysocki |
| 2006/0100706 A1 | 5/2006 | Shadduck et al. |
| 2006/0122701 A1 | 6/2006 | Kiester |
| 2006/0122703 A1 | 6/2006 | Aebi et al. |
| 2006/0129244 A1 | 6/2006 | Ensign |
| 2006/0136062 A1 | 6/2006 | DiNello et al. |
| 2006/0142858 A1 | 6/2006 | Colleran et al. |
| 2006/0206207 A1 | 9/2006 | Dryer et al. |
| 2006/0235531 A1 | 10/2006 | Buettner |
| 2006/0253201 A1 | 11/2006 | McLuen |
| 2006/0265075 A1 | 11/2006 | Baumgartner et al. |
| 2006/0265077 A1 | 11/2006 | Zwirkoski |
| 2007/0010886 A1 | 1/2007 | Banick et al. |
| 2007/0055377 A1 | 3/2007 | Hanson et al. |
| 2007/0118222 A1 | 5/2007 | Lang |
| 2007/0149978 A1 | 6/2007 | Shezifi et al. |
| 2007/0173939 A1 | 7/2007 | Kim et al. |
| 2007/0173940 A1 | 7/2007 | Hestad et al. |
| 2007/0191959 A1 | 8/2007 | Hartmann et al. |
| 2007/0198089 A1 | 8/2007 | Moskowitz et al. |
| 2007/0208423 A1 | 9/2007 | Messerli et al. |
| 2007/0219634 A1 | 9/2007 | Greenhalgh et al. |
| 2007/0233244 A1 | 10/2007 | Lopez et al. |
| 2007/0270968 A1 | 11/2007 | Baynham et al. |
| 2007/0276375 A1 | 11/2007 | Rapp |
| 2007/0299521 A1 | 12/2007 | Glenn |
| 2008/0009877 A1 | 1/2008 | Sankaran et al. |
| 2008/0015701 A1 | 1/2008 | Garcia et al. |
| 2008/0021556 A1 | 1/2008 | Edie |
| 2008/0021558 A1 | 1/2008 | Thramann |
| 2008/0027550 A1 | 1/2008 | Link et al. |
| 2008/0033440 A1 | 2/2008 | Moskowitz et al. |
| 2008/0039846 A1 | 2/2008 | Lee et al. |
| 2008/0058944 A1 | 3/2008 | Duplessis et al. |
| 2008/0065219 A1 | 3/2008 | Dye |
| 2008/0082173 A1 | 4/2008 | Delurio et al. |
| 2008/0132934 A1 | 6/2008 | Reiley |
| 2008/0140207 A1 | 6/2008 | Olmos |
| 2008/0147193 A1 | 6/2008 | Matthis et al. |
| 2008/0161927 A1 | 7/2008 | Savage |
| 2008/0167657 A1 | 7/2008 | Greenhalgh |
| 2008/0177388 A1 | 7/2008 | Patterson et al. |
| 2008/0183204 A1 | 7/2008 | Greenhalgh et al. |
| 2008/0195209 A1 | 8/2008 | Garcia et al. |
| 2008/0234682 A1 | 9/2008 | Park |
| 2008/0243251 A1 | 10/2008 | Stad et al. |
| 2008/0243254 A1 | 10/2008 | Butler |
| 2008/0249622 A1 | 10/2008 | Gray |
| 2008/0281425 A1 | 11/2008 | Thalgott |
| 2009/0005873 A1 | 1/2009 | Slivka et al. |
| 2009/0030423 A1 | 1/2009 | Puno |
| 2009/0054991 A1 | 2/2009 | Biyani |
| 2009/0074538 A1 | 3/2009 | Richie |
| 2009/0076610 A1 | 3/2009 | Afzal |
| 2009/0099568 A1 | 4/2009 | Lowry et al. |
| 2009/0112320 A1 | 4/2009 | Kraus |
| 2009/0112324 A1 | 4/2009 | Refai et al. |
| 2009/0164020 A1* | 6/2009 | Janowski ............... A61F 2/4465 623/17.16 |
| 2009/0177284 A1 | 7/2009 | Rogers et al. |
| 2009/0222096 A1 | 9/2009 | Trieu |
| 2009/0222099 A1 | 9/2009 | Liu et al. |
| 2009/0234398 A1 | 9/2009 | Chirico et al. |
| 2009/0240335 A1 | 9/2009 | Arcenio et al. |
| 2009/0248159 A1 | 10/2009 | Aflatoon |
| 2009/0281580 A1 | 11/2009 | Emannuel |
| 2009/0292361 A1 | 11/2009 | Lopez et al. |
| 2010/0016905 A1 | 1/2010 | Greenhalgh et al. |
| 2010/0076559 A1 | 3/2010 | Bagga |
| 2010/0179594 A1 | 7/2010 | Theofilos et al. |
| 2010/0204795 A1 | 8/2010 | Greenhalgh |
| 2010/0234956 A1 | 9/2010 | Attia et al. |
| 2010/0262240 A1 | 10/2010 | Chavatte et al. |
| 2010/0286783 A1 | 11/2010 | Lechmann et al. |
| 2010/0324607 A1 | 12/2010 | Davis |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0093074 A1 | 4/2011 | Glerum et al. |
| 2011/0130835 A1 | 6/2011 | Ashley et al. |
| 2011/0130838 A1 | 6/2011 | Morgenstern et al. |
| 2011/0144753 A1 | 6/2011 | Marchek et al. |
| 2011/0172716 A1 | 7/2011 | Glerum |
| 2011/0270261 A1 | 11/2011 | Mast et al. |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0185049 A1 | 7/2012 | Varela |
| 2012/0197403 A1 | 8/2012 | Merves |
| 2012/0197405 A1 | 8/2012 | Cuevas et al. |
| 2012/0226357 A1 | 9/2012 | Varela |
| 2012/0232552 A1 | 9/2012 | Morgenstern et al. |
| 2012/0265309 A1 | 10/2012 | Glerum et al. |
| 2012/0290097 A1 | 11/2012 | Cipoletti et al. |
| 2012/0310350 A1 | 12/2012 | Farris et al. |
| 2012/0310352 A1 | 12/2012 | DiMauro et al. |
| 2013/0030536 A1 | 1/2013 | Rhoda et al. |
| 2013/0085572 A1 | 4/2013 | Glerum et al. |
| 2013/0085574 A1 | 4/2013 | Sledge |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0310939 A1 | 11/2013 | Fabian et al. |
| 2014/0025169 A1 | 1/2014 | Lechmann et al. |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Hauck |
| 2014/0114423 A1 | 4/2014 | Suedkamp et al. |
| 2014/0128977 A1 | 5/2014 | Glerum et al. |
| 2014/0135934 A1 | 5/2014 | Hansell et al. |
| 2014/0142706 A1 | 5/2014 | Hansell et al. |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0228959 A1 | 8/2014 | Niemiec et al. |
| 2014/0243981 A1 | 8/2014 | Davenport et al. |
| 2014/0243982 A1 | 8/2014 | Miller |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0277474 A1 | 9/2014 | Robinson et al. |
| 2014/0303731 A1 | 10/2014 | Glerum et al. |
| 2014/0303732 A1 | 10/2014 | Rhoda et al. |
| 2014/0324171 A1 | 10/2014 | Glerum et al. |
| 2015/0012097 A1 | 1/2015 | Ibarra et al. |
| 2015/0045894 A1 | 2/2015 | Hawkins et al. |
| 2015/0094812 A1 | 4/2015 | Cain et al. |
| 2015/0094813 A1 | 4/2015 | Lechmann et al. |

(56) References Cited

U.S. PATENT DOCUMENTS

| | | |
|---|---|---|
| 2015/0112438 A1 | 4/2015 | McLean |
| 2015/0173916 A1 | 6/2015 | Cain et al. |
| 2015/0182347 A1 | 7/2015 | Robinson |
| 2015/0216671 A1 | 8/2015 | Cain et al. |
| 2015/0216672 A1 | 8/2015 | Cain et al. |
| 2015/0250606 A1 | 9/2015 | Mclean |
| 2016/0045333 A1 | 2/2016 | Baynham |
| 2016/0242929 A1 | 8/2016 | Voellmicke et al. |
| 2016/0317317 A1 | 11/2016 | Marchek et al. |

FOREIGN PATENT DOCUMENTS

| | | |
|---|---|---|
| DE | 1979958 | 2/1968 |
| DE | 2804936 | 8/1979 |
| DE | 3245055 | 6/1984 |
| DE | 3911610 | 10/1990 |
| DE | 4012622 | 7/1997 |
| DE | 19543651 | 7/1997 |
| DE | 202008001079 | 3/2008 |
| EP | 0196409 B1 | 10/1986 |
| EP | 282161 | 9/1988 |
| EP | 678489 | 10/1995 |
| EP | 0841491 | 5/1998 |
| EP | 1290985 | 3/2003 |
| EP | 1532949 | 5/2005 |
| EP | 1541096 | 6/2005 |
| EP | 1683593 | 7/2006 |
| EP | 1698305 B1 | 8/2007 |
| EP | 1857064 A1 | 11/2007 |
| EP | 1843723 B1 | 3/2010 |
| EP | 2368529 | 9/2011 |
| EP | 2237748 B1 | 9/2012 |
| EP | 2764851 | 8/2014 |
| FR | 2718635 | 10/1995 |
| FR | 2730159 | 8/1996 |
| FR | 2738142 | 3/1997 |
| FR | 2874814 | 3/2006 |
| JP | 3011115 | 2/1991 |
| JP | 06-292686 | 10/1994 |
| JP | 11-504550 | 4/1999 |
| JP | 2002-516698 | 6/2002 |
| JP | 2002-195226 | 7/2002 |
| JP | 2003-526457 | 9/2003 |
| JP | 2005-523732 | 8/2005 |
| JP | 2006-507090 | 3/2006 |
| JP | 2006-516456 | 7/2006 |
| JP | 2007-54666 | 3/2007 |
| JP | 2011-509766 A | 3/2011 |
| WO | WO 94/04100 | 3/1994 |
| WO | WO 95/31158 | 11/1995 |
| WO | WO 97/00054 | 1/1997 |
| WO | WO 99/53871 | 10/1999 |
| WO | WO 00/11355 | 3/2000 |
| WO | WO 00/012033 | 3/2000 |
| WO | WO 00/53127 | 9/2000 |
| WO | WO 00/74605 | 12/2000 |
| WO | WO 01/01895 | 1/2001 |
| WO | WO 0101893 | 1/2001 |
| WO | WO 01/17464 | 3/2001 |
| WO | WO 03/051557 | 6/2003 |
| WO | WO 03/057055 A1 | 7/2003 |
| WO | WO 2005/112834 | 12/2005 |
| WO | WO 2006/047587 | 5/2006 |
| WO | WO 2006/058281 | 6/2006 |
| WO | WO 2006/065419 | 6/2006 |
| WO | WO 2006/081843 | 8/2006 |
| WO | WO 2007/028098 | 3/2007 |
| WO | WO 2007/048012 | 4/2007 |
| WO | WO 2007/133410 A2 | 11/2007 |
| WO | WO 2008/004057 A2 | 1/2008 |
| WO | WO 2008/044057 | 4/2008 |
| WO | WO 2007/009107 | 8/2008 |
| WO | WO 2009/092102 | 7/2009 |
| WO | WO 2009/064787 | 8/2009 |
| WO | WO 2009/124269 | 10/2009 |
| WO | WO 2009/143496 | 11/2009 |
| WO | WO 2010/068725 | 6/2010 |
| WO | WO 2010/148112 | 12/2010 |
| WO | WO 2011/005788 | 1/2011 |
| WO | WO 2011/142761 | 11/2011 |
| WO | WO 2012/009152 | 1/2012 |
| WO | WO 2012/089317 | 7/2012 |
| WO | WO 2012/135764 | 10/2012 |
| WO | WO 2013/006669 | 1/2013 |
| WO | WO 2013/023096 | 2/2013 |
| WO | WO 2013/025876 | 2/2013 |
| WO | WO 2013/043850 | 5/2013 |
| WO | WO 2013/062903 | 5/2013 |
| WO | WO 2013/082184 | 6/2013 |
| WO | WO 2013/158294 | 10/2013 |
| WO | WO 2013/173767 | 11/2013 |
| WO | WO 2013/184946 | 12/2013 |
| WO | WO 2014/018098 | 1/2014 |
| WO | WO 2014/026007 | 2/2014 |
| WO | WO 2014/035962 | 3/2014 |
| WO | WO 2014/088521 | 6/2014 |
| WO | WO 2014/116891 | 7/2014 |
| WO | WO 2014/144696 | 9/2014 |

OTHER PUBLICATIONS

U.S. Appl. No. 14/640,220, filed Mar. 6, 2015, Marden.
U.S. Appl. No. 14/685,358, filed Apr. 13, 2015, Marden et al.
U.S. Appl. No. 14/685,402, filed Apr. 13, 2015, Cain.
U.S. Appl. No. 14/790,866, filed Jul. 2, 2015, Thommen et al.
International Patent Application No. PCT/US2013/029014, International Search Report dated Jul. 1, 2013, 7 pages.
Chiang, Biomechanical Comparison of Instrumented Posterior Lumbar Interbody Fusion with One or Two Cages by Finite Element Analysis, Spine, 2006, pp. E682-E689, vol. 31(19), Lippincott Williams & Wilkins, Inc.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Gore, Technique of Cervical Interbody Fusion, Clinical Orthopaedics and Related Research, 1984, pp. 191-195, No. 188.
Hunt, Expanable cage placement via a posterolateral approach in lumbar spine reconstructions, Journal of Neurosurgery: Spine, 2006, pp. 271-274, vol. 5.
Krbec, [Replacement of the vertebral body with an expansion implant (Synex)], Acta Chir Orthop Traumatol Cech, 2002, pp. 158-162, vol. 69(3).
Polikeit, The importance of the endplate for interbody cages in the lumbar spine, Eur Spine J, 2003, pp. 556-561, vol. 12.
Shin, Posterior Lumbar Interbody Fusion via a Unilateral Approach, Yonsei Medical Journal, 2006, pp. 319-325, vol. 47(3).
Hoogland, T. et al., Total Lumbar Intervertebral Disc Replacement: testing of a New Articulating Space in Human Cadaver Spines- 24 1 Annual ORS, Dallas TX, Feb. 21-23, 1978, 8 pages.
Link SB Charite Brochure—Intervertebral Prosthesis 1988, 29 pages.

* cited by examiner

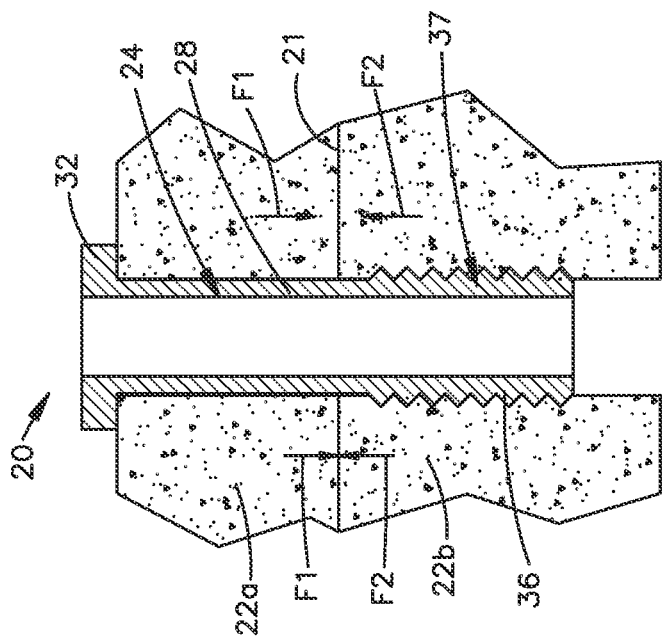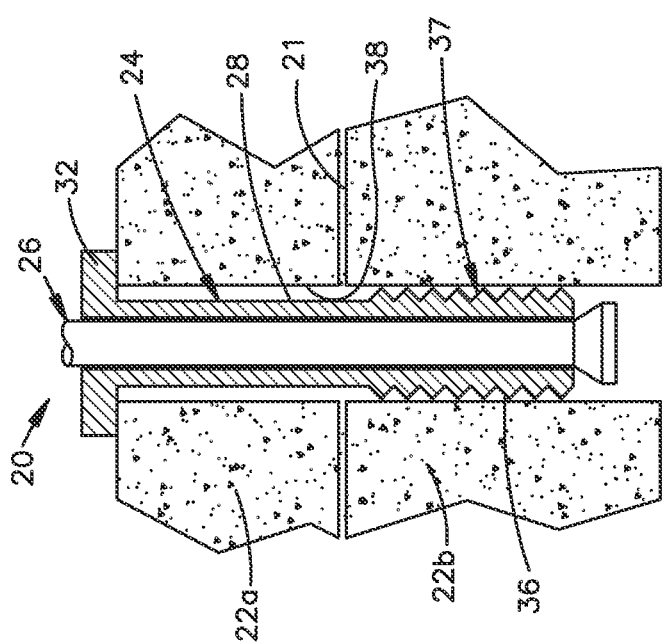

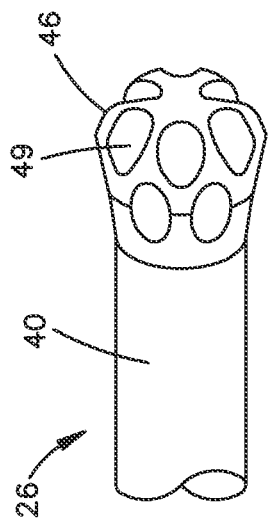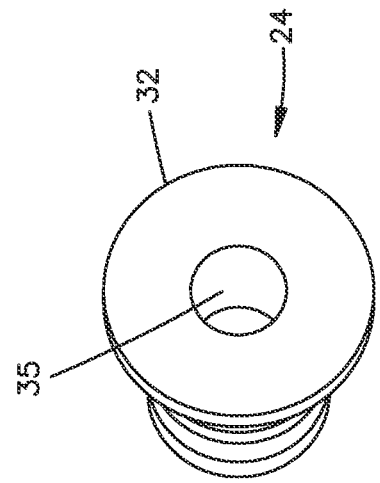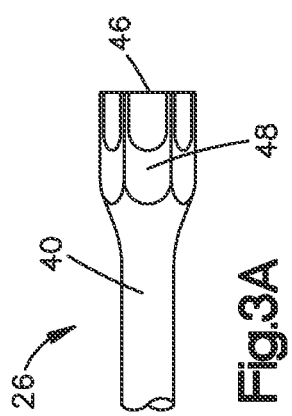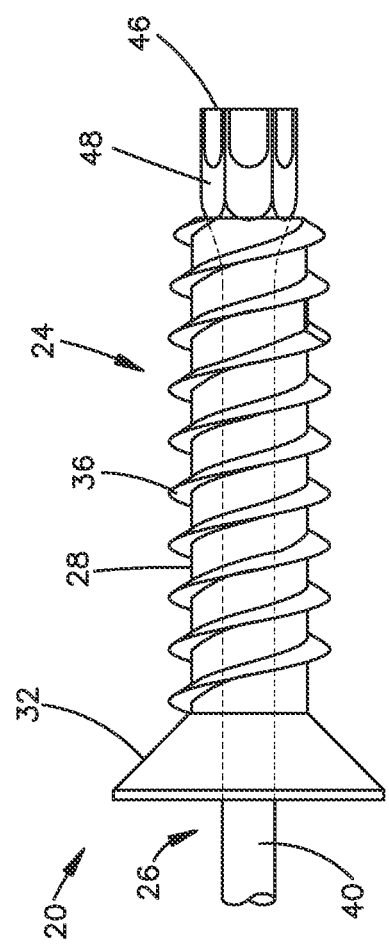

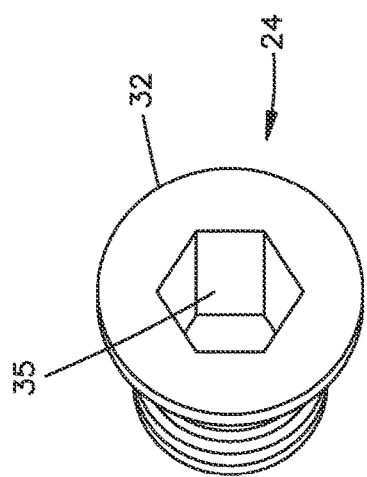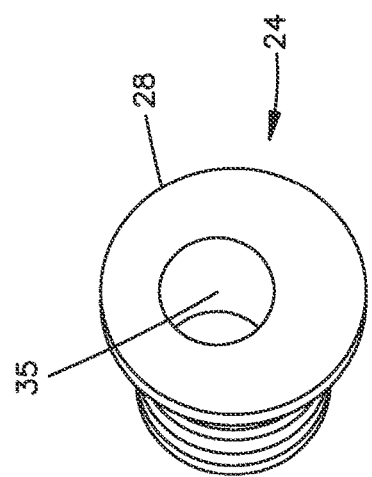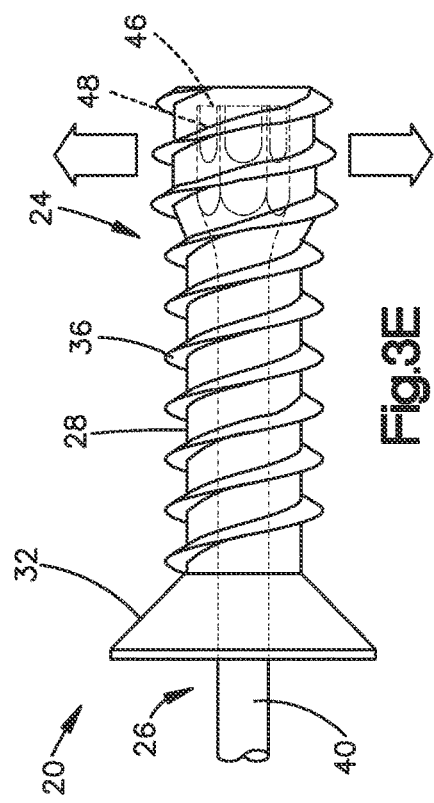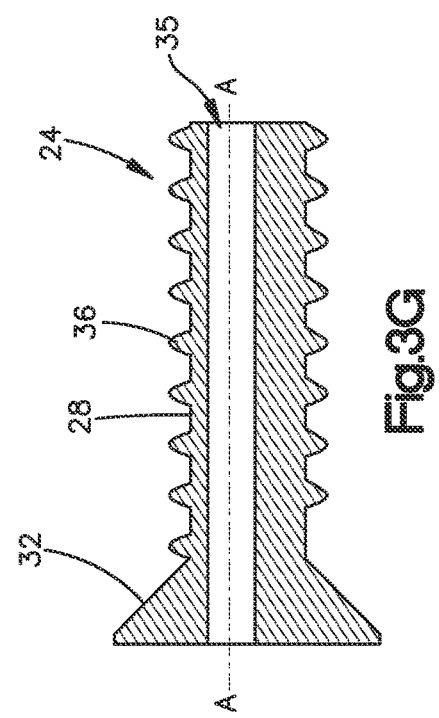

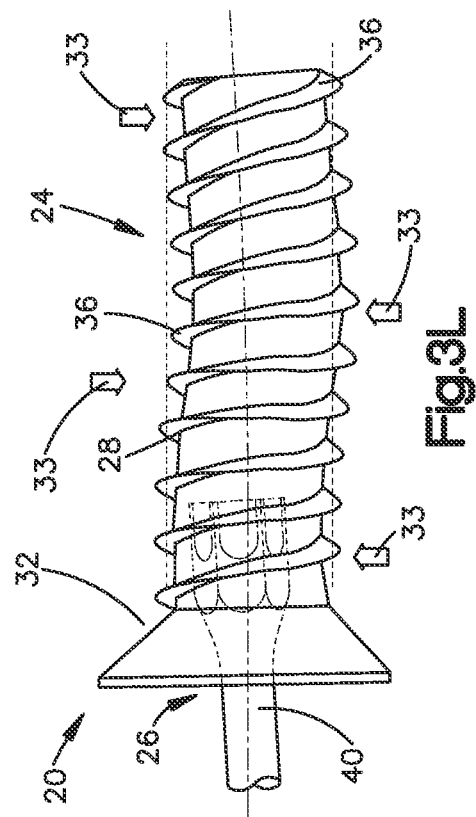
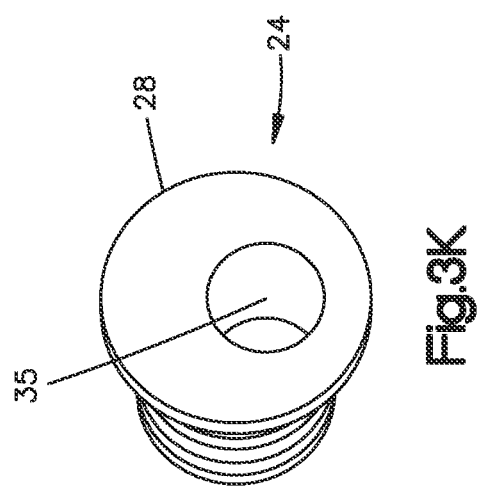
Fig.3L
Fig.3K

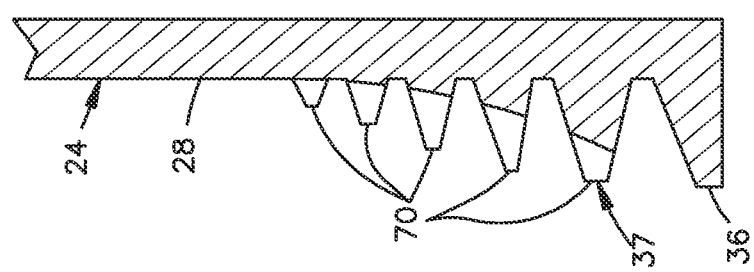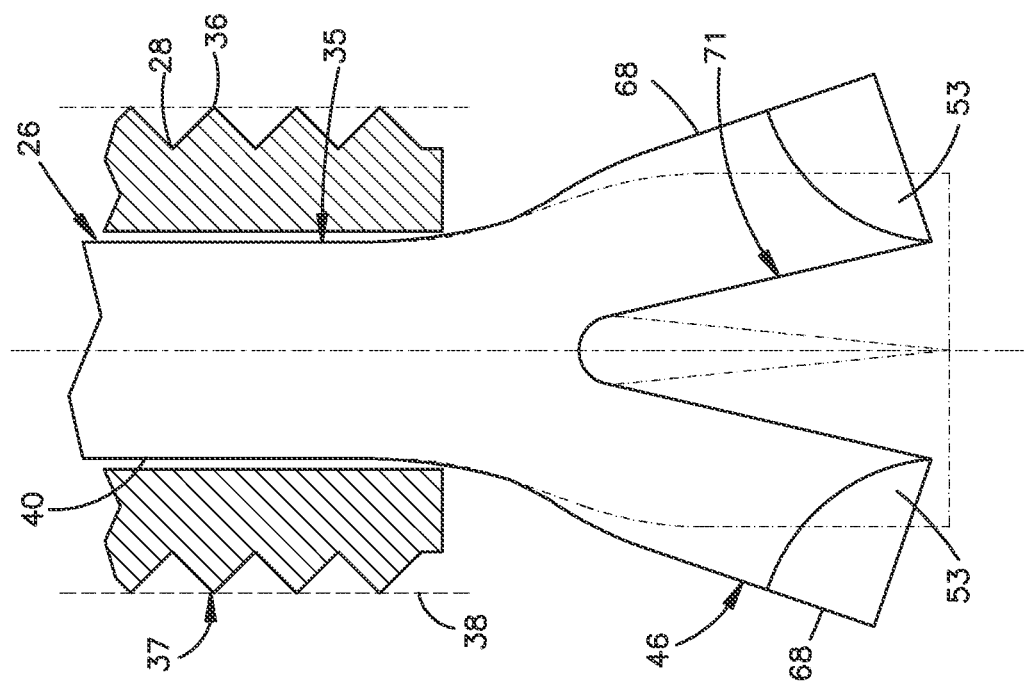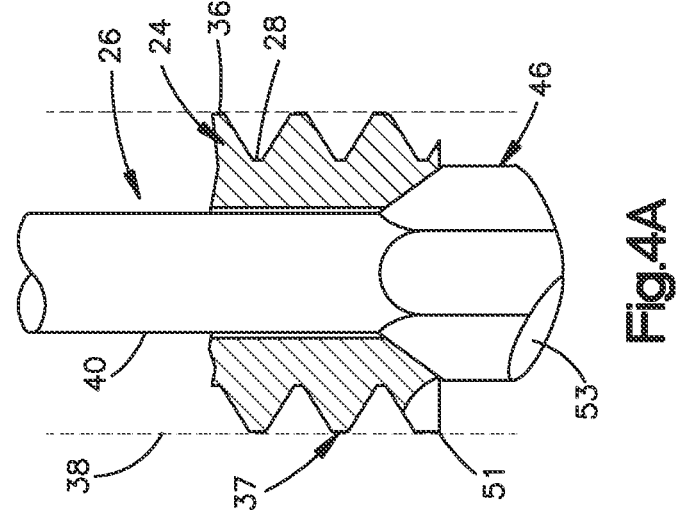

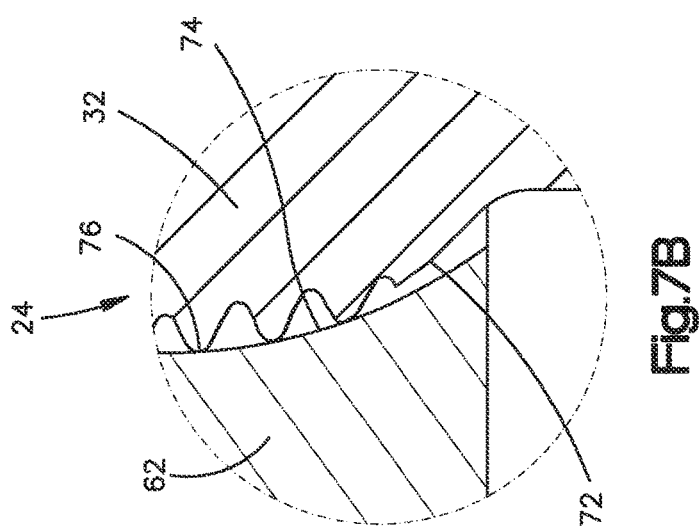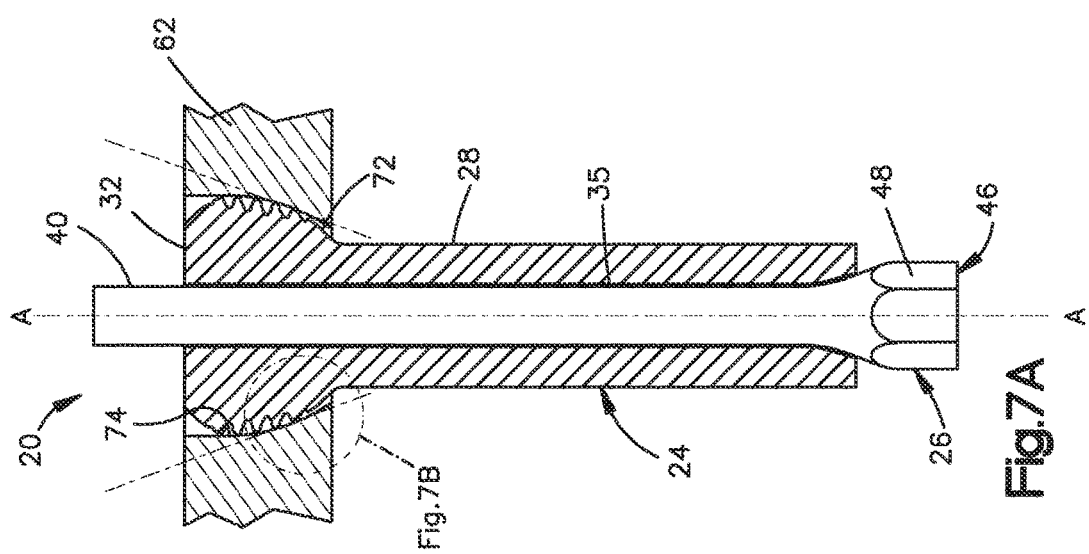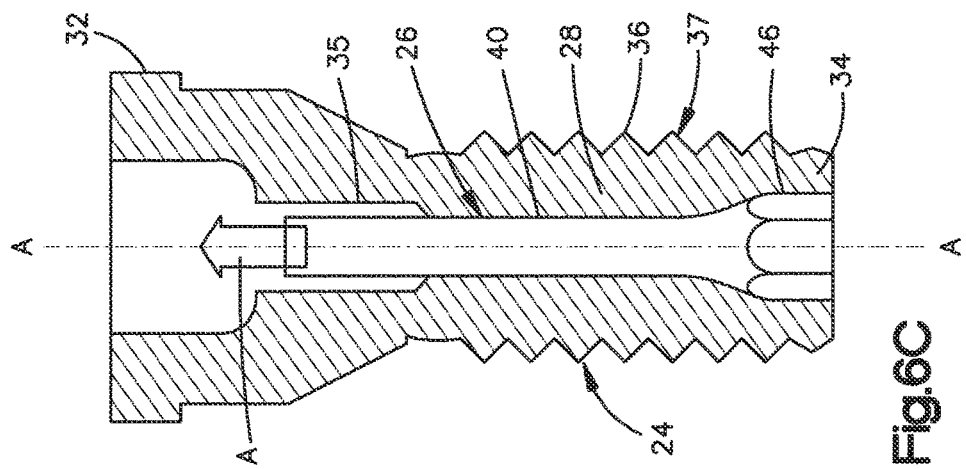

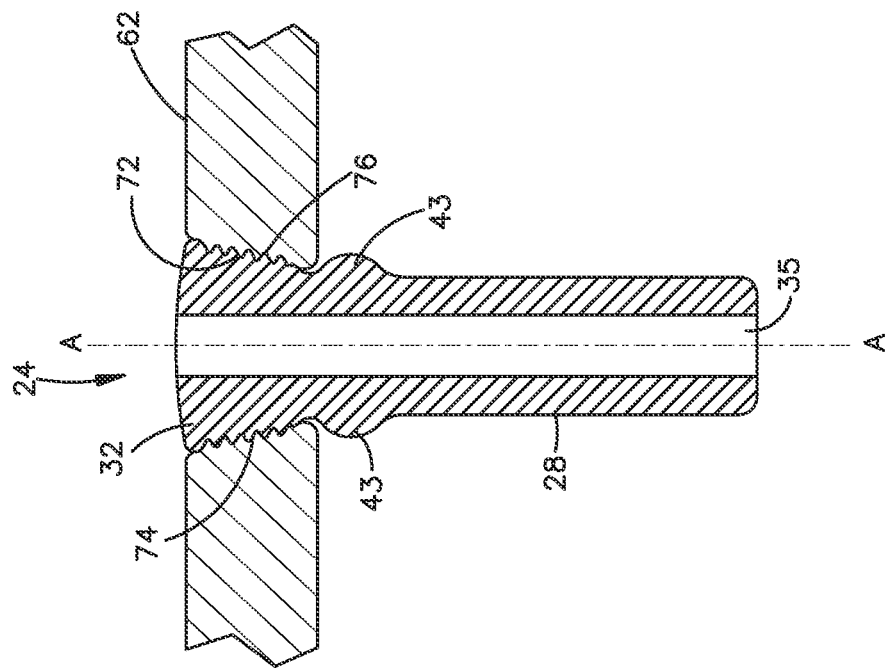
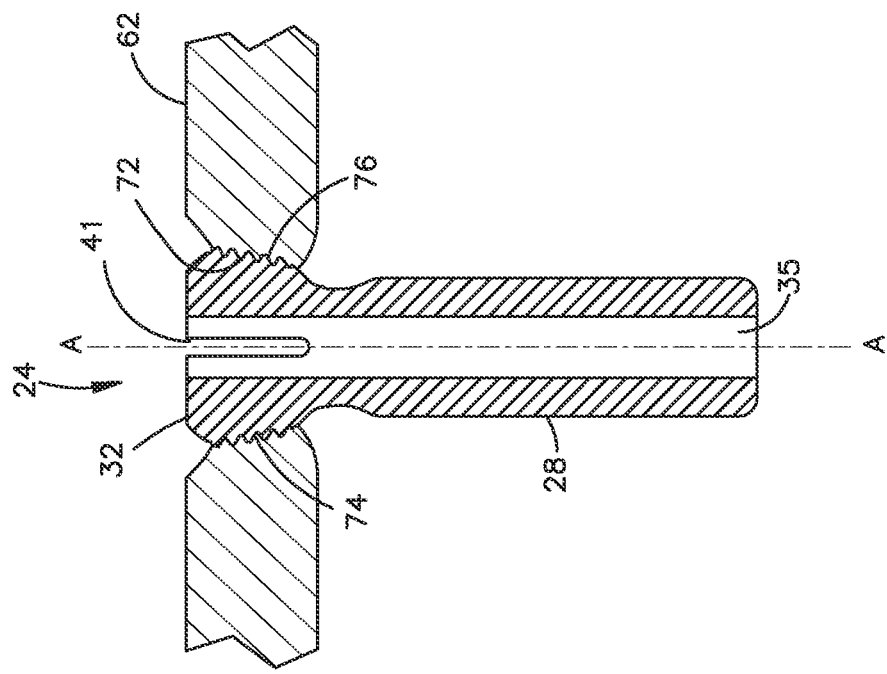

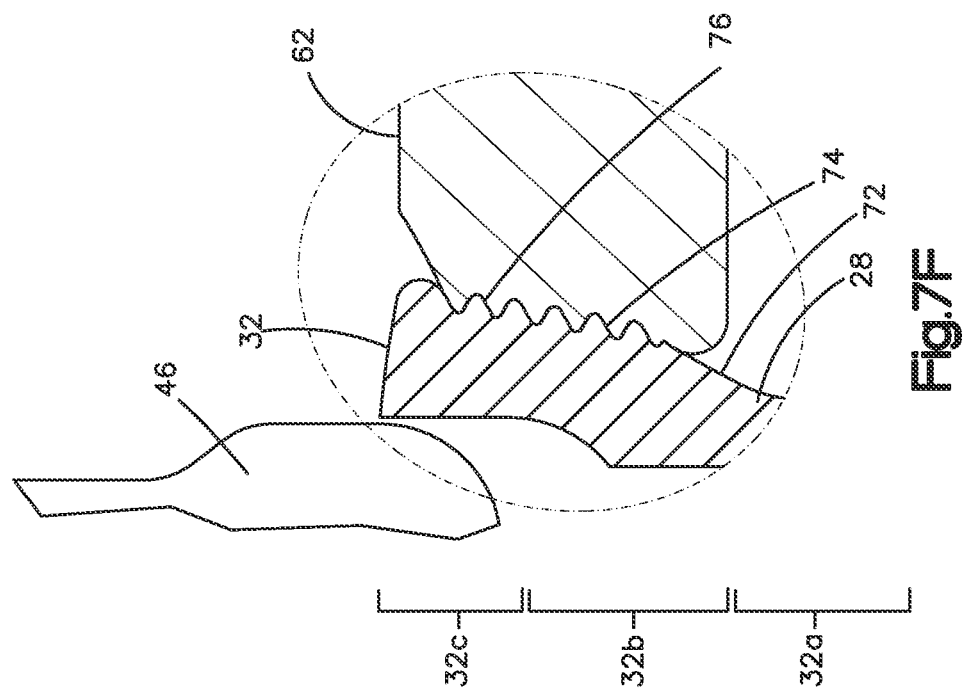
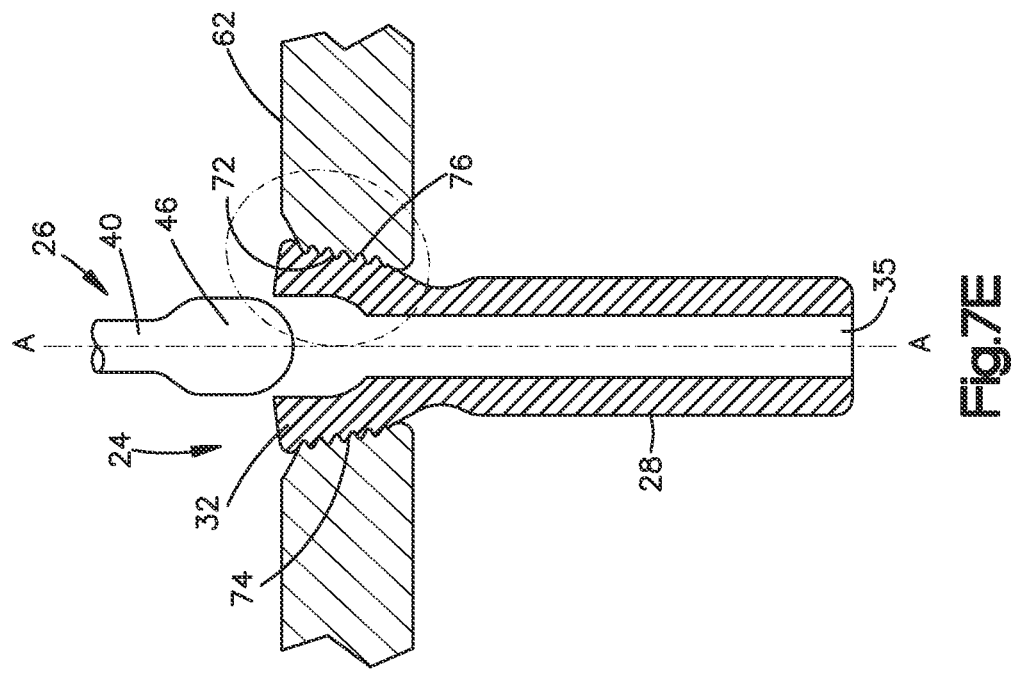
Fig. 7F
Fig. 7E

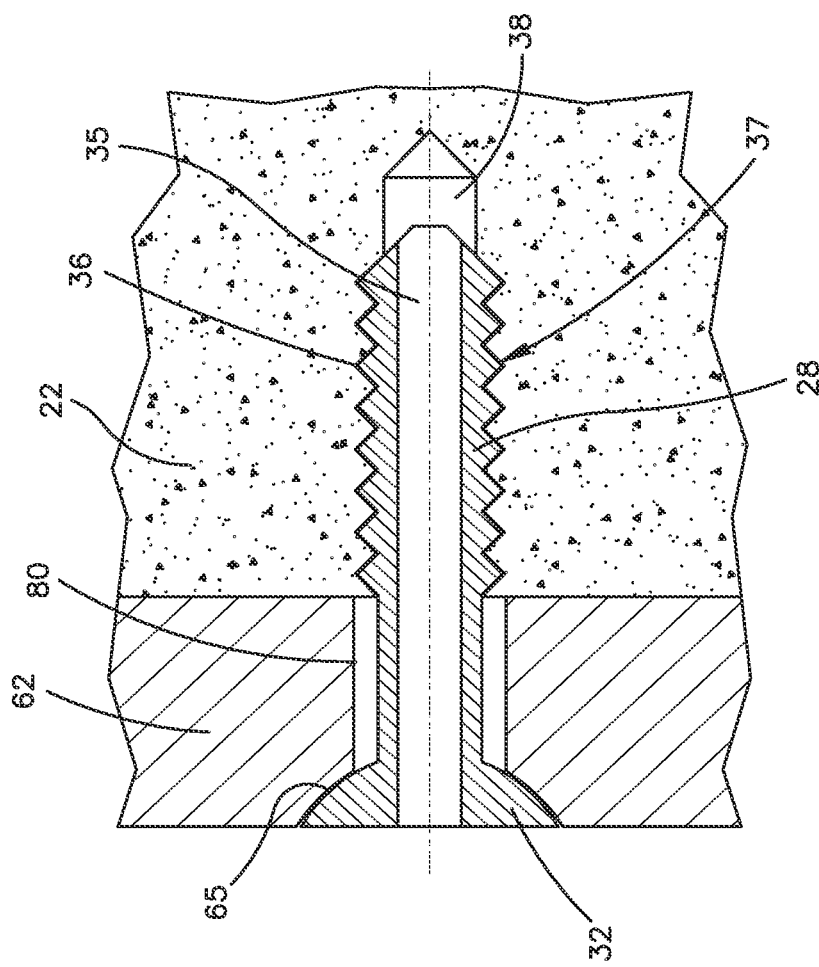

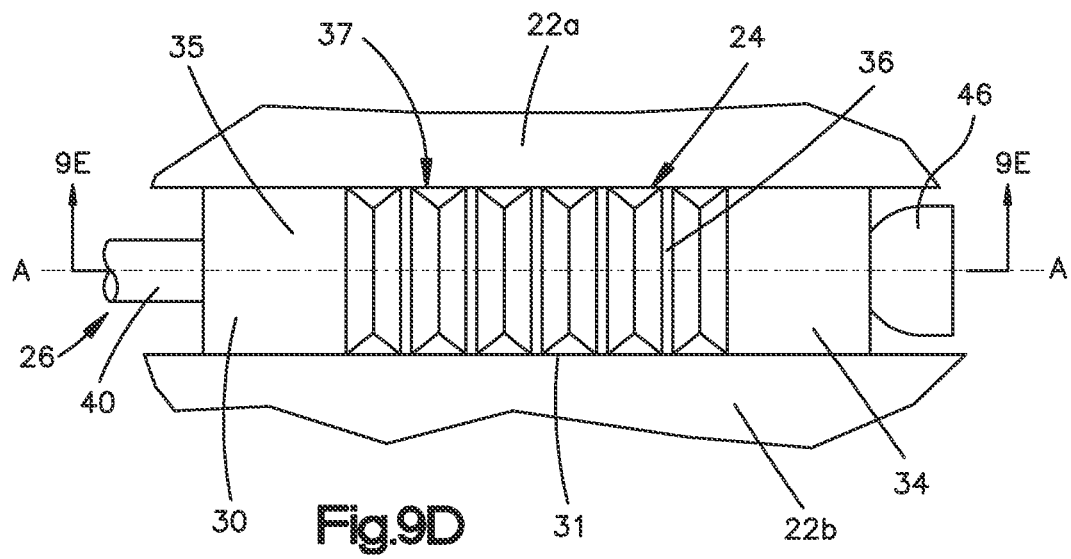
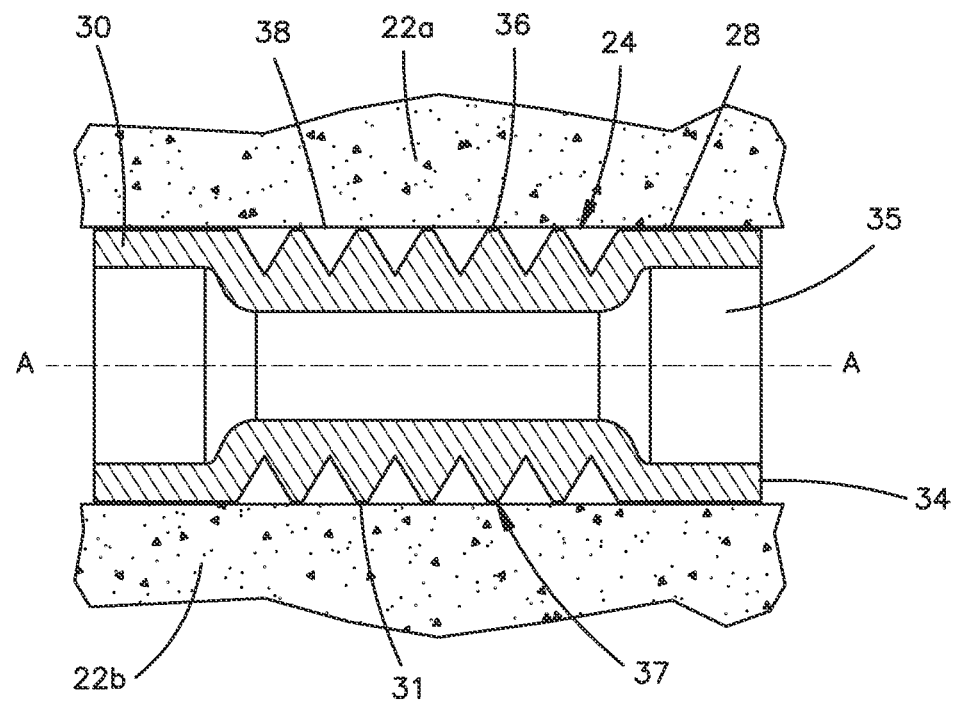

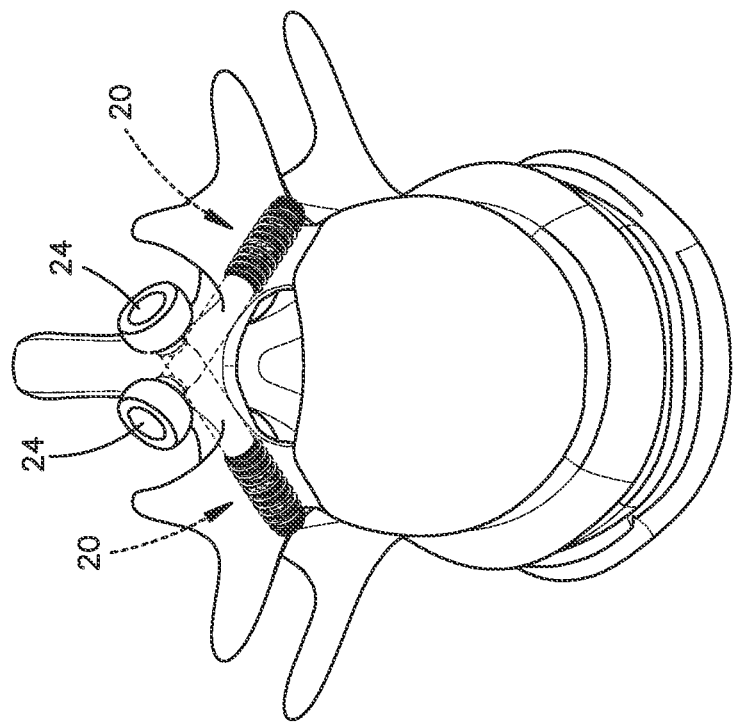
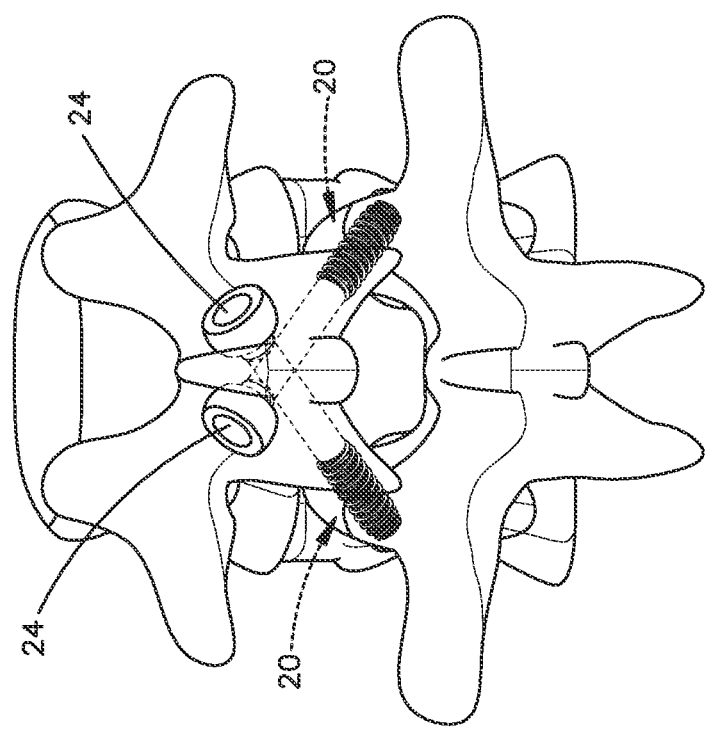

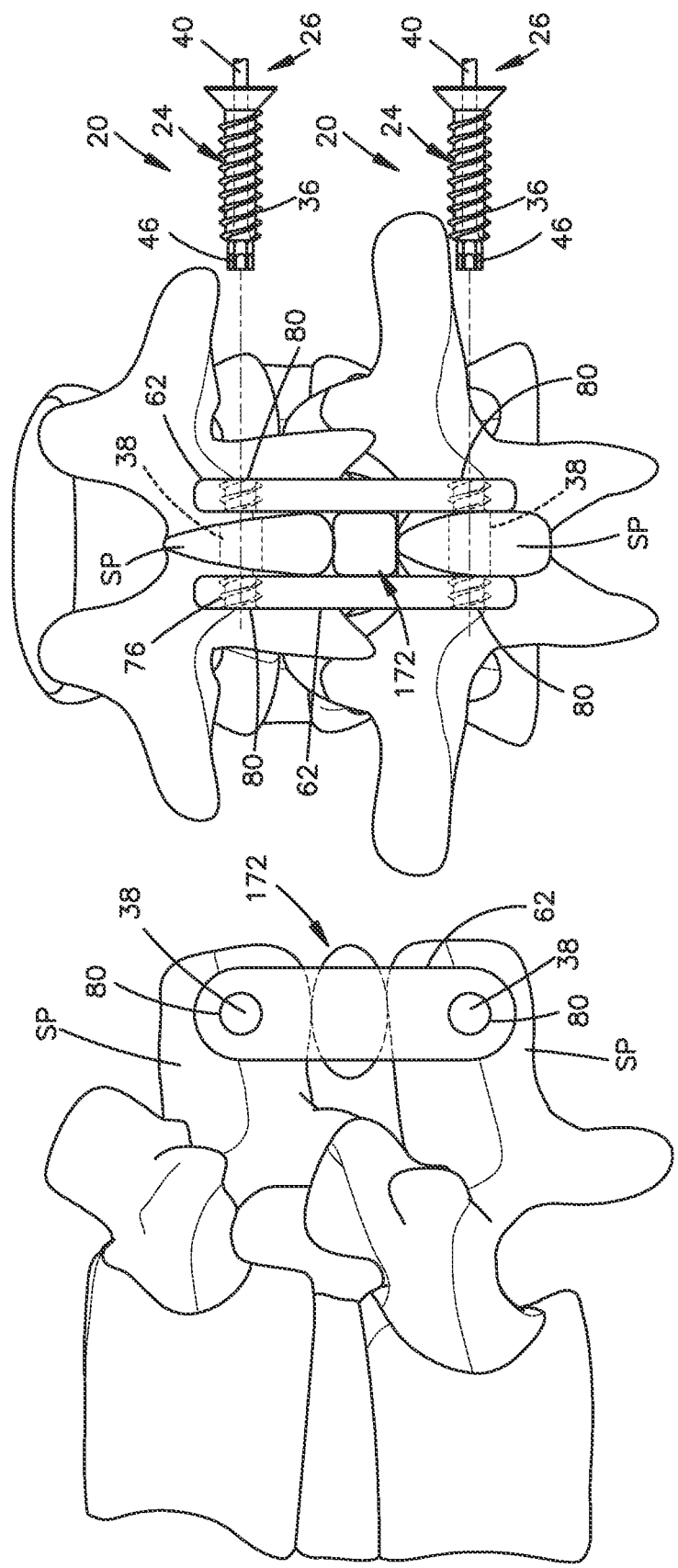

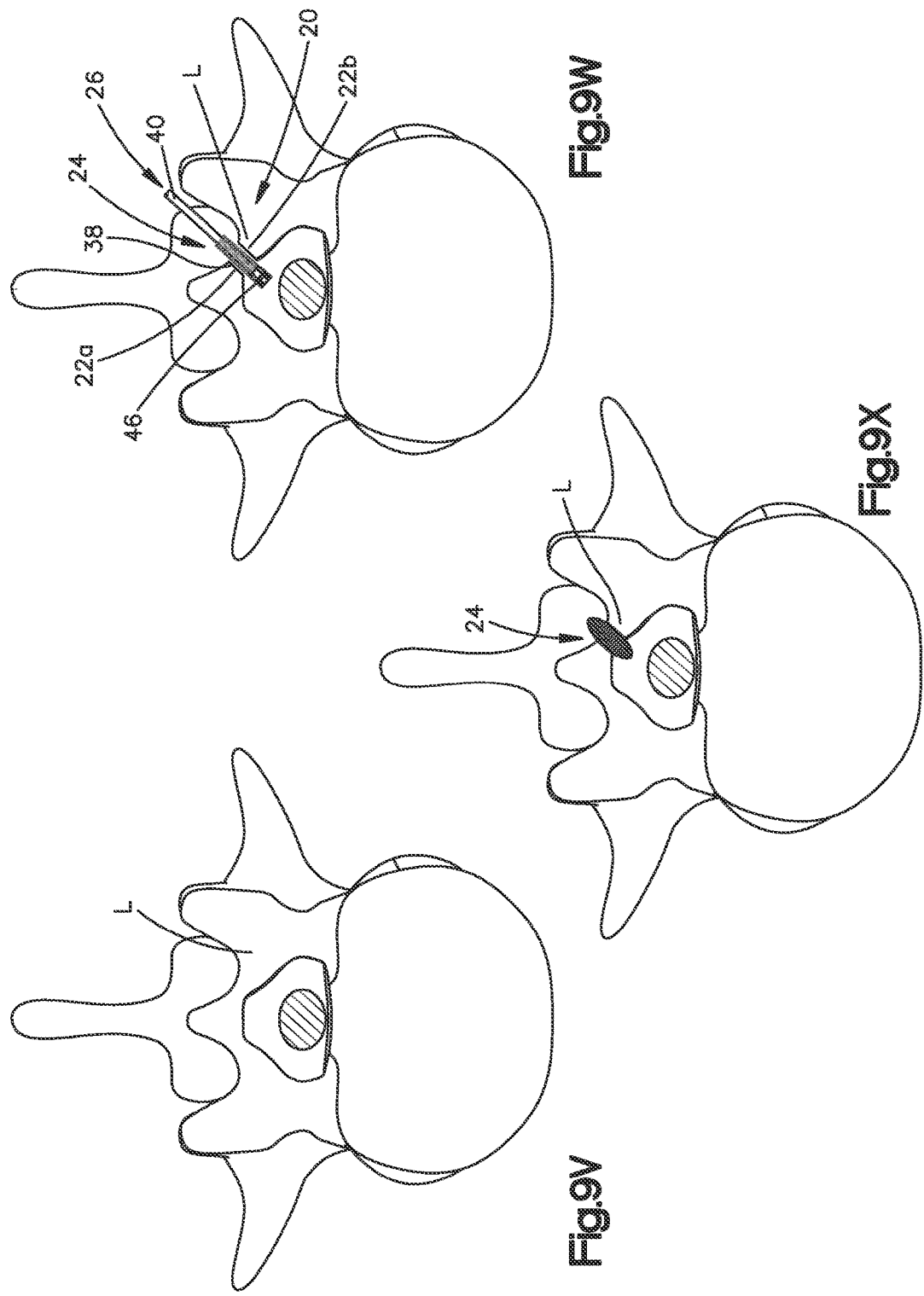

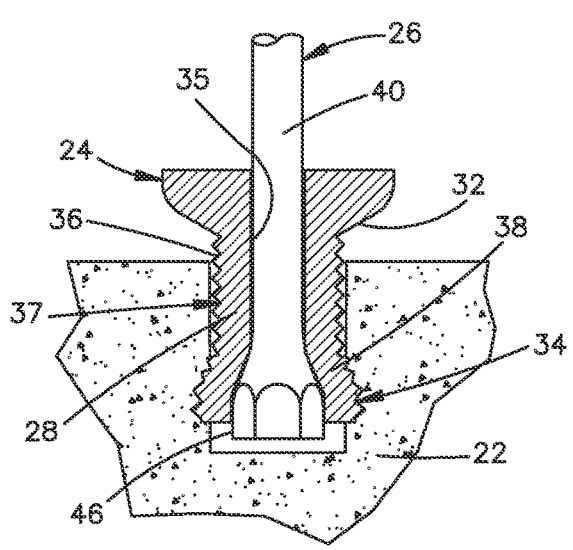
Fig.10A
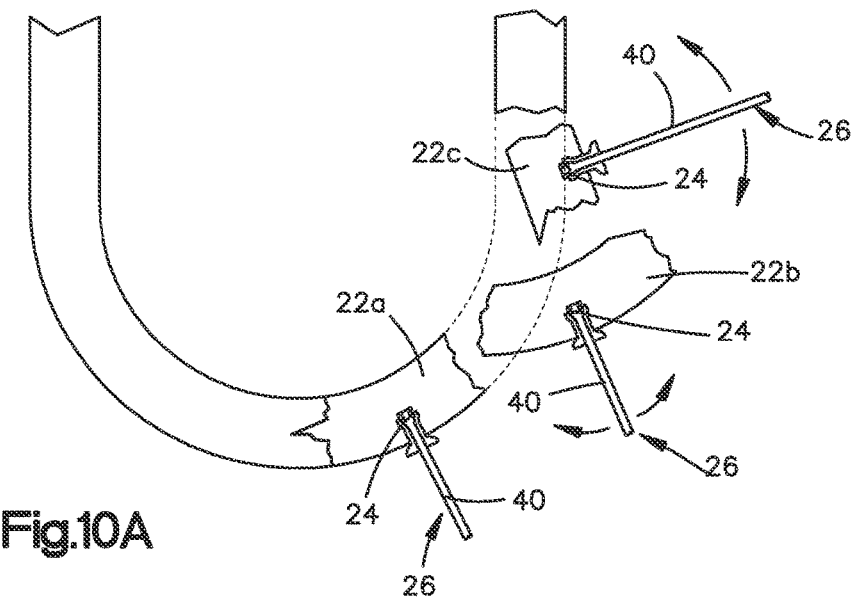
Fig.10B
Fig.11A
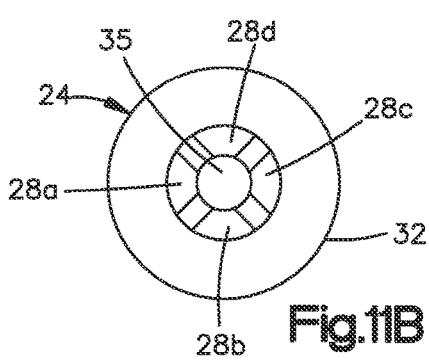
Fig.11B

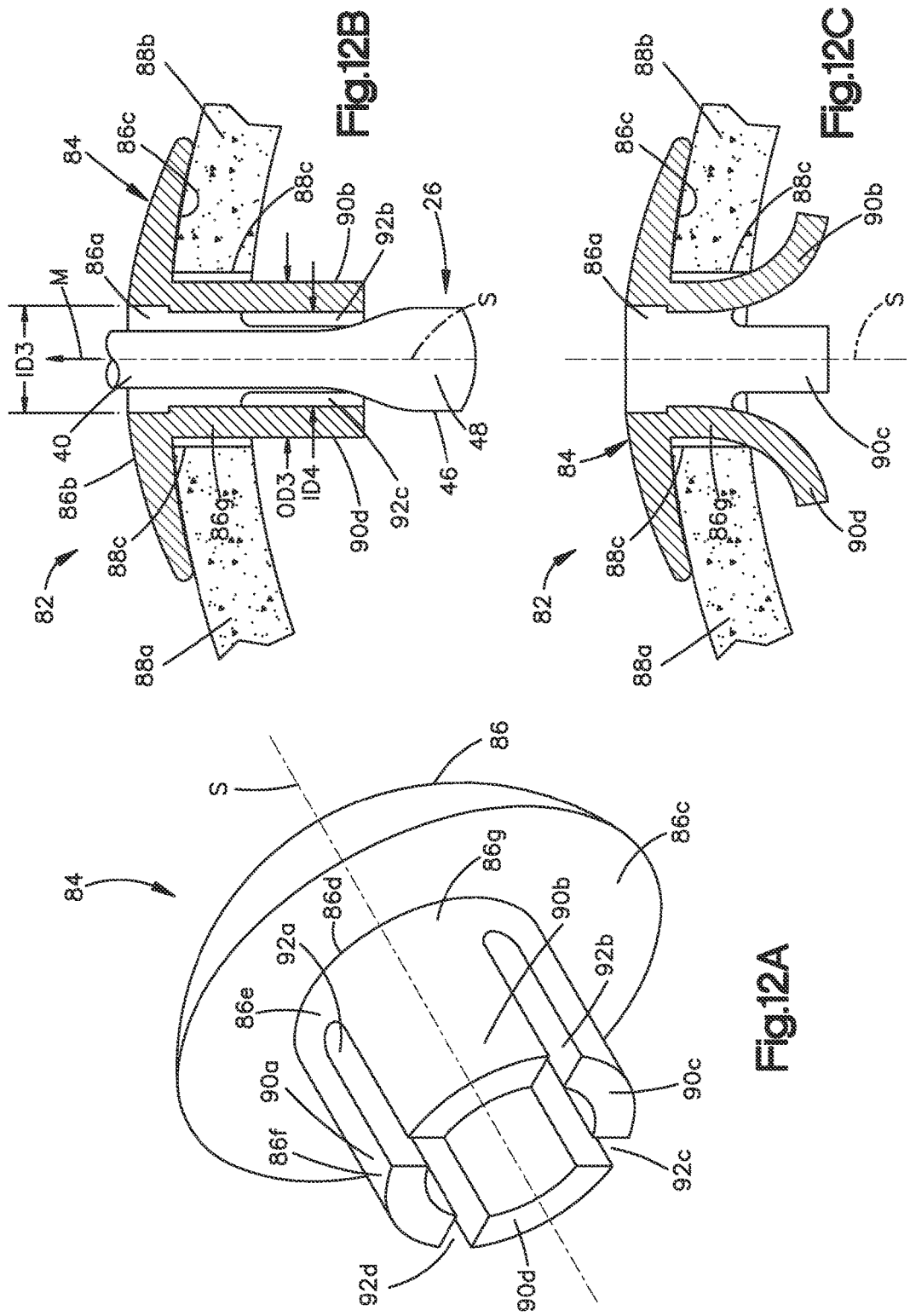

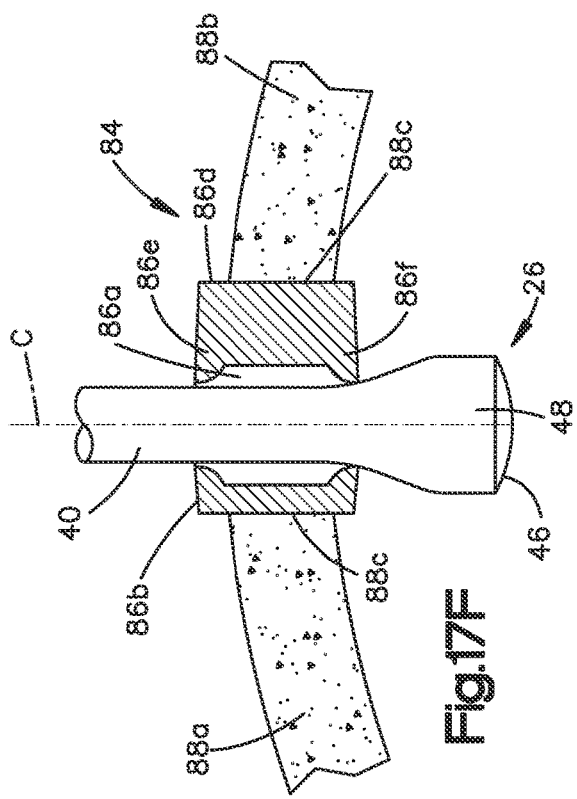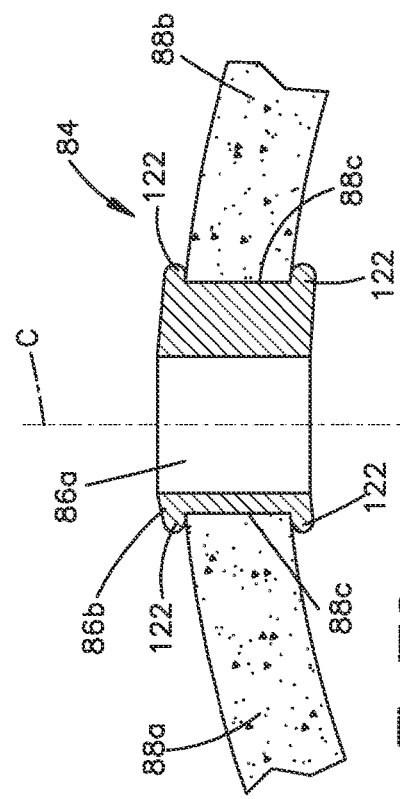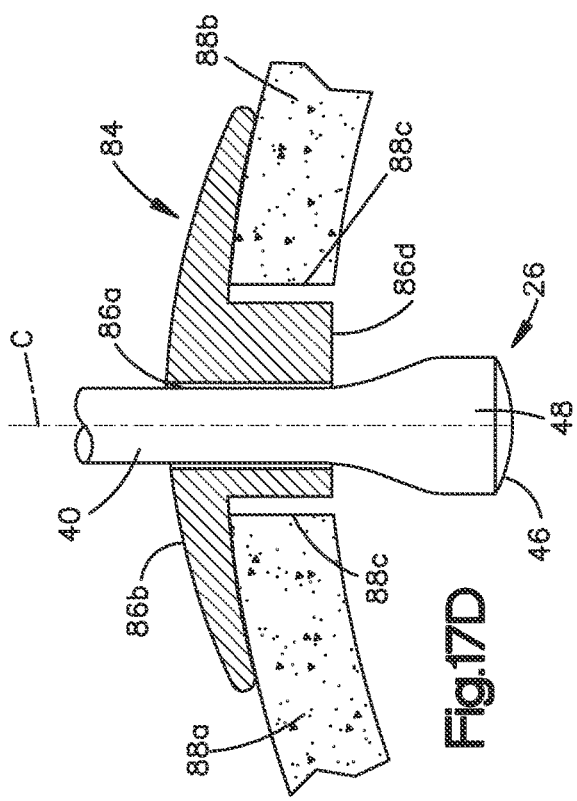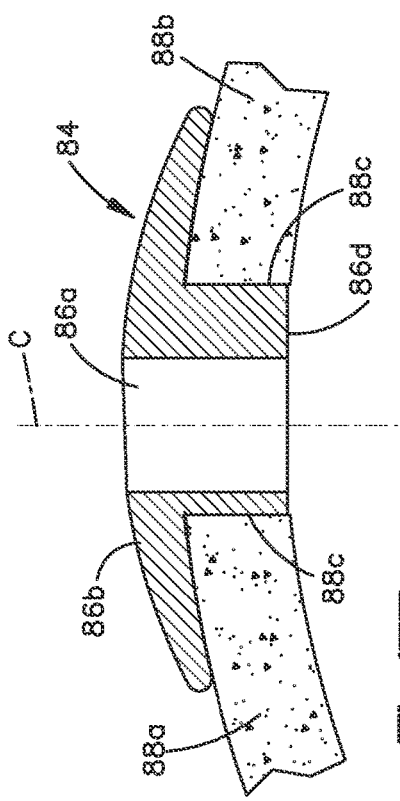

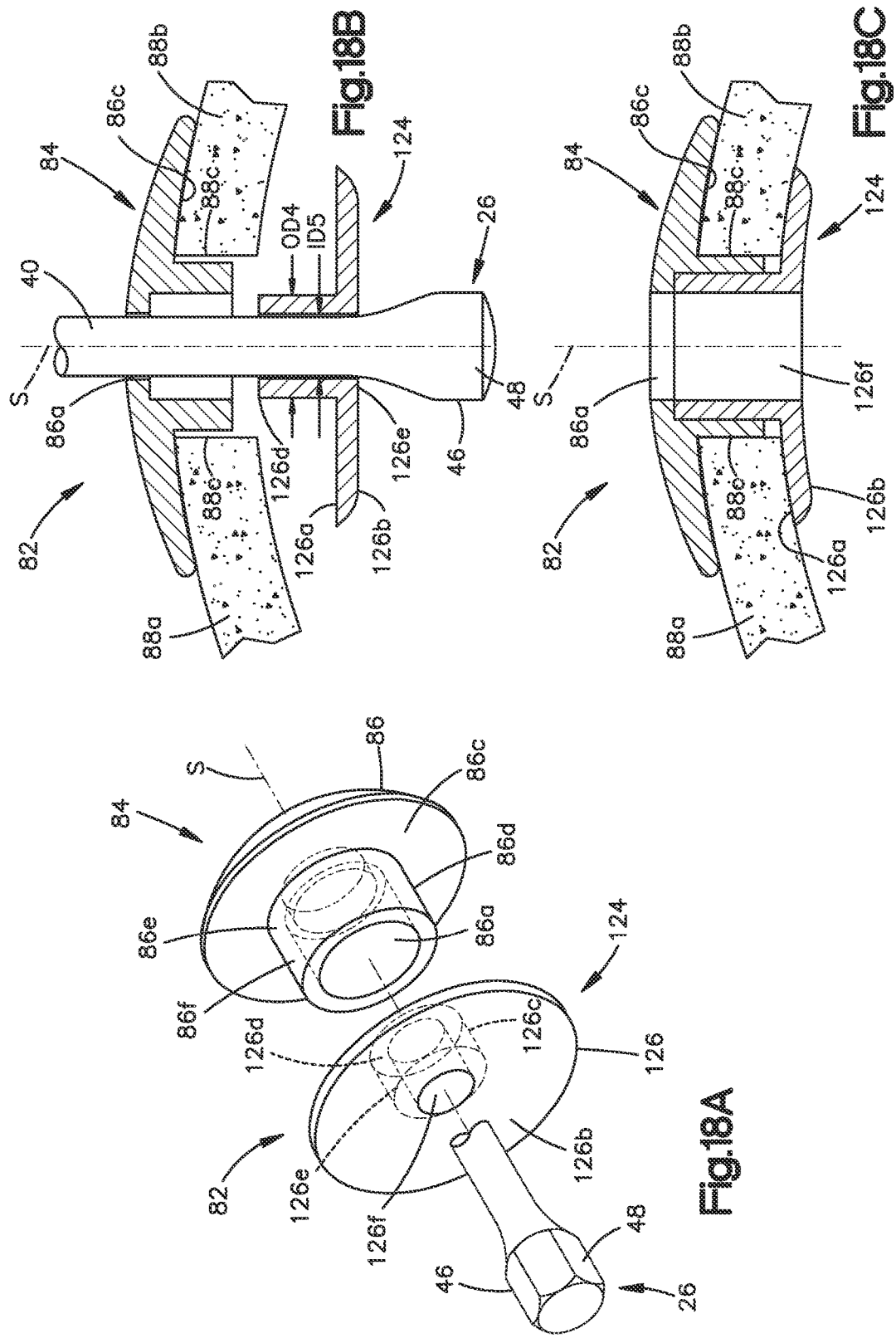

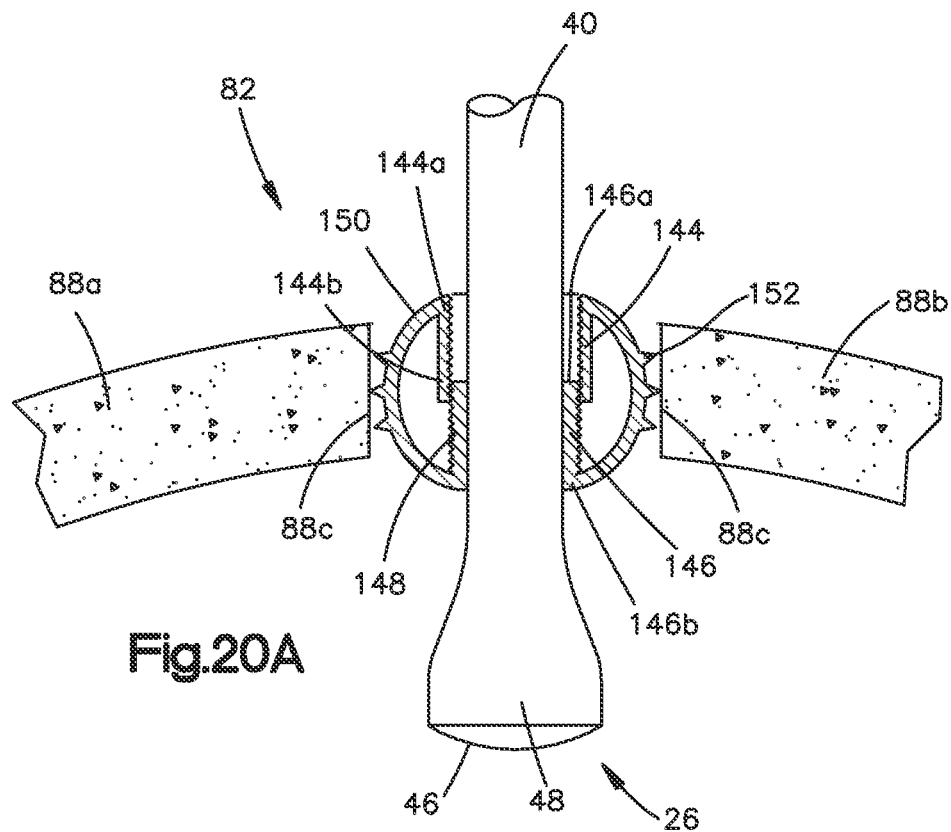
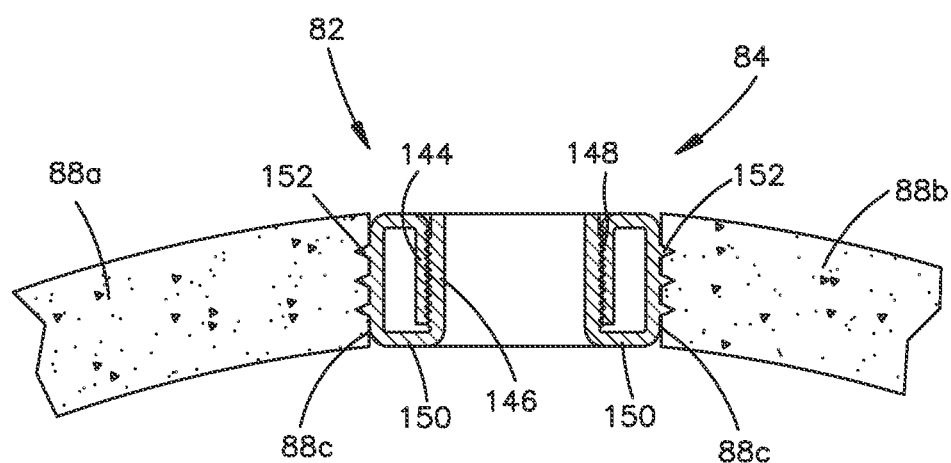

EXPANDABLE FIXATION ASSEMBLIES

CROSS-REFERENCE TO RELATED APPLICATIONS

This patent application is a divisional application of U.S. patent application Ser. No. 12/831,144, filed Jul. 6, 2010, which claims the benefit of U.S. provisional patent application No. 61/223,261, filed Jul. 6, 2009, the teachings of all of which are incorporated herein by reference in their entirety.

TECHNICAL FIELD

The present disclosure relates generally to fixation members, and in particular to expandable fixation members for fastening a structure to bone and/or for securing bone segments.

BACKGROUND

Bone screws are commonly used to fix adjacent bones or bone fragments with respect to each other, or to attach structure to bone. For example, bone screws are commonly used to help repair fractures in bone, to attach bone plates to bone, to fix adjacent vertebral bodies, and so on.

However, typical bone screws and conventional methods of bone screw insertion can introduce undesirable complications in such procedures. For example, conventional methods of bone screw insertion can lead to: small and/or mobile bone fragments dislocating from the bone or bone segment due to axial pressure and insertion torque transmission during screw insertion; screw loss during operation (including transporting the screw from its storage place to final fixation location in the patient); shear off and cam out of the screw head during screw insertion and/or removal; slipping between the screw driver interface and the screw driver; stripping of the screw driver interface; bone milling during rotational insertion of self drilling and/or self tapping screws; misalignment of the pre-drilled holes in adjacent bone fragments and/or bone plates which can lead to secondary dislocation and inaccurate positioning of the bone fragments and/or bone plate; suboptimal screw fixation due to angular misalignment of a pre-drilled pilot hole's axis and the desirable screw insertion axis; and post operative back out of screws. Furthermore, when conventional bone screws are used to attach small bone segments that have little structural support, the axial and rotational force required to start a screw into such small fragments can be such that the fragment becomes dislocated. Additionally, when it is desirable to use a long bone screw, driving the screw into bone can become laborious.

Additional complications of using typical bone screws and conventional methods of bone screw insertion can be introduced by the sheer number of steps, and associated opportunities to introduce errors, required in a given procedure. For instance, in the case of a bone fracture, FIG. 1A illustrates a conventional bone lag screw 10 with a partially threaded shaft that is used to join two fractured bone segments 11a and 11b. Unfortunately, performing this procedure with the use of conventional bone screws is complex and involves a number of steps. First, the surgeon reduces the fracture, and then drills a first hole 12 into the first bone segment 11a, such that the first hole 12 has a diameter $_1$ equal to the major diameter of the screw 10. Next, the surgeon inserts a drill guide into the hole 12 and then drills a second hole 13 having a diameter $_2$ that is equal to the minor diameter of the screw 10. Once the two holes are drilled, the bone is countersunk for the head of the screw 10, the depth of the holes are measured to determine the length of screw needed, and finally the screw is inserted and threads 14 of the screw 10 are tightened into the second hole 13. FIG. 1B illustrates a procedure for similarly attaching a bone plate 11c to a bone segment 11d using a conventional bone screw 10 with a fully threaded shaft.

SUMMARY

An expandable bone fixation assembly including an expandable fixation member with an expandable shaft is provided. The expandable shaft has an axial bore of a first inner diameter extending therethrough along a bore axis that can be coincident with a central longitudinal axis of the shaft. The expandable shaft has a first external threaded section originating at the distal end of the shaft and extending towards the proximal end of the shaft along at least a portion of the shaft. The expandable fixation assembly also includes an expansion member having an elongate shaft with a mandrel at a distal end thereof. The elongate shaft is disposed within the bore of the expandable fixation member such that the mandrel is located at the distal end of the shaft. The mandrel has a beveled surface and an outer dimension that is greater than the first inner diameter of the shaft. When the mandrel is biased through the expandable shaft, the mandrel causes the expandable shaft to be biased radially outward and the threaded section of the shaft to engage with surrounding structure, such as bone.

BRIEF DESCRIPTION OF THE DRAWINGS

The foregoing summary, as well as the following detailed description of the preferred embodiments of the application, will be better understood when read in conjunction with the appended drawings. For the purposes of illustrating the expandable fixation assembly systems and methods, there are shown in the drawings preferred embodiments. It should be understood, however, that the instant application is not limited to the precise arrangements and/or instrumentalities illustrated in the drawings, in which:

FIG. 2D is a sectional side elevation view of an expandable fixation assembly similar to that illustrated in FIGS. 2B-C, prior to expansion of the fixation member;

FIG. 2E is a sectional side elevation view of the expandable fixation assembly as illustrated in FIG. 2D after expansion of the fixation member;

FIG. 3A is a side elevation view of an expansion member in accordance with an embodiment;

FIG. 3B is a side elevation view of the expansion member illustrated in FIG. 3A in accordance with an alternative embodiment;

FIG. 3C is a perspective view of an expandable fixation assembly in accordance with an embodiment, prior to expansion of the expandable fixation member;

FIG. 3D is an end perspective view of the expandable fixation member of the expandable fixation assembly illustrated in FIG. 3C, prior to expansion of the expandable fixation member;

FIG. 3E is a side elevation view of the expandable fixation assembly illustrated in FIG. 3C, after partial expansion of the expandable fixation member;

FIG. 3F is an end perspective view of the expandable fixation member of the expandable fixation assembly illustrated in FIG. 3C, after expansion of the expandable fixation member;

FIG. 3G is a sectional side elevation view of the expandable fixation member of the expandable fixation assembly illustrated in FIG. 3C in accordance with an alternative embodiment, prior to expansion of the fixation member;

FIG. 3H is an end perspective view of the expandable fixation member illustrated in FIG. 3G, prior to expansion of the expandable fixation member;

FIG. 3K is an end perspective view of the expandable fixation member illustrated in FIG. 3J, prior to expansion of the expandable fixation member;

FIG. 3L is a side elevation view of the expandable fixation member illustrated in FIG. 3J, after expansion of the expandable fixation member;

FIG. 4A shows an expandable fixation assembly including an expandable fixation member having self-drilling flutes constructed in accordance with an embodiment;

FIG. 4B shows a self-drilling expandable fixation assembly including an expandable fixation member having self-drilling flutes constructed in accordance with an alternative embodiment;

FIG. 4C shows an anchoring geometry of the self-tapping flutes in the direction of rearward movement with a conical runout of the threads;

FIG. 6C is a sectional side elevation view of an expandable fixation assembly including an alternative expansion member in accordance with an embodiment;

FIG. 7A is a sectional side elevation view of an expandable fixation member having a head configured for angulation;

FIG. 7B is a sectional side elevation view of a portion of the expandable fixation member illustrated in FIG. 7A;

FIG. 7C is a sectional side elevation view of the expandable fixation member illustrated in FIG. 7A in accordance with an alternative embodiment;

FIG. 7D is a sectional side elevation view of the expandable fixation member illustrated in FIG. 7A in accordance with another alternative embodiment;

FIG. 7E is a sectional side elevation view of the expandable fixation member illustrated in FIG. 7A in accordance with still an alternative embodiment;

FIG. 7F is a is a sectional side elevation view of a portion of the expandable fixation member illustrated in FIG. 7E;

FIG. 8 is a sectional side elevation view of an expandable fixation member having anchoring geometry configured to prevent screw loosening and/or migration in accordance with an embodiment;

FIG. 9D is a side elevation view of the expandable fixation member illustrated in FIGS. 9A-C in accordance with an alternative embodiment;

FIG. 9E is a sectional side elevation view of the expandable fixation member illustrated in FIG. 9D;

FIGS. 9J-O are elevation views of expandable fixation assemblies used in adjacent vertebral bodies in accordance with various spinal fixation embodiments;

FIG. 9P is a side elevation view of a pair of expandable fixation assemblies inserted into an interspinous spacer assembly in accordance with an embodiment;

FIG. 9Q is a rear partially exploded elevation view of the interspinous spacer assembly illustrated in FIG. 9P;

FIGS. 9V-X are top elevation views of an expandable fixation member inserted into a space within a lamina of a vertebral body and expanded, in accordance with an embodiment;

FIGS. 10A-B are sectional elevation views of expandable fixation assemblies that are partially expanded within respective bone segments in accordance with an embodiment;

FIG. 11A is a side elevation view of an expandable fixation member having a shaft separated into a plurality of legs in accordance an embodiment;

FIG. 11B is a bottom elevation view of the expandable fixation member illustrated in FIG. 11A;

FIG. 12A is a perspective view of an expandable cranial fixation member in accordance with an embodiment;

FIG. 12B is a sectional elevation view of an expandable cranial fixation assembly including the expandable cranial fixation member illustrated in FIG. 12A, prior to expansion of the expandable cranial fixation member;

FIG. 12C is a sectional elevation view of the expandable cranial fixation assembly illustrated in FIG. 12B, after expansion of the expandable cranial fixation member;

FIG. 17D is a sectional elevation view of the expandable cranial fixation assembly illustrated in FIG. 17A, prior to expansion of the expandable cranial fixation member;

FIG. 17E is a sectional elevation view of the expandable cranial fixation assembly illustrated in FIG. 17D, after expansion of the expandable cranial fixation member;

FIG. 17F is a sectional elevation view of the expandable cranial fixation assembly illustrated in FIG. 17A in accordance with an alternative embodiment, prior to expansion of the expandable cranial fixation member;

FIG. 17G is a sectional elevation view of the expandable cranial fixation assembly illustrated in FIG. 17F, after expansion of the expandable cranial fixation member;

FIG. 18A is an exploded perspective view of an expandable cranial fixation assembly in accordance with an alternative embodiment;

FIG. 18B is a sectional elevation view of the expandable cranial fixation assembly illustrated in FIG. 18A, prior to expansion of the expandable cranial fixation member;

FIG. 18C is a sectional elevation view of the expandable cranial fixation assembly illustrated in FIG. 18B, after expansion of the expandable cranial fixation member;

FIG. 20A is a sectional elevation view of an expandable cranial fixation assembly in accordance with an alternative embodiment, prior to expansion of the expandable cranial fixation member;

FIG. 20B is a sectional elevation view of the expandable cranial fixation assembly illustrated in FIG. 20A, after expansion of the expandable cranial fixation member;

DETAILED DESCRIPTION

Figure 2A:
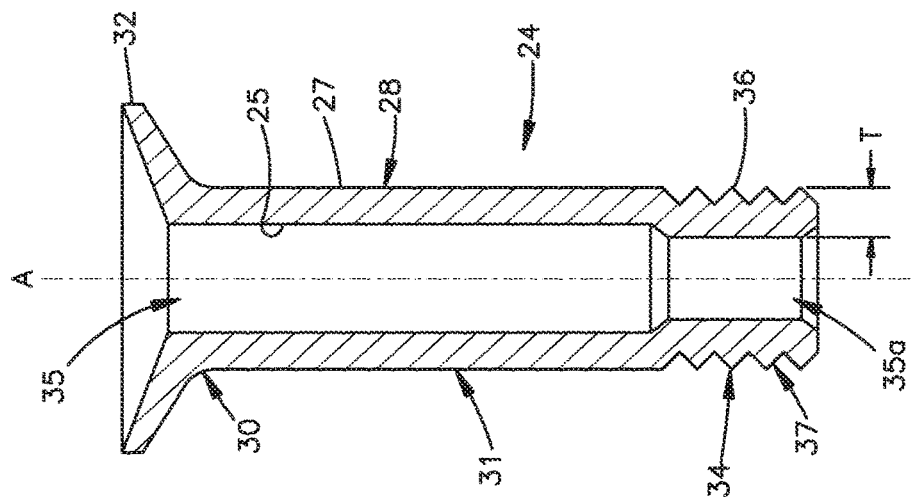
FIG. 2A is a sectional side elevation view of an expandable fixation member that forms part of an expandable fixation assembly in accordance with an embodiment.
Figure 1B:
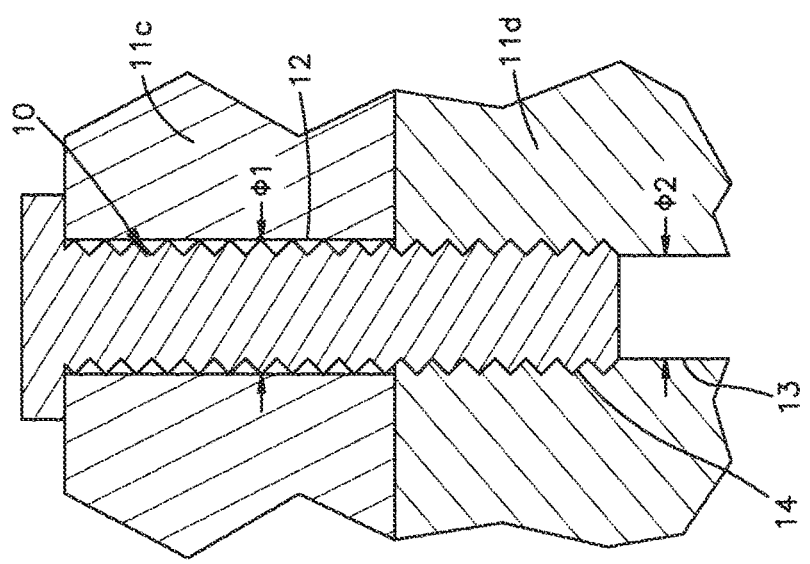
FIG. 1B is a schematic illustration of a conventional bone screw with a fully threaded shaft joining a bone plate and a bone segment together.
Figure 1A:
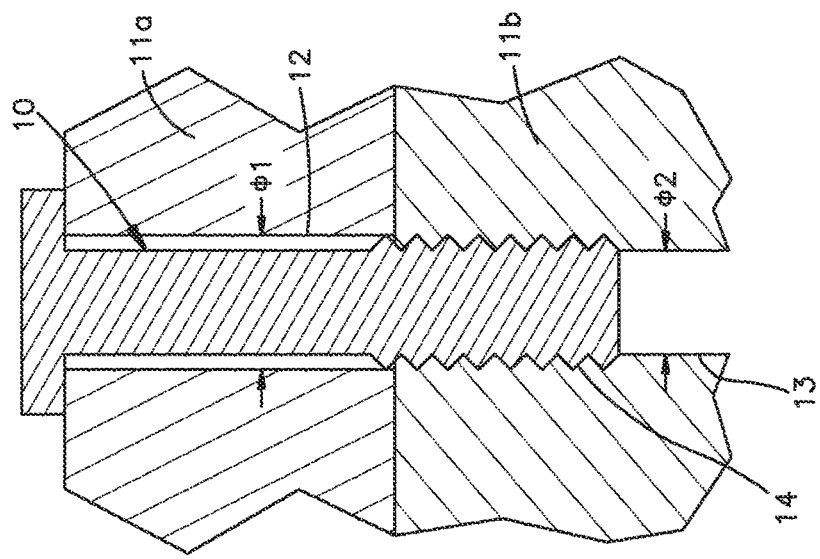
FIG. 1A is a schematic illustration of a conventional bone screw with a partially threaded shaft joining two bone segments together.

For convenience, the same or equivalent elements in the various embodiments illustrated in the drawings have been identified with the same reference numerals. Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior", "lateral", "medial", "sagittal", "axial", "coronal," "cranial," "caudal" and related words and/or phrases designate preferred positions and orientations in the human body to which reference is made and are not meant to be limiting. The words "vertebral body" as used herein should be interpreted broadly to include all the bones and bony structures found within and in the immediate proximity of the human spinal system, including but not limited to those found in the cervical region, the thoracic region, the lumbar region, and the sacral curve region. The words "bias," "biased," and "biasing" refer to causing the object being referred to, and designated parts thereof, to change position, for example by pushing, pulling, drawing, or otherwise applying force thereto. The terminology intended to be non-limiting includes the above-listed words, derivatives thereof and words of similar import.

Figure 2B:
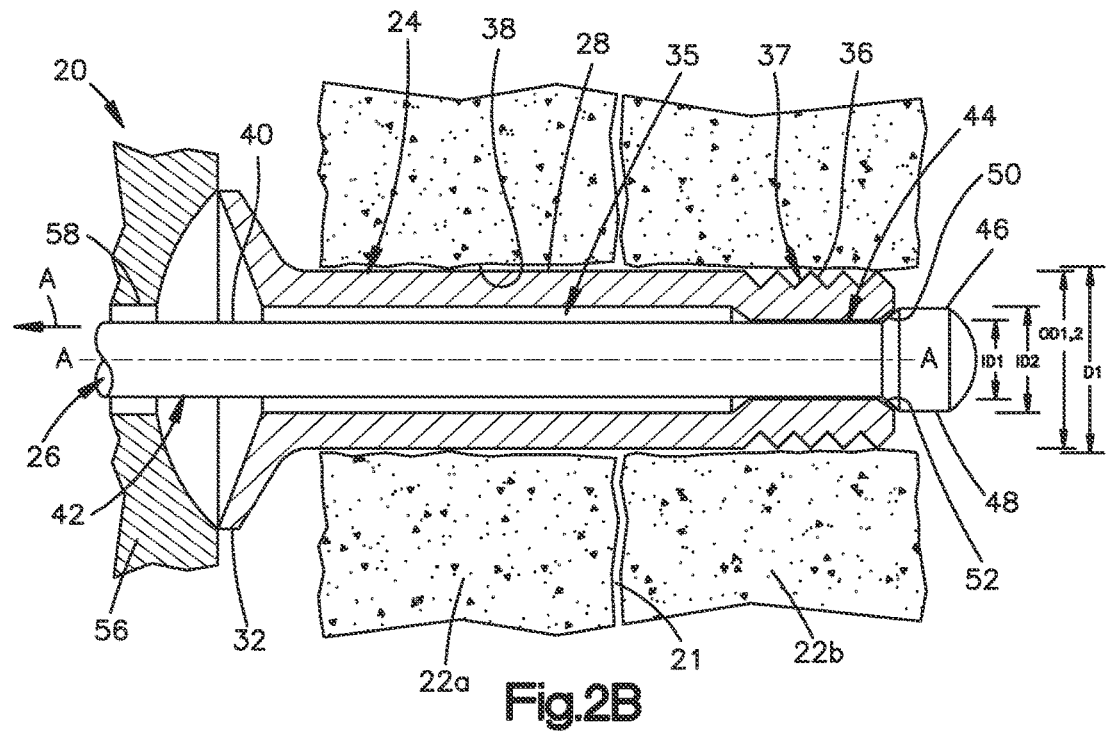
FIG. 2B is a sectional side elevation view of the expandable fixation assembly illustrated in FIG. 2A, including an expansion member, prior to expansion of the fixation member.

Referring now to FIGS. 2A-B, an expandable bone fixation assembly 20 includes an anchoring region 37 that can include engagement structures, such as threads 36 or any alternative external geometry, configured to fasten an expandable fixation member 24 to one or more surrounding structures that are to be joined, such as bone segments 22a-b that have been separated by a fracture 21. It should be appreciated that reference herein to threads includes a reference to any suitable external geometry capable of fastening the expandable fixation member 24 to one or more surrounding structures, such as bones and/or bone segments. The expandable fixation assembly 20 can alternatively fasten any desired alternative structure to a bone and/or bone segment, for example an orthopedic screw, a bone anchor for soft tissue and/or ligament fixation, a prosthesis, a nail, a rod, an external fixation member, and the like.

While the mandible is one example of a bone whose fractured segments are joinable with the expandable fixation assembly 20, the application of the expandable fixation assembly 20 is not intended to be limited thereto, and is contemplated for use in conjunction with any suitable bones, bone segments, and/or in combination with bone on-lay or other tissue and osteosynthesis devices and/or materials, bone grafts, bone graft substitutes such as synthetics, or bone substitutes. Two such bones and/or bone segments are referred to herein as bone segments 22a and 22b. In the illustrated embodiment, the bone segment 22a is referred to as an outer bone segment and the bone segment 22b is referred to as an inner bone segment. While the fixation assembly 20 is illustrated as directly fastening the bone segments 22a-b together, it should be appreciated that the fixation assembly 20 can alternatively be used to fasten bone plates, grafts and/or other devices to an exterior surface of a bone and/or bone segment, and/or to fasten bone plates to bone grafts.

The expandable fixation assembly 20 includes the expandable fixation member 24, which can be provided as a bone screw, a rivet screw, or the like, and an expansion member 26 that is configured to expand the fixation member 24 so as to secure a portion of the fixation member 24 that includes anchoring geometry, such as the threads 36 or any other suitable exterior geometric structure, to surrounding structure, such as the inner bone segment 22b.

The fixation member 24, and other components of the various expandable fixation assemblies described herein, can be made from any suitable biocompatible and/or resorbable materials and/or alloys (e.g., Ti alloy, TiCP, magnesium, stainless steel, plastics, polymers, etc.) which provide ductility for radial expansion as well as the stability to withstand the indication-specific, applied forces. The expansion member 26 can be made of any suitable medical grade and/or biocompatible material (e.g., instrument grade stainless steel or cobalt chrome) that is sufficiently strong to expand the fixation member 24 and be biocompatible. It is further desirable that the material allow for the expansion member 26 to be fully drawn through the fixation member 24 and removed therefrom. If a portion of the expansion member 26 is to be left in the fixation member 24, like in a traditional rivet, then an implantable grade material would be desirable for the expansion member 26. In one embodiment, the fixation member 24 is made from a titanium alloy, and the expansion member 26 (specifically the mandrel 46 described below) is made from a titanium alloy or cobalt chrome.

The fixation member 24, as depicted in FIG. 2A, includes a cannulated, or annular, shaft 28 that presents radially opposing inner and outer surfaces 25 and 27, respectively. The fixation member 24 is axially elongate along central longitudinal axis A-A. The shaft 28 defines a proximal end 30 that includes a head 32 and/or a second thread and/or anchoring geometry, an opposing distal end 34, and an intermediate portion 31 disposed between the proximal and distal ends 30 and 34. The shaft 28 can be provided as a screw shaft, and the head 32 can be provided as a screw head when the fixation member 24 is provided as a bone screw. The shaft 28 defines one or more internal axial bores, for example bores 35 and 35a, formed along a bore axis that is coincident with the axis A-A, the bores extending through the head 32 and through the entirety of the shaft 28. The fixation member 24 further includes one or more anchoring regions 37, the anchoring regions 37 in radial alignment with the bore 35 and having anchoring geometry formed thereon, such as helical threads 36 that extend radially outward from the outer surface of the distal end 34 of the shaft 28. Of course the anchoring geometry is not limited to threads, and can assume any suitable size and shape capable of biting into or otherwise engaging the bone segment 22b once the fixation member 24 has been radially expanded. The remaining portion of the outer surface of the shaft 28 is smooth, or unthreaded, though this portion could be fully or partially threaded and/or otherwise shaped to include any suitable alternative anchoring geometry as desired.

In the illustrated embodiment, the distal end 34 of the shaft 28 defines an inner diameter ID1 that is less than the inner diameter ID2 of both the intermediate portion 31 and the proximal end 30 prior to radial expansion of the fixation member 24, though it should be appreciated that the inner diameter ID1 can assume any desired relationship with respect to the remainder of the fixation member 24 such that the distal end 34 is configured to radially expand in the manner described below. The outer diameter OD1 of the distal end 34 of the shaft 28 can be equal to, greater than, or less than, the outer diameter OD2 of the middle portion 31 and the proximal end 30 of the shaft 28 prior to radial expansion of the fixation member 24. In the illustrated embodiment, the outer diameter OD1 is substantially equal to the outer diameter OD2. Furthermore, in the illustrated embodiment, the wall of the shaft 28 has a thickness T that, at the distal end 34, can be greater than, lesser than, or equivalent to the thickness T of the shaft 28 in the middle portion 31 or at the proximal end 30. It should be appreciated that the term "diameter" as used herein applies to not only round objects in the traditional sense, but is also intended to describe width dimensions (i.e., an "outer dimension") for non-round objects, as measured in a cross-sectional fashion at the points of their greatest width.

Referring now to FIG. 2B, a bore 38 is drilled in the bone segments 22a-b prior to insertion of the fixation member 24. It should be appreciated that the terms "inner" and "outer" with respect to the axial direction are used with respect to a direction into and out of the bore 38, respectively. The bore 38 has a diameter, or cross-sectional dimension, D1 that is equal to or greater than the outer diameter OD1 of the distal end 34 of the shaft 28 prior to expansion of the fixation member 24. Thus, the fixation member 24 can be inserted axially into the bore 38 such that the head 32 abuts the outer surface of an outer structure, such as a bone, a ligament, an osteosynthesis device such a plate or a hole therein, and the like. In the illustrated embodiment, the outer structure is bone segment 22a. Prior to radial expansion of the fixation member 24, the fixation member 24 is loosely received in the bore 38 such that the threads 36 are aligned with the inner bone segment 22b.

The expansion member 26 includes an axially elongate shaft 40 having a proximal end 42 and an opposing distal end 44. The shaft 40 can be defined by a plurality of outer diameters along its length. The distal end 44 of the shaft 40 is coupled to a mandrel 46 that has an outer radial surface 48 that can be round, such that the mandrel 46 is substantially spherical or ball-shaped. It should be appreciated that the mandrel 46 can be assume any alternative suitable shape such that a diameter or other outer dimension of the outer radial surface 48 is greater than the inner diameter ID1 of the distal end 34 of the shaft 28 and/or any other internal portion of the shaft 28 that is to be expanded. In the illustrated embodiment, the outer radial surface 48 has an outer dimension that is substantially equal to the inner diameter ID2 of the middle portion 31 and the proximal end 30 of the shaft 28. The outer radial surface 48 can further include a beveled surface 50 that provides a transitional interface between the distal end 44 of the shaft 40 and the region of the outer radial surface 48 having the greatest dimension. The angle, or rake, of the beveled surface 50 may be configured to draw, or broach, material from the inner surface 25 of the shaft 28 as the mandrel is pulled therethrough. Generally, as the angle of the beveled surface with respect to the shaft 40 increases, an increasing amount of material may be drawn through the shaft 82. Broaching of the shaft 28 by the mandrel 46 may act to decrease the amount of force needed to bias the mandrel 46 through the shaft 28. Broaching may also be achieved when the mandrel 46 is pushed into the shaft 28, as discussed in more detail below. The amount of material that is broached, and thereby the amount of force required to bias the mandrel 46 through the shaft 28, can be tailored by varying characteristics of the fixation member 24 and/or the expansion member 26, such as the material of the fixation member 24 and/or the expansion member 26, the thickness T of the shaft 28, the rake/angle of the beveled surface 50, and the like. The distal end 34 of the shaft 28 can be configured with a complimentary beveled surface 52 that is configured to engage the beveled surface 50 of the mandrel 46, as depicted in FIG. 2B. One or more additional bevels can be formed within the shaft 28, for example to act as diameter expansion and/or retraction transitions, as a stop, a limitation, and the like.

Figure 2C:
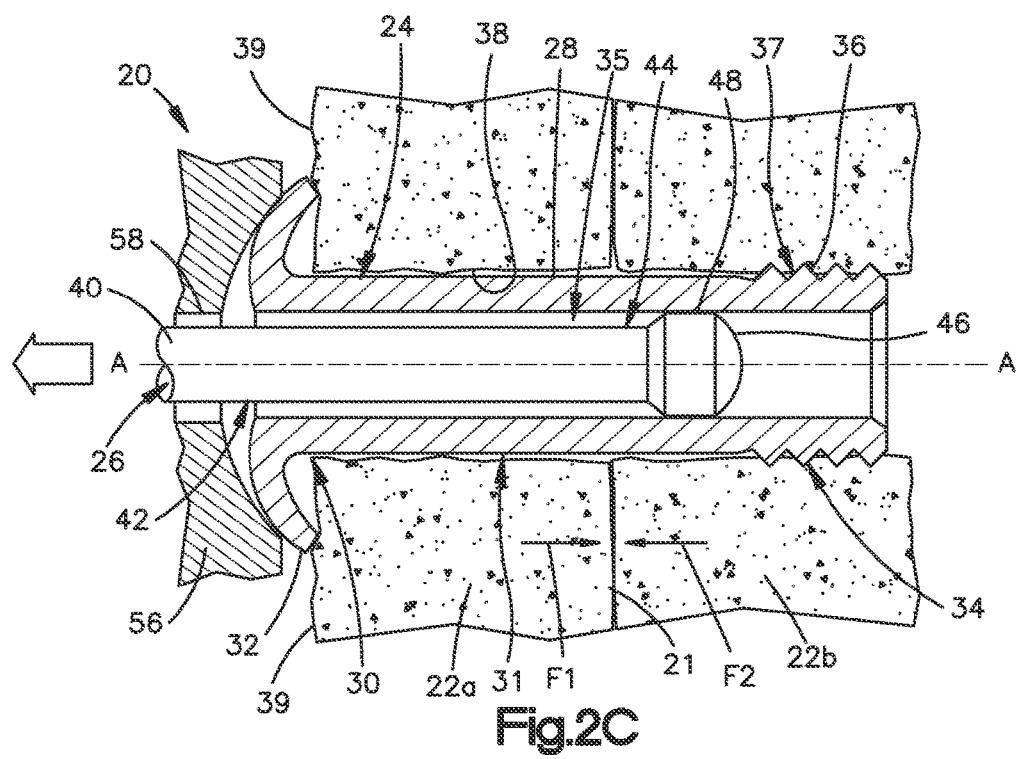
FIG. 2C is a sectional side elevation view of the expandable fixation assembly illustrated in FIG. 2B after expansion of the fixation member.

Referring now also to FIG. 2C, it should be appreciated that the expansion member 26 is typically pre-installed in the fixation member 24 prior to inserting the fixation member 24 into the bore 38 of the bone segments 22a-b. In particular, the shaft 40 of the expansion member 26 is received in the bore 35 of the fixation member 24, and the mandrel 46 is disposed external to the shaft 28 at a location axially inward from the distal end 34. Once the fixation member 24 and the expansion member 26 have been installed into the bore 38, a brace 56 can be placed against the outer surface of the head 32. The brace 56 can define an inner bore 58 that has a diameter or alternative cross-sectional dimension that is greater than the outer diameters of the shaft 40 of the expansion member 26 and mandrel 46 such that the shaft 40 and the mandrel 46 can be received in the bore 58. Once the brace 56 is placed in position, the expansion member 26 can be pulled through the shaft 28 of the fixation member 24 while the brace 56 bears against the head 32 to provide a reciprocal axial force against the force created by the expansion member 26 as it is pulled through the shaft 28 of the fixation member 24.

Referring now to FIGS. 2D and 2E, the illustrated fixation assembly 20 is similar to that illustrated in FIGS. 2B-C, however the entire length of the shaft 28 of the fixation member 24 is expandable when the expansion member 26 is drawn through the shaft 28. Only the anchoring region 37 at the distal end 34 of the shaft 28 includes anchoring geometry, such as the threads 36. The shaft 28 will only radially expand to the inner diameter of the bore 38 it is inserted into. This allows a mandrel 46 having a non cylindrical shape, as described below with reference to FIGS. 3A-3L, to be drawn through the length of the shaft 28 of the fixation member 24, thereby creating a drive recess in the shaft 28. The drive recess allows engagement of a tool that is inserted into the fixation member 24 for removal from, or tightening of, the fixation member 24 with respect to the bore 38.

As the expansion member 26 is pulled into the distal end 34 of the shaft 28 of the fixation member 24, the beveled surface 50 of the mandrel 46 interferes with the beveled surface 52, thereby biasing the distal end 34 of the shaft 28 radially outward. Thus, as the mandrel 46 is pulled through the distal end 34, the outer radial surface 48 of the mandrel 46 biases the threads 36 into the surrounding structure of the inner bone segment 22b, thereby fastening the distal end 34 of the shaft 28 to the bone segment 22b. Furthermore, the brace 56 applies a force to the head 32 of the shaft 28 that can cause the head 32 to bend, or otherwise deform, for example in a distal direction, into the outer surface 39 of the bone segment 22a, thereby capturing the bone segment 22a between the head 32 of the shaft 28 and the bone segment 22b. As a result, the brace 56 could cause compressive forces F1 and F2 to be imparted onto the bone segments 22a-b, causing the bone segments 22a-b to be drawn together, thereby closing the fracture 21. Once the mandrel 46 has advanced past the distal end 34 of the shaft 28, it may be easily pulled through the middle portion 31 and the proximal end 30 and out of the fixation member 24. The brace 56 can be removed.

The contour of the outer surface of the fixation member 24 after it has been expanded depends on the shape of the outer radial surface 48 of the mandrel 46 of the expansion member 26 so that it is possible to change the contour of the outer surface of the expanded shaft 28 and not only the bore 35 during the activation process. For example, if a mandrel 46 with a hex shaped outer radial surface 48 is pulled through the shaft 28, the mandrel 46 may cause one or more axial lobular ridges to be formed on the outer surface of the fixation member 24, the lobular ridges corresponding with the intersection of the facets of the hex shaped outer radial surface 48 of the mandrel 46 and the inner surface 25 of the fixation member 24.

Figure 2F:
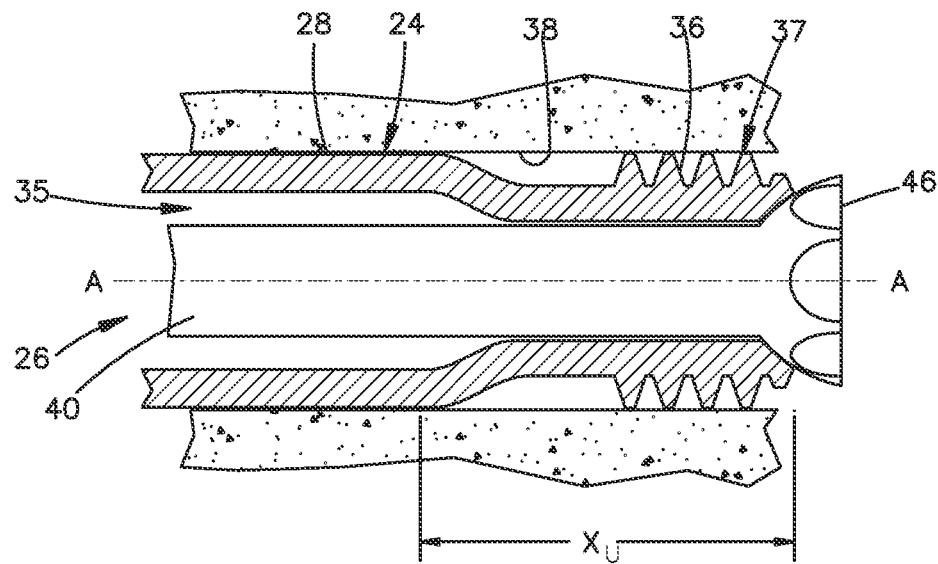
FIG. 2F is a sectional side elevation view of a portion of the fixation member illustrated in FIG. 2A in accordance with another embodiment, prior to expansion of the fixation member.
Figure 2G:
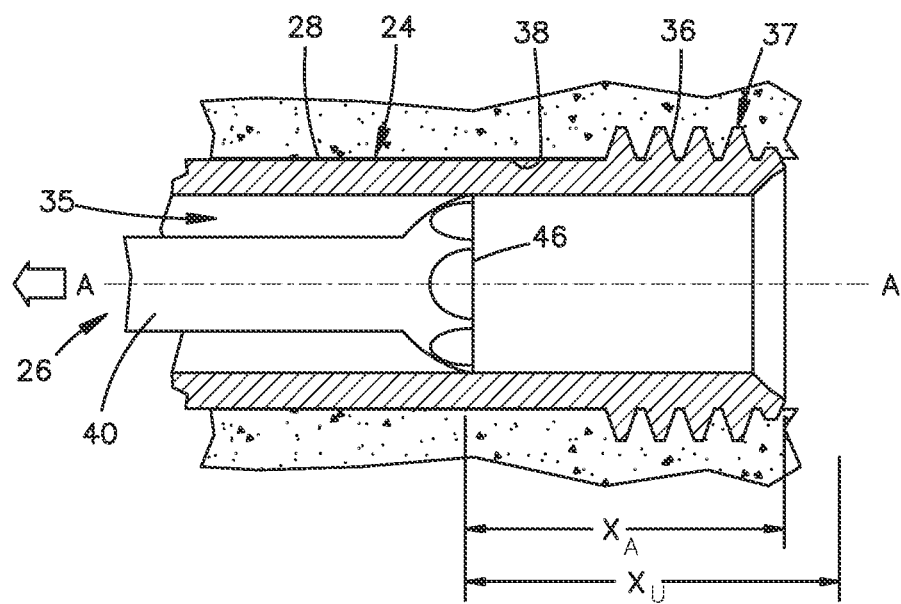
FIG. 2G is a sectional side elevation view of a portion of the fixation member illustrated in FIG. 2F, after expansion of the fixation member.

Referring now to FIG. 2F-G, it should be appreciated that the shaft 28 presents an anchoring geometry, such as the threads 36 and/or a combination of threaded and unthreaded sections within an expandable region, or activation zone $X_U$, of the shaft 28 that is configured to expand as the mandrel 46 is pulled through the bore 35. As the length of the activation zone $X_U$ increases, the axial force imparted onto the fixation member 24 by the mandrel 46 and the corresponding reciprocal axial force imparted onto the head 32 by the brace 56 creates an increasing compressive force onto the bone segments 22a-b that closes the fracture 21. It is possible to mitigate and/or to otherwise compensate for the increased compressive force by tapering the thickness T of the shaft 28 between the proximal and distal ends 30 and 34, respectively. As the mandrel 46 is pulled through the shaft 28, the portion of the shaft 28 within the activation zone $X_U$ may be compressed axially, resulting in a shortened activated activation zone $X_A$, and a reduced overall length of the fixation member 24. The amount of axial compression within the activation zone $X_U$ can be tailored by varying characteristics of the fixation assembly 20, for example the material of the fixation member 24 and/or the expansion member 26, the thickness T of the shaft 28, the geometry of the anchoring region 37, and the like. Once the resulting length of an activated activation zone $X_A$ is known, the overall length of the fixation member 24 can be designed so as to provide engagement by the expanded anchoring region 37 at varying depths, for example within the bore 38. Thus, a kit can be provided including a plurality of fixation members 24 having different length activation zones $X_U$ and/or overall lengths configured to provide varying levels of compressive forces and/or anchoring region 37 engagement depths that may be suitable for particular applications.

While the distal end 34 of the shaft 28 of the fixation member 24 can include an expandable region having external anchoring geometry, it should be appreciated that the shaft 28 of the fixation member 24 can alternatively have an expandable region having external anchoring geometry at any suitable location along its length, such that the expandable region is configured to engage the surrounding bone in the manner described herein. For instance, referring to FIG. 2H, the anchoring geometry of the fixation member 24, in particular the threads 36, extends along an entirety of the shaft 28 between the head 32 at the proximal end 30 and the distal end 34. The threads 36 can have a constant outer diameter, or one or more sections of varying outer diameters along the length of the shaft 28. As illustrated, the outer radial diameters of the threads 36 decrease in a direction from the proximal end 30 toward the distal end 34 of the shaft 28. Alternatively, the outer radial diameters of the threads 36 can increase in a direction from the proximal end 30 toward the distal end 34. Alternatively still, the outer radial diameters of the threads can increase or decrease from the proximal and/or distal ends 30 and 34 toward the middle portion 31 of the shaft 28. The outer diameters of the threads 36 can vary in any combination of the aforementioned.

Furthermore, while the inner diameter ID1 of the distal end 34 of the shaft 28 that includes anchoring geometry has been described as being less than the inner diameter ID2 of the middle portion 31 and the proximal end 30 of the shaft 28, the inner diameter ID1 of the distal end 34 of the shaft 28 can alternatively be substantially equal to the inner diameter ID2 of the remainder of the shaft 28, or even slightly larger than the inner diameter ID2 of the remainder of the shaft 28, so long as the outer dimension of the mandrel 46 is configured to bias a portion or all of the threads 36 of the anchoring region 37 radially outward, thereby causing the expanded threads 36 to bite into and grip, or otherwise engage or mate with, the surrounding structure of the bone segment 22b, alone or in combination with the bone segment 22a. It has been found that a fixation member 24 of the type described herein requires a larger pull-out force to pull the fixation member 24 out of the bore 38 than an identically constructed screw of non-expandable nature.

Figure 2I:
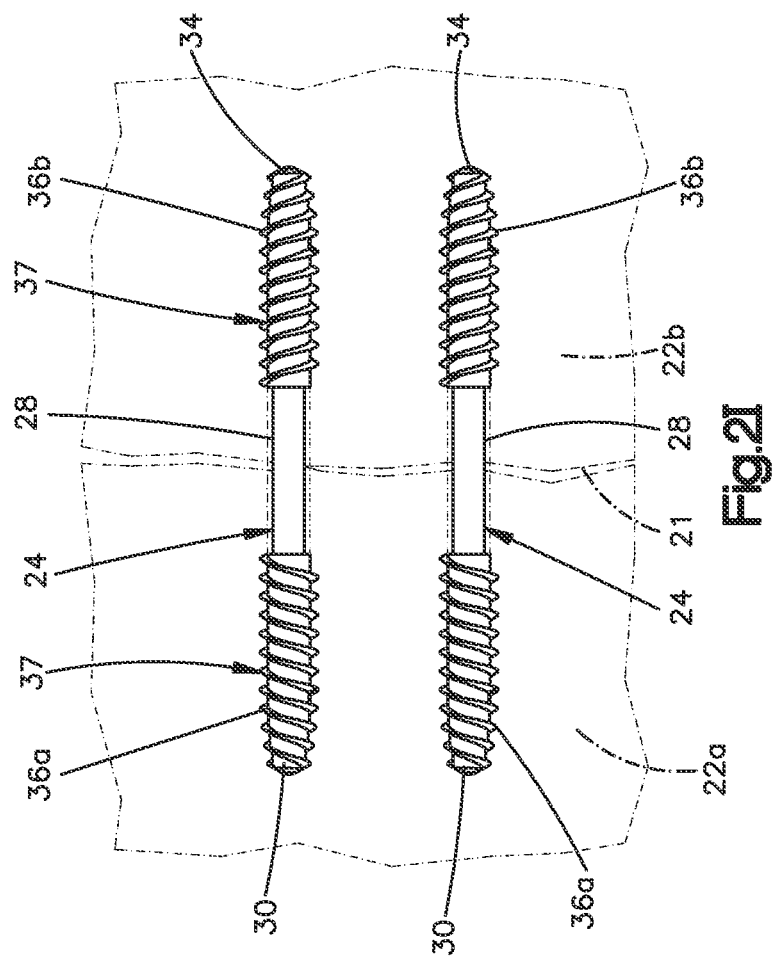
FIG. 2I is a schematic elevation view of an alternative expandable fixation assembly inserted between two bone segments separated by a fracture.
Figure 2H:
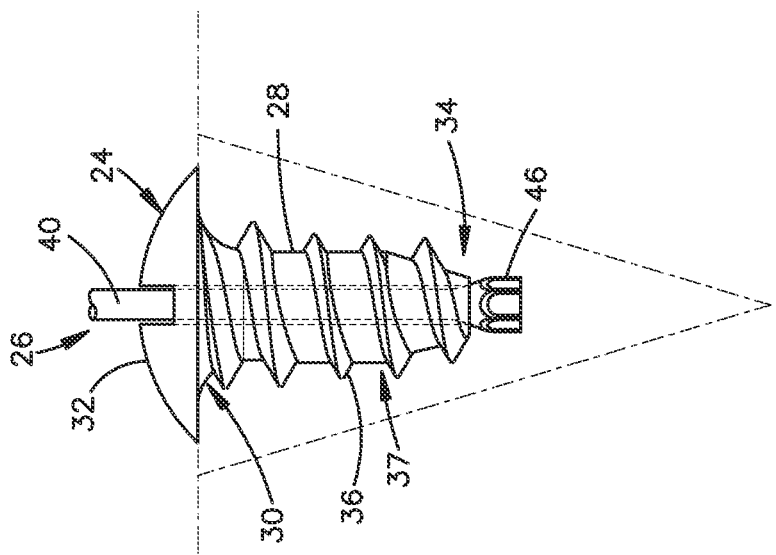
FIG. 2H is a schematic elevation view of a fixation member similar to that illustrated in FIG. 2A, but showing an alternative external anchoring geometry.

As illustrated in FIG. 2I, the threads 36 can be configured to assist in the compression of the bone segments 22a-b toward each other, thereby reducing the fracture 21. In particular, a first set of threads 36a at the proximal end 30 of the shaft 28 can be aligned with the outer bone segment 22a, and a second set of threads 36b at the distal end 34 of the shaft 28 can be aligned with the inner bone segment 22b. To induce compression between the bone segments 22a-b, the threads 36a and 36b can be configured with opposite thread angles with respect to each other and/or can be configured with differing thread pitches. For instance, the threads 36a that engage bone fragment 22a can have one-half the pitch of the threads 36b that engage the bone fragment 22b, the threads 36a and 36b can be configured with thread angles that are oriented away from the fracture line 21, or any combination thereof. Thus, as the threads 36a-b are expanded radially outward in the manner described above, the thread angles and/or the pitches of the threads 36a-b cause the bone segments 22a-b to become axially displaced toward the fracture 21. While a pair of fixation members 24 is illustrated as being inserted into the bone segments 22a-b, it should be appreciated that any desired number of fixation members 24 can be used. Furthermore, when the threads 36a and 36b are constructed with differing thread pitches, it is also possible to achieve axial displacement of the bone fragments 22a and 22b.

It should thus be appreciated that use of the expandable fixation assembly 20 reduces the number of steps associated with joining the bone segments 22a-b, with respect to conventional bone screws. For instance, a single hole (e.g., the bore 38) can be used to secure the fixation member 24, thereby dispensing with the drill guide and the need to drill a second hole. Furthermore, because forces generated during pull through of the expansion member 26 bias the head 32 of the shaft 28 against the outer surface of the surrounding structure, such as a bone or bone plate, the step of counter-sinking the bone is avoided. Thus, a method for installing the fixation member 24 includes the steps of reducing a fracture (e.g., the fracture 21 between the bone segments 22a and 22b), drilling a single through hole into the one or more bone segments, measuring the desired fixation member length, sliding the fixation member 24 into the through hole, and expanding the fixation member 24 with the expansion member 26. Furthermore, because the threads 36 can be helical, the fixation member 24 can be removed by rotating the fixation member 24 in a manner consistent with conventional bone screws.

It should be appreciated that the embodiment of the fixation member 24 illustrated in FIGS. 2A-C is an example embodiment, and that the fixation member 24 and/or the expandable fixation assembly 20 can be constructed in accordance with numerous alternative embodiments, as will be described in more detail below. The following alternative embodiments are not intended to be exhaustive, and any additional or alternative embodiments capable of allowing an expandable fixation member 24 to operate in the manner described herein are intended to fall under the scope of the instant disclosure. It should be further appreciated that features and/or structures of the various embodiments illustrated and described herein can be used in combination with other embodiments illustrated and described herein.

Referring now to FIGS. 3A-3F, the mandrel 46 can impart a desired geometric shape to a portion or an entirety of the inner surface 25 of the shaft 28. In the illustrated embodiment, the outer radial surface 48 of the mandrel 46 is illustrated as defining a hexagonal shape. Thus, as the mandrel 46 is drawn through the shaft 28 of the fixation member 24 in the manner described above (see FIG. 3C), the mandrel 46 imparts a hexagonal profile to the portion of the inner surface 25 that has an inner diameter or cross-sectional dimension that is smaller than the outer dimension of the outer surface 48. Accordingly, once the mandrel 46 is removed from the fixation member 24, at least a portion of the inner surface 25 has a hexagonal cannulation, as illustrated in FIG. 3F. In an alternative embodiment of the mandrel 46 as illustrated in FIG. 3B, one or more relief structures, for example grooves 49, can be formed within the outer radial surface 48 of the mandrel 46. The relief grooves 49 reduce the surface area of the mandrel 46 that interferes with the bore 35 of the shaft 28 as the mandrel 46 is pulled therethrough, thereby reducing the amount of force required to pull the mandrel 46 through the shaft 28.

The cannulation left by the mandrel 46, and more generally the bore 35 of the shaft 28, can provide a medication port for the injection of a desired medication into the bore 38. The medication can, for instance, be injected with a standard syringe and without creating an additional hole to provide access to the injection site. Additionally, the shaft 28 of the fixation member 24 could have holes drilled normal to the outer surface through the wall and into the bore 35 of the shaft 28. These holes would allow the medication to be delivered into the surrounding bone. Additionally, a biodegradable or drug eluting polymer can be inserted into the bore 35 of the fixation member 24. The cannulation left by the mandrel 46 can also be used in neurological applications, for example with intercranial pressure monitoring devices that may be disposed within the cannulation, fluid monitoring devices, and the like. The cannulation can also serve as a drain port, for example in a shunting application Furthermore, if it becomes desirable to remove the fixation member 24 from the bone segments 22a-b, a driving instrument, such as a screwdriver having a hexagonal, or other polygonal engagement region as appropriate, can be inserted into the shaft 28 of the fixation member 24 such that the hexagonal engagement region of the screwdriver mates with the hexagonal cannulation of the fixation member 24. The screwdriver can then be rotated in the usual manner, thereby causing the threads 36 to ride along the surrounding bone, thereby backing the fixation member 24 out of the bore 38. It should be appreciated from FIGS. 3C and 3E that the entire length of the shaft 28 can be threaded.

Figure 3J:
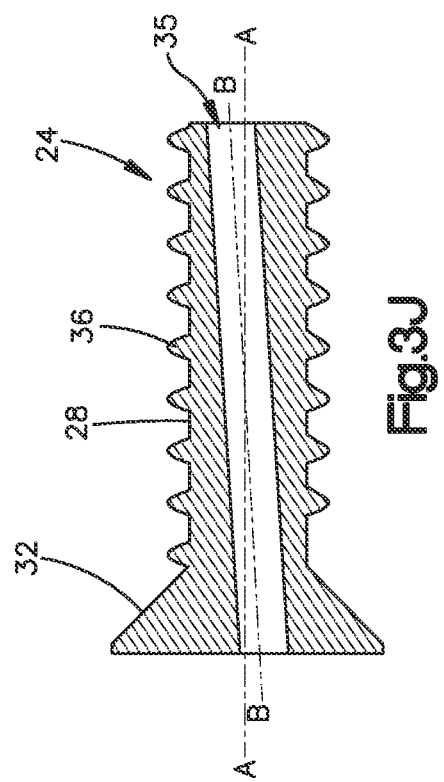
FIG. 3J is a sectional side elevation view of the expandable fixation member of the expandable fixation assembly illustrated in FIG. 3C in accordance with still another alternative embodiment, prior to expansion of the fixation member.
Figure 3I:
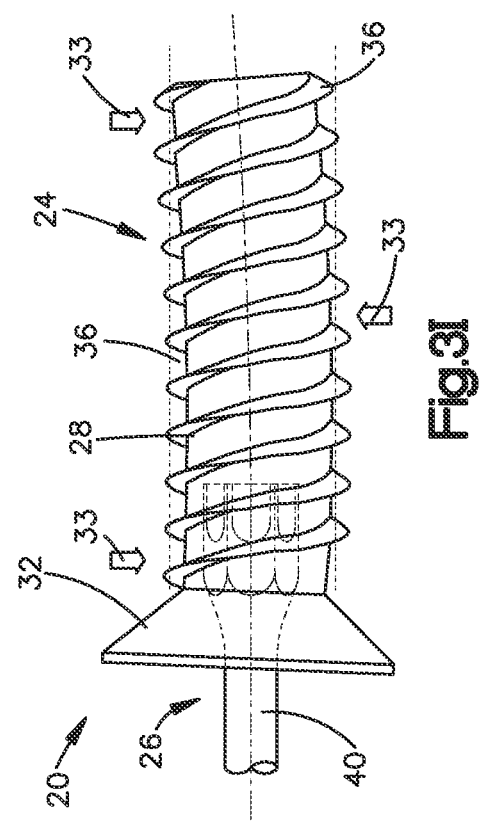
FIG. 3I is a side elevation view of the expandable fixation member illustrated in FIG. 3G, after expansion of the expandable fixation member.

In an alternative embodiment of the fixation member 24 illustrated in FIGS. 3G-I, the bore 35 of the shaft 28 can be formed along a bore axis that is offset with respect to the axis A-A, resulting in a non-uniform wall thickness of the shaft 28. Expanding a fixation member having an offset bore 35 can result in an expanded fixation member 24 having a curved geometry. The curved geometry can produce a three-point contact load, for example at contact points 33, thereby increasing pullout resistance of the expanded fixation member 24 with respect to the bore 38. Alternatively, a fixation member 24 with an offset bore 35 and no threads 36 can be used as a trauma plating pin. In such an application, non-threaded fixation members 24 with specific pullout resistances can be manufactured. Additionally, a plurality of non-threaded fixation members 24 can be used in combination with a bone plate to prescribe opposing pin axial vectors.

In still another alternative embodiment of the fixation member 24 illustrated in FIGS. 3J-L, the bore 35 of the shaft 28 can be formed along a bore axis B-B that is offset and/or angled with respect to the axis A-A, resulting in a non-uniform wall thickness of the shaft 28. Expanding a fixation member having an offset and/or angled bore 35 can result in an expanded fixation member 24 having an "S" shaped geometry. The S shaped geometry can produce a four-point contact load, for example at contact points 33, thereby increasing pullout resistance of the expanded fixation member 24 with respect to the bore 38. It should be appreciated that more or fewer than four contact points can result based on the degree of offset and/or angulation of the bore axis B-B. Alternatively, a fixation member 24 with an offset and/or angled bore 35 and no threads 36 can be used as a trauma plating pin. In such an application, non-threaded fixation members 24 with specific pullout resistances can be manufactured. Additionally, a plurality of non-threaded fixation members 24 can be used in combination with a bone plate to prescribe opposing pin axial vectors.

Referring now to FIG. 4A, both the mandrel 46 and the fixation member 24 can be self-drilling. In particular, the fixation member 24 and the mandrel 46 can present axially outer cutting surfaces, such as cutting flutes 51 and 53, respectively, at their axially leading edges. In this embodiment the outer diameter, or outer dimension, of the mandrel 46 is less than that of the outer diameter OD1 of the threaded region of the fixation member 24 prior to expansion. During use, the mandrel 46 and the fixation member 24 can be rotated as they are inserted into the bone segments 22a-b, such that the cutting flute 53 of the mandrel 46 cuts a portion of the bore 38 sufficient to allow the mandrel 46 to pass through, and the cutting flute 51 of the fixation member 24 widens the bore 38, thereby allowing the shaft 28 to pass through to the position illustrated in FIG. 2B. Thus, the bore 38 is drilled into the bone segments 22a-b simultaneously with the insertion of the fixation member 24 and the mandrel 46. The mandrel 46 can then be pulled through the shaft 28 of the fixation member 24 in the manner described above to secure the fixation member 24 to the bone segments 22a-b.

In an alternative embodiment depicted in FIG. 4B, the cutting flutes 53 of the mandrel 46 can have a diameter greater than the outer diameters OD 1 and/or OD2 of the shaft 28. In particular, the mandrel 46 can include a plurality of flexible legs 68 that flare away from each other and are separated by an air gap 71. The cutting flutes 53 therefore drill the bore 38 as the shaft 40 is rotated during insertion of the threaded fixation assembly 20. The resulting bore 38 has a diameter D1 greater than the outer diameters OD 1 and/or OD2 of the shaft 28 prior to expansion of the fixation member 24, thus the fixation member 24 is received loosely in the bore 38 created by the cutting surfaces 53. As the mandrel 46 is pulled through the bore 35 of the shaft 28, the flexible legs 68 collapse toward each other to define an outer diameter, or outer dimension, that is smaller than the bore 38 but larger than the inner diameter of the bore 35. Thus the mandrel 46 expands the shaft 28 of the fixation member 24 as it is drawn through the shaft 28 in the manner described above. The expansion member 26 can include a threaded and/or form-locking structure at the proximal end of the shaft 40 that assists in gripping the shaft 40 when pulling the mandrel 46 through the bore 35 of the shaft 28.

In another alternative embodiment, the fixation member 24 includes a plurality of self-tapping cutting flutes 70 disposed on the outer surface of the shaft 28 of the fixation member 24, for example in proximity to the distal end 34 of the shaft 28 and adjacent to the proximal end of the anchoring region 37. The cutting flutes 70 are configured to cut through surrounding bone during rotation of the fixation member 24 as the fixation member 24 moves in a backward direction (i.e., as the fixation member 24 is removed from the bore 38 in the bone segments 22a-b). It should be appreciated that the fixation member 24 can receive a hexagonal or other polygonal cannulation in the manner described above, and/or the head 32 can include a suitable groove that receives a screw driving instrument that can rotate the fixation member 24. As depicted in FIG. 4C, the outer diameter of the cutting flutes 70 can become progressively smaller in a direction from the distal end 34 toward the proximal end 30 of the shaft 28, thereby defining a descending axial profile of cutting flutes. Accordingly, each successive cutting flute 70 incrementally removes a portion of the surrounding bone, thereby ultimately widening the bore 38 to an amount at least as wide as the outer diameter OD2 of the threads 36, which is sufficient to allow the remainder of the fixation member 24 to be easily pulled out of the bore 38 in the bone segments 22a-b.

Figure 5:
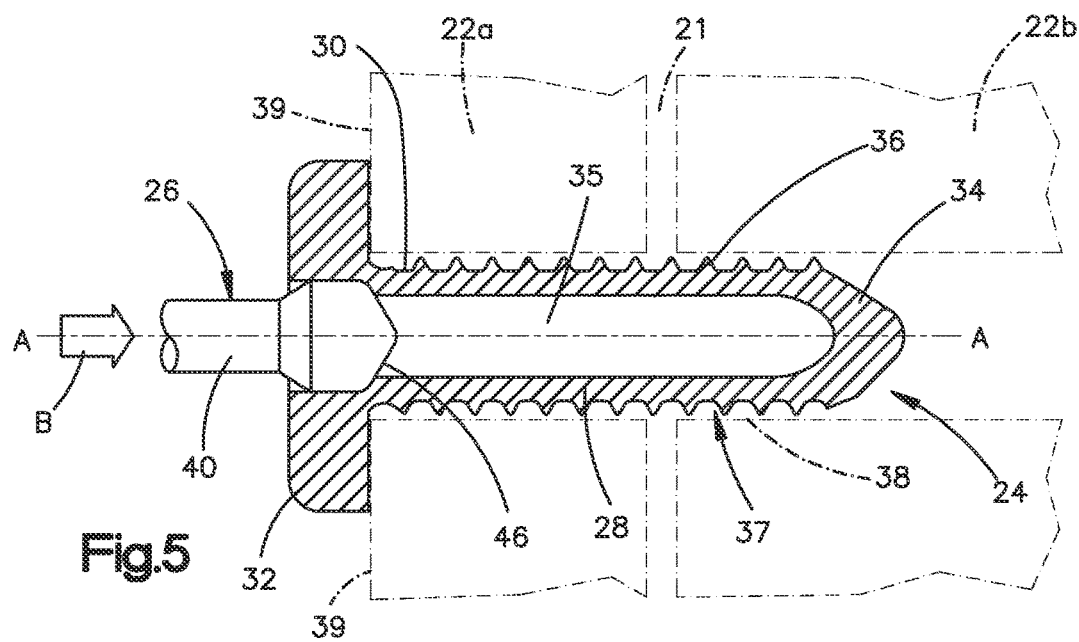
FIG. 5 is a side elevation view of an expandable fixation assembly having an expansion member inserted into a bore of the expandable fixation member.

Referring now to FIG. 5, the expansion member 26 can be pushed into the bore 35 as opposed to being pulled through the bore 35 as described above. In the illustrated embodiment, the bore 35 is closed at the distal end 34 of the shaft 28 at a location radially inward of the threads 36. The portion of the bore 35 that is radially aligned with the threads 36 presents an inner diameter smaller than the outer diameter, or outer dimension of the mandrel 46, such that inserting the mandrel 46 into the bore 35 along the direction of Arrow B causes the shaft 28 to expand in the manner described above. The method of expanding the fixation member 24 as illustrated in FIG. 5 includes the steps identified above with respect to FIGS. 2A-C, however instead of inserting the fixation member 24 and the expansion member 26 into the bore 38 together, the fixation member 24 is inserted into the bore 38 individually, and the mandrel 46 is then pushed axially inward into the bore 35. It should be appreciated that interference between the mandrel 46 and the bore 35 biases the head 32 against the outer surface 39 of the bone segment 22a, thereby reducing the fracture 21 between the bone segments 22a and 22b, as the mandrel 46 is inserted into the bore 35. Once the fixation member 24 has expanded, the mandrel 46 can be easily removed from the fixation member 24. Alternatively, in accordance with this or any other embodiment, once the fixation member 24 has been expanded as desired, the shaft 40 of the expansion member 26 can be cut such that the expansion member 26 can be left inside the shaft 28 of the fixation member 24 after expansion. Alternatively, in accordance with this or any other embodiment, the shaft 40 of the expansion member 26 can be manufactured in a predetermined length such that once the fixation member 24 has been expanded as desired, the expansion member 26 will be contained within the shaft 28 of the fixation member 24 after expansion.

Figure 6A:
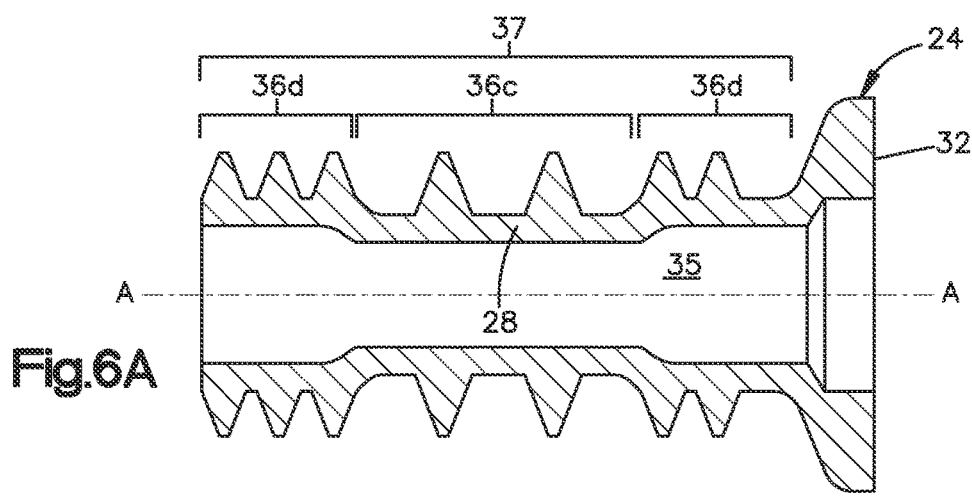
FIG. 6A is a sectional side elevation view of the anchoring geometry of an expandable fixation member in accordance with an embodiment.

Furthermore, referring to FIG. 6A, the threaded portion of the shaft 28 can include multiple threaded zones 36c and 36d that have at least one varying thread characteristic. For instance, the threads 36 can have varying depths at the corresponding zones 36c and 36d to allow for enhanced securement of the fixation member 24 to different layers of bone. For example, deeper threads 36 are advantageous in a region of the shaft 28 that is secured in softer bone, such as cancellous bone. Thus, varying thread characteristics can be selected based on the properties of the bone region that is aligned with the expanding threads 36.

Figure 6B:
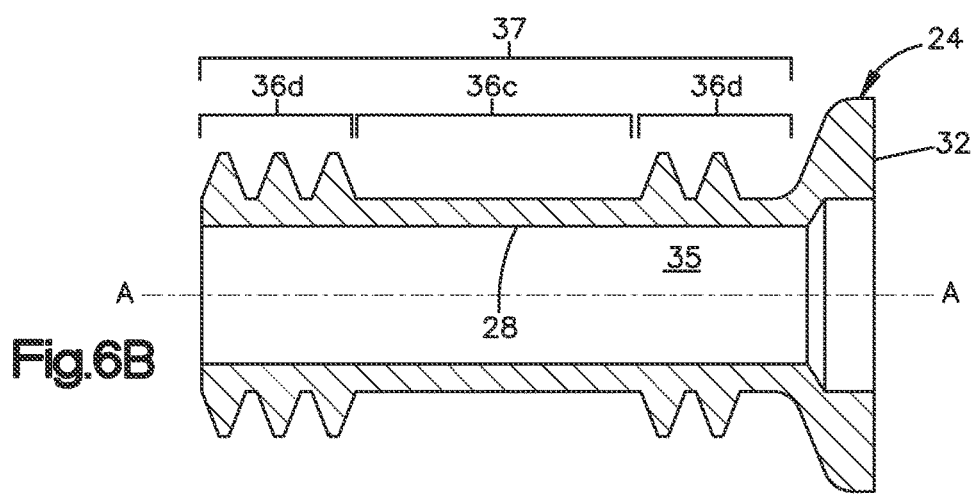
FIG. 6B is a sectional side elevation view of the anchoring geometry of an expandable fixation member in accordance with another embodiment.

In the illustrated embodiment, threaded zone 36c is configured to align with a cancellous bone portion, while the threaded zones 36d are disposed on both sides of the threaded zone 36c and are configured to align with cortex bone portions. Thus, the threads of the threaded zone 36c are spaced axially further apart, define a radial distance (or thread height) that is greater than the thread height of the threads in the threaded zones 36*d*, and are wider at their roots than the threads in the threaded zones 36*d*. However, because the inner diameter of the portion of the shaft 28 shaft that is radially aligned with the threaded zone 36*c* is smaller than the diameter of the portions of the shaft 28 that are radially aligned with the threaded zones 36*d*, the outer diameter of the threads 36 can be consistent across the threaded zones 36*c* and 36*d*. Once the fixation member 24 is expanded, the threads of the threaded zone 36*c* will be radially outwardly displaced with respect to the threads of the threaded zones 36*d*. Alternatively, referring to FIG. 6B, the threaded zone 36*c*, corresponding to cancellous bone, can be devoid of threads, such that only the threads of the threaded zones 36*d*, associated with cortex bone, engage surrounding bone upon expansion of the fixation member 24.

Referring now to FIG. 6C, the fixation member 24, having any desired thread pattern and/or threaded sections, can be provided as a screw that can be inserted into the bone segments 22*a-b* in a manner consistent with conventional bone screws, and subsequently expanded if desired. For instance, the fixation member 24 can be provided with an expansion member 26 disposed inside the bore 35, such that the distal end of the mandrel 46 is either flush with the distal end 34 of the shaft 28, or recessed in the bore 35. Accordingly, if the fixation member 24 is loose inside surrounding bone, or if another need arises to further secure the fixation member 24 inside the bore 38 formed in the bone, a reciprocating brace can be placed against the outer surface of the head 32. Once the brace is placed in position, the expansion member 26 can be pulled through the shaft 28 of the fixation member 24 while the brace 56 bears against the head 32 to provide a reciprocal axial force against the force created by the expansion member 26 as it is pulled through the shaft 28 of the fixation member 24, thereby expanding the fixation member 24 in the manner described above. Alternatively, the fixation member 24 can be configured as illustrated in FIG. 5, such that the mandrel 46 can be pushed into the shaft 28 of the fixation member 24 if the fixation member 24 is loose inside the bone segments 22*a-b*, or it is otherwise desired to reinforce the structural integrity of the joint formed by the fixation member 24.

Referring now to FIGS. 7A-F, the fixation member 24 can be configured for angulation prior to expansion. For instance, the head 32 of the fixation member 24 can define a convex outer surface 72 configured to mate with a complementary concave inner surface 74 extending into a bone plate 62. Thus, engagement between the convex outer surface 72 and then concave inner surface 74 approximates a ball-and-socket joint that allows for angulation of the fixation member 24 relative to the bone plate 62, whereby the axis A-A of the fixation member 24 can be angularly offset. The bore 35 of the shaft 28 can have a diameter or cross-sectional dimension at a location in radial alignment with the head 32 that is less than the diameter of the outer surface 48 of the mandrel 46. Accordingly, the convex outer surface 72 of the head 32 will radially expand into an interfering relationship with the concave inner surface 74 of the bone plate 62 when the mandrel 46 is pulled through the bore 35 of the shaft 28.

As shown in FIG. 7B, the concave inner surface 74 of the bone plate 62 can include a plurality of anchoring geometries, such as threads 76, configured to bite into, or otherwise engage, the convex outer surface 72 of the head 32 of the fixation member 24 in response to expansion of the head 32. In an alternative embodiment, the anchoring geometries can comprise variable diameter, lobular, structures configured to deform against a plurality of concentric rings formed in the convex outer surface 72 of the head 32 or the concave inner surface 74 of the bone plate 62. It should be noted that the anchoring geometries can take the form of any other suitable engagement structure as desired. The head 32 can be made from a material that yields more readily than the material of the bone plate 62, and can include any suitable biocompatible and/or resorbable materials and/or alloys which offer a desired amount of ductility for the radial expansion as well as stability to withstand the indication-specific, applied forces. The bone plate 62 can be made from any suitable material such as a stainless steel or titanium alloy. The fixation members 24 can be made from a commercially pure titanium, softer grade of stainless steel, titanium alloy, polymer, and the like. Accordingly, the convex outer surface 72 can deform in response to contact with the threads 76 of the concave inner surface 74, thereby enhancing the mating relationship between the bone plate 62 and the head 32.

Alternatively, the concave inner surface 74 of the bone plate 62 can be smooth while the convex outer surface 72 of the head 32 has anchoring geometries formed thereon, for example threads 76, such that the threads 76 of the convex outer surface 72 bite into, or otherwise engage, the concave inner surface 74 of the bone plate 62. Alternatively, both the convex outer surface 72 of the head 32 and the concave inner surface 74 of the bone plate 62 can be threaded or otherwise provided with anchoring geometries. Alternatively still, a bore 38 with a concave surface can be formed in the bone segment 22*a*, and the convex outer surface 72 of the head 32 can be threaded, such that the threads 76 of the convex outer surface 72 bite into, or otherwise engage, the concave surface of the bone segment 22*a* when the mandrel 46 is pulled through the head 32.

The embodiment depicted in FIGS. 7A-B creates an interference fit between the head 32 and the bone plate 62, thereby engaging the head 32 of the fixation member 24 into a locked configuration within the bone plate 62. Accordingly, the fixation member 24 will no longer be able to move independently of the bone plate 62, thereby preventing the fixation member 24 from rotating about the axis A-A and backing out of the bone and/or bone plate. Furthermore, a single rigid construct is created between the bone plate 62 and the fixation member 24, thus fixing the bone fragments 22*a-b* rigidly. It should be appreciated that more axial rotation is allowed in defining an angle between the fixation member 24 and the plate 62 than is allowed with respect to conventional bone screws.

Additionally, because the locking occurs as the result of radial expansion of the head 32, the locking forces created by the expansion are reproducible independent of any torque applied by the surgeon. Insertion torque can vary when fastening conventional bone screws without the use of a torque limiter. The fixation member 24 of the illustrated embodiment can achieve reproducible locking forces without the use of a torque limiter. Furthermore, when using conventional bone screws having a long length, the insertion torque required for the final tightening of the screw can cause the screw to fail. In this regard, it should be appreciated that the required insertion torque for conventional bone screws affects the locking stability and thus the overall stability of the resulting construct. If too much torque is used for screw insertion, there is little left for locking torque. As a consequence, too little locking torque may ultimately result in an unstable plate/screw mating interface and thus ultimately an unstable fracture construct. The fixation member 24 of the illustrated embodiment can provide expansion forces, and forces applied by the fixation member 24, that are independent of the length of the shaft 28 of the fixation member 24.

In an alternative embodiment, as illustrated in FIG. 7C, one or more axial slots 41 can be formed within the head 32, the axial slots 41 beginning in the proximal end of the head and extending into the head in a distal direction. The axial slots 41 can be configured to control the degree of expansion of the head 32, while reducing the amount of force that must be applied to the shaft 40 of the expansion member 26 to pull the mandrel 46 through the head 32. This configuration may be achieved by varying, for example, the number and/or length of the axial slots 41, the material the head 32 is manufactured from, and the like. Reducing the amount of force that must be applied to the shaft 40 of the expansion member 26 to pull the mandrel 46 through the head 32 can mitigate the likelihood that the shaft 40 and/or the mandrel 46 of the expansion member breaking during the expansion process.

In another alternative embodiment, depicted in FIG. 7D, the shaft 28 of the fixation member 24 has a locking structure formed thereon, such as annular ridge 43 extending radially outward from the shaft 28 at the proximal end 30 of the shaft 28, just below the head 32. As the mandrel 46 is pulled through the shaft 28, causing the shaft 28 to expand radially outward as described above, the annular ridge 43 expands and engages the lower surface of the bone plate 62. The expanded annular ridge 43 provides further protection against backout of the fixation member 24 from the bore 38, for example in addition to the locking between the head 32 of the fixation member 24 and the bone plate 62 described above.

In still another alternative embodiment, depicted in FIGS. 7E-F, the head 32 of the fixation member 24 has a tapered, or variable diameter, bore formed therein. Varying the diameter of the bore 35 within the head 32 allows control the expansion of the head 32 against the bone plate 62 and/or the force required to pull the mandrel 46 through the head 32 of the fixation member 24. The inner diameter of the bore 35 in the head 32 can be tapered to produce one or more distinct activation zones, such as activation zones 32*a-c*. In the illustrated embodiment, the first activation zone 32*a* controls expansion of the shaft 28 of the fixation member 24 within the surrounding bone of the bore 38. The second activation zone 32*b* controls expansion of the convex outer surface 72 of the head 32 against the concave inner surface 74 of the bone plate 62. The third and final activation zone 32*c* controls release of the mandrel 46 as it is pulled through the proximal end of the head 32.

As shown in FIG. 8, the fixation member 24 can be threaded in a manner that is configured to prevent backout of the fixation member 24 from the bone segment 22. In particular, the head 32 of the fixation member 24 can be disposed in a seat 65 of the bone plate 62 in the manner described above. For instance, the head 32 can threadedly engage the seat 65, or can present a smooth convex outer surface that nests within a smooth concave inner surface defined in the seat 65. A substantially cylindrical or suitably alternatively shaped bore 80 can extend through the inner portion of the bone plate 62 at a location aligned with the seat 65. Accordingly, the shaft 28 of the fixation member 24 can extend through the bore 80 while the head 32 is disposed in the seat 65. Prior to expansion, the threads 36 can define an outer diameter that is substantially equal to or smaller than the diameter of the bore 80 such that the shaft 28 can be inserted into the bore 80, through the bone plate 62, and into the bore 38 formed in the bone segment 22. One or more, or a defined section, of the threads 36 located axially on the shaft 28 in close proximity to the inside surface of the bone plate 62, can be configured to act as locking threads 36, that is to expand to a diameter greater than the diameter of the bore 80 as the mandrel 46 is pulled through the shaft 28, thereby effectively locking the fixation member 24 within the bore 38. Interference between the expanded locking threads 36 and the bone plate 62 prevents the fixation member 24 from loosening (i.e., the fixation member 24 is prevented from unscrewing itself due to, for example, acting loads and/or micro movements of the bone segments). Accordingly, in some instances, a screwdriver may be required to provide a predetermined torque in order to deform the locking threads 36 in order to post-operatively remove the expanded fixation member 24.

Figure 9A:
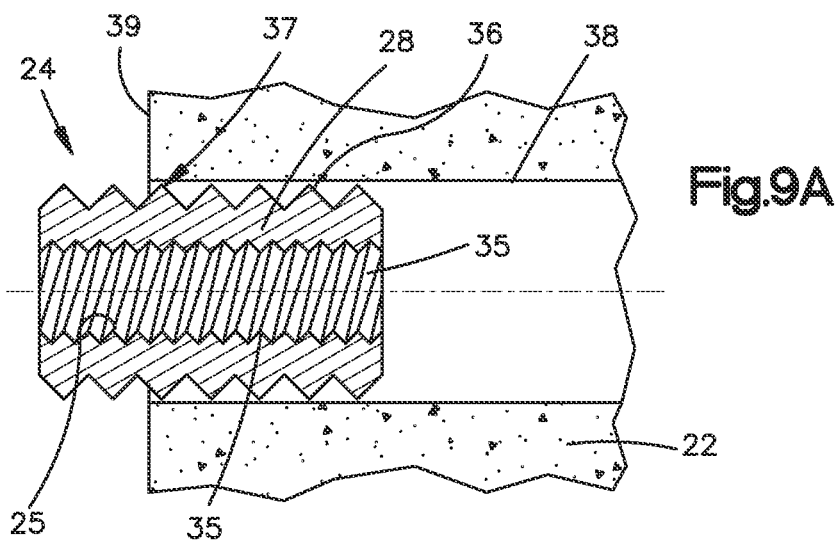
FIGS. 9A-C are sectional side elevation views of an expandable fixation member without a head in accordance with an embodiment.
Figure 9B:
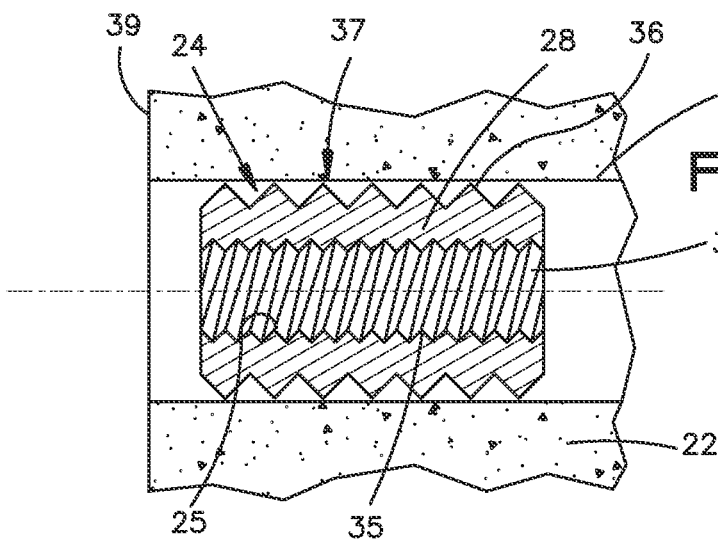
Figure 9C:
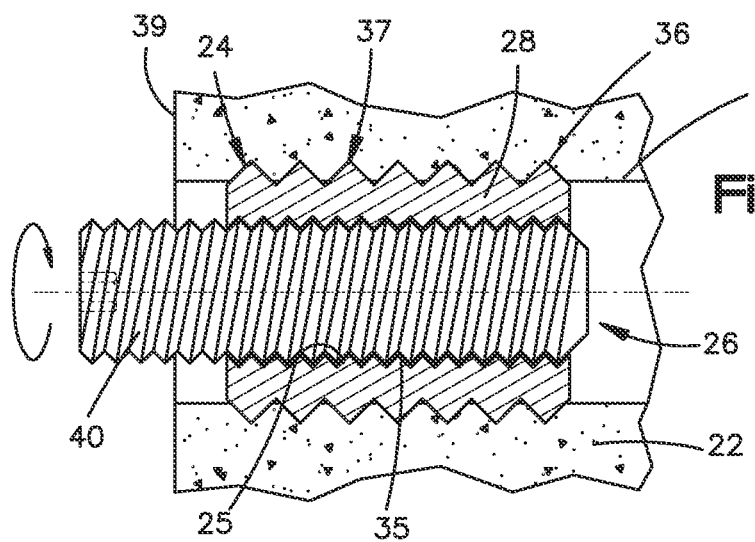

Referring now to FIGS. 9A-C, the fixation member 24 can be provided without the head 32, such that the fixation member 24 only includes the shaft 28. Thus, the fixation member 24 of FIGS. 9A-C can be completely embedded, for example as an implant, in the bone segment 22, and can be inwardly recessed with respect to the outer surface 39 of the bone segment 22. The shaft 28 of the fixation member 24 can be inserted into the bore 38, and the expansion member 26 can be inserted into the bore 35 of the shaft 28 in the manner described above, or by rotating the shaft 40 of the expansion member 26. In particular, the outer surface of the shaft 40 of the expansion member 26 can have a plurality of threads formed thereon, the threads configured to engage with complimentary threads formed on the inner surface 25 of the shaft 28. The diameter, or other outer dimension, of the shaft 40 can be uniform throughout its length. Alternatively the diameter, or other outer dimension, of the shaft 40 may be varied, for instance tapered, along one or more sections, or the entirety, of the length of the shaft 40. Thus, rotation of the shaft 40 relative to the fixation member 24 can cause the expansion member 26 to be inserted, or driven, into the bore 35. The expansion member shaft 40 can be sized, for example via the diameter, or other outer dimension, to cause the shaft 28 of the fixation member 24 to expand radially outward, thereby maintaining engagement of the threads 36 with the surrounding bone of the bone segment 22. Expansion of the fixation member 24 reduces or prevents stress peaks in the bone/fixation member interface and generates a smoother intersection between the material properties of the fixation member 24 and the weaker properties of the surrounding bone of the bone segment 22. In an example embodiment, the headless fixation member 24 depicted in FIGS. 9A-C could be used in an expandable knee implant assembly.

In an alternative embodiment depicted in FIGS. 9D-E, the fixation member 24 can alternatively be used as a spacer between two adjacent bones 22*a-b*, for example to maintain a desired spacing therebetween. The outer surface of the intermediate portion 31 of the shaft 28 has a plurality of helical threads 36 extending outwardly therefrom, and the outer surface of the proximal and distal ends 30 and 34 of the shaft 28 are smooth. The inner diameter of the bore 35 in the intermediate portion 31 of the shaft 28 is smaller than the inner diameter of the bore at the proximal and distal ends 30 and 34 of the shaft, such that the outside diameter of the shaft is uniform between the proximal and distal ends 30 and 34, and such that only the intermediate portion 31 of the shaft 28 is expanded when the mandrel 46 is pulled through the shaft 28. As the mandrel 46 is pulled through the shaft 28 in the manner described above, the intermediate portion 31 of the shaft expands radially outward, causing the threads 36 to engage the adjacent bone and to secure the position of the fixation member 24 between the bone segments 22a-b, and thereby the spacing between the bone segments 22a-b.

Figure 9F:
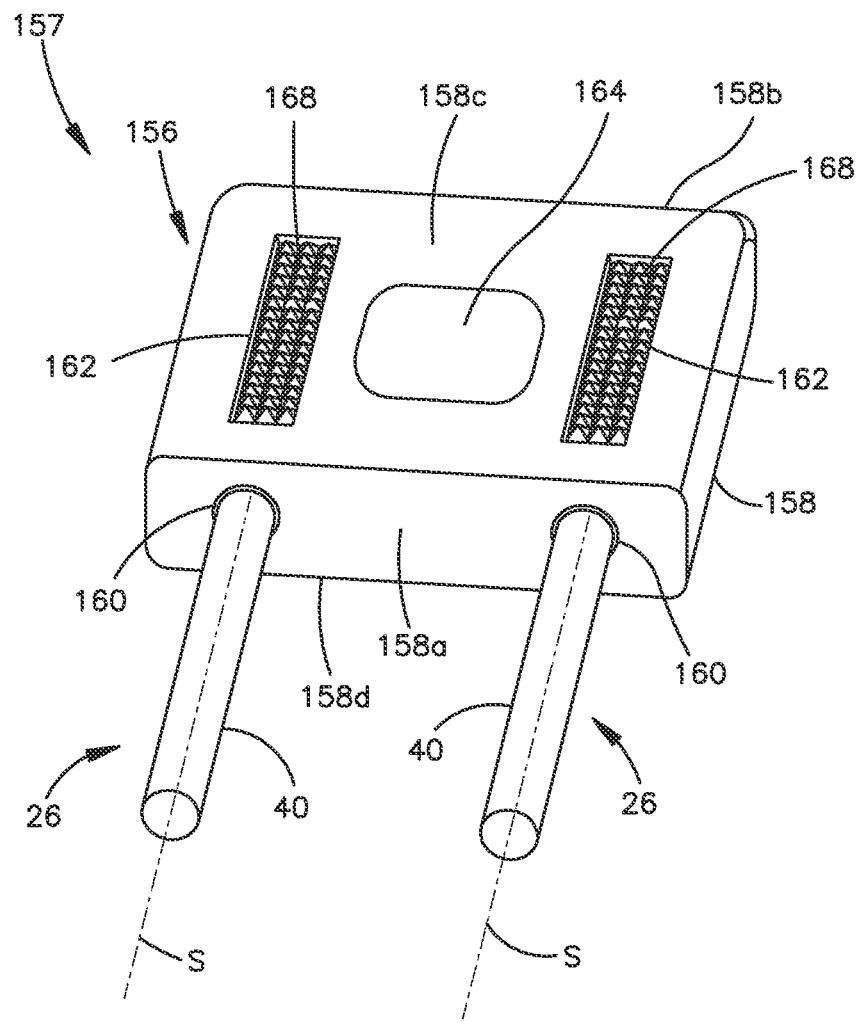
FIG. 9F is perspective view of an expandable intervertebral implant assembly in accordance with an embodiment.
Figure 9G:
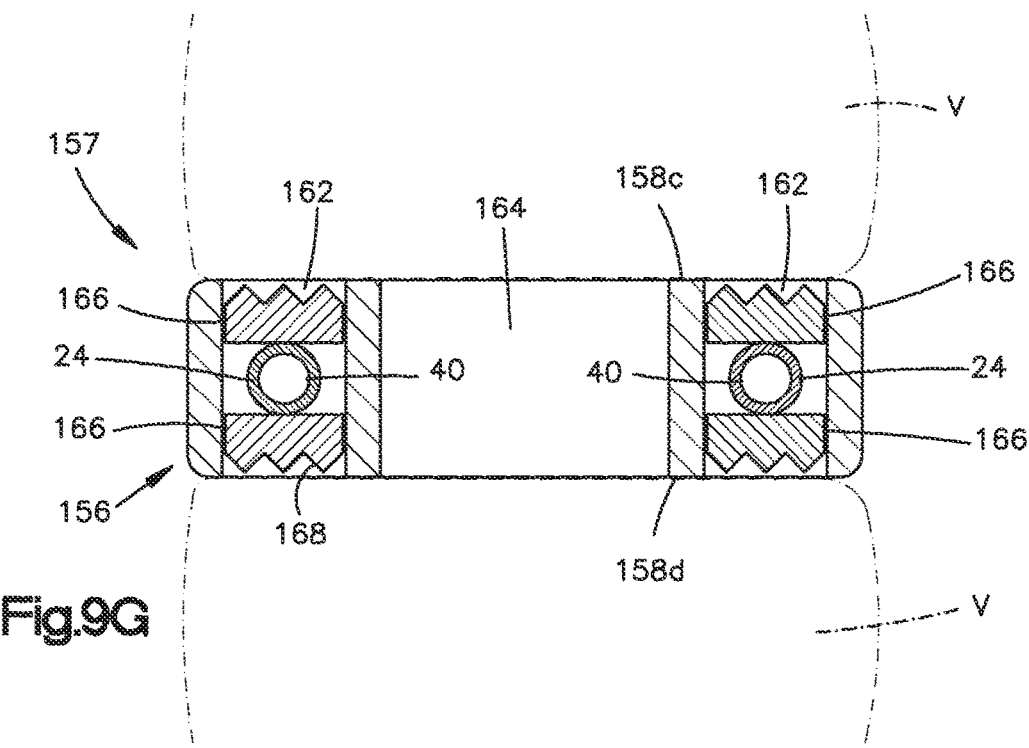
FIG. 9G is a sectional front elevation view of the expandable intervertebral implant assembly illustrated in FIG. 9F, prior to expansion of the expandable fixation members.
Figure 9H:
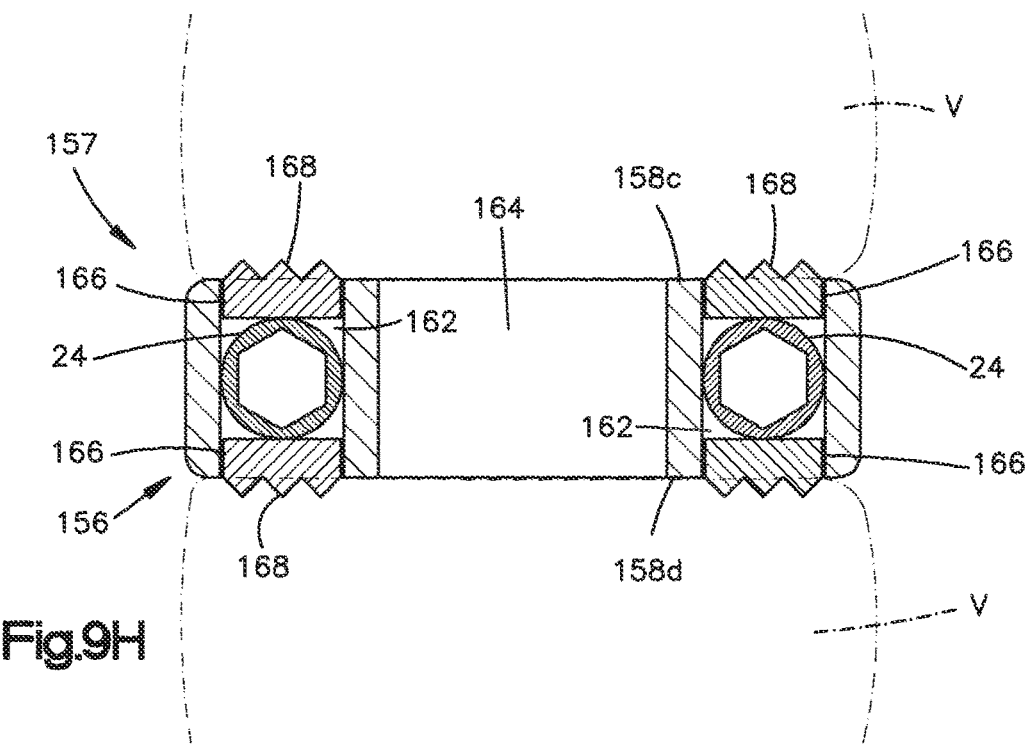
FIG. 9H is a sectional front elevation view of the expandable intervertebral implant assembly illustrated in FIG. 9F, after expansion of the expandable fixation members.

In still another alternative embodiment depicted in FIGS. 9F-H, a pair of expandable fixation assemblies 20 are used in combination with an intervertebral implant 156 in an expandable intervertebral implant assembly 157. The intervertebral implant 156 includes an implant body 158 having a generally rectangular shape defining opposing proximal and distal ends 158a and 158b, and opposing upper and lower surface 158c and 158d. It should be appreciated that the rectangular shape of the implant body 158 is merely an example implant body geometry, any that other implant body geometry may be used as desired, for example as anatomy in a target intervertebral space may dictate. The upper and lower surfaces 158c and 158d may be smooth, may have gripping features such as teeth, spikes, or similar structures formed thereon and configured to facilitate gripping engagement between the upper and lower surfaces 158c and 158d and the end plates of adjacent vertebral bodies, or may have discrete smooth and gripping portions. The body can further include an optional central bore 164 configured, for example, to be filled with bone growth inducing substances to allow bony ingrowth and to assist in fusion between the intervertebral implant 156 and adjacent vertebral bodies.

The implant body 158 can have one or more fixation assembly bores formed therein, the bores having an inner diameter larger than the outer diameter of one or more expandable fixation assemblies 20 that are disposed within the bores. In the illustrated embodiment, a pair of bores 160 are formed in the proximal end 158a of the implant body 158, extending in a rearward direction along a pair of bore axes S toward the distal end 158b. The implant body 158 can further have one or more openings in the outer surface of the implant body that are configured to allow bone engagement structures to protrude from the implant body 158 and engage surrounding structure, such as the end plates of adjacent vertebral bodies. In the illustrated embodiment, a pair of vertical slots 162 are formed through the implant body 158 and the bores 160 between the upper and lower surfaces 158c and 158d, the slots 162 aligned lengthwise with the shaft axes S. The expandable fixation assemblies 20 are disposed within respective bores 160.

One or more engagement structures, such as engagement blocks 166, can be disposed within the implant body 158, the engagement block 166 configured to be disposed on opposing sides of the expandable implant assemblies 20, between the fixation members 24 and the upper and lower surfaces 158c and 158d of the implant body 158, such that when the fixation members 24 are expanded, the engagement blocks 166 are biased toward respective upper and lower surfaces 158c and 158d of the implant body 158, with at least a portion of the engagement blocks 166 protruding from the implant body 158, for example through the slots 162, and engaging surrounding structure. It should be appreciated that the positioning of the slots 162 in the illustrated embodiment is merely an example, and that more or fewer slots, or other geometric openings, can be positioned in any suitable location on the surface of the implant body 158.

The engagement blocks 166 have opposing fixation member facing surfaces, and bone facing surfaces, the bone facing surfaces having one or more bone engagement structures formed thereon, for example a plurality of teeth 168. In the illustrated embodiment The engagement blocks 166 are carried within the implant body 158, between the expandable fixation assemblies 20 and the upper and lower surfaces 158c and 158d of the implant body 158, as described above.

The engagement blocks 166 are configured to be of such a thickness that before the fixation members 24 are expanded, the teeth 168 are contained within the implant body 158. In alternative embodiments, the engagement blocks 166 can be omitted, such that bone engagement structures formed on the outer surfaces of the fixation members 24 engage the surrounding structure directly, as described in more detail below.

During use, the expandable intervertebral implant assembly 157 is disposed within an intervertebral space, for example between two adjacent vertebral bodies V, as depicted in FIG. 9G. When the implant 156 is positioned as desired, the mandrels 46 can be pulled through the shafts 28 of the respective fixation members 24, causing the shafts 28 of the fixation members 24 to expand radially outward, thereby biasing the engagement blocks 166 in respective cranial and caudal directions, such that the teeth of the engagement blocks protrude through the openings of the slots 162 and engage respective endplates of the adjacent vertebral bodies V as illustrated in FIG. 9H, thereby fixing the expandable intervertebral implant assembly 157 in position within the intervertebral space. If it is desirable to remove the implant 156 after insertion, a screw driving tool can be inserted into the expanded bores 35 of the fixation members 24 as described above, allowing the fixation members 24 to be removed from the bores 160 of the implant body 158. Once the fixation members 24 are removed from the implant 156, the engagement blocks 166 can return to their pre-insertion configuration, such that the teeth 168 no longer engage the adjacent vertebral bodies V. The implant can then be easily removed.

Figure 9I:
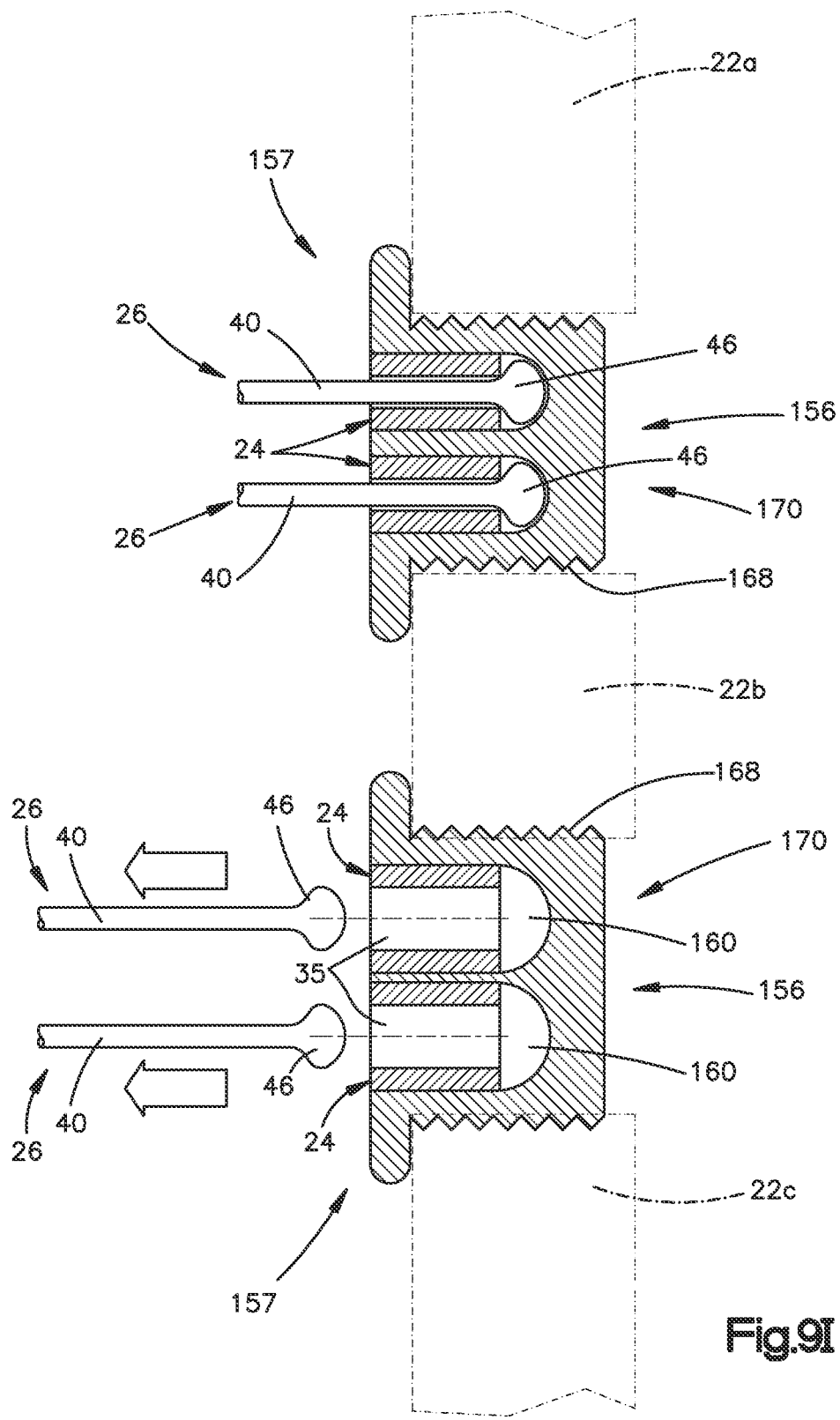
FIG. 9I is a sectional side elevation view of a pair of expandable intervertebral implant assemblies in accordance with an alternative embodiment.
Figure 9M:
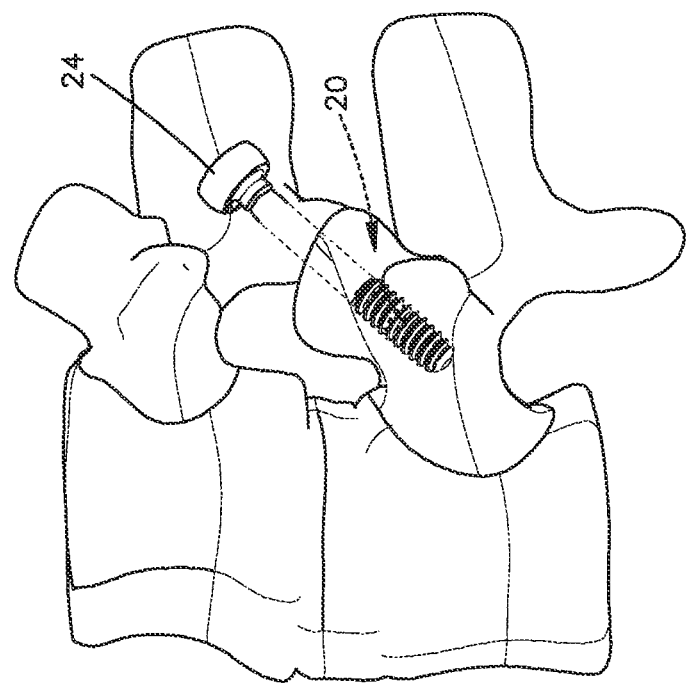

In still another alternative embodiment depicted in FIG. 9I, a pair of expandable intervertebral implant assemblies 157 are provided as bone spacers disposed in corresponding voids 170 between adjacent bones and/or bone segments 22a-c. In the illustrated embodiment, the slots 162 of the previously discussed embodiment are omitted, and the outer surfaces of the implants 156 have bone engagement structures formed thereon, for example teeth 158. During use, the implants 156 are disposed within the voids 170 between the bones and/or bone segments 22a-c and positioned as desired. As the mandrels 46 are pulled though the shafts 28 of the fixation members 24, the shafts 28 of the fixation members 24 expand radially outward against the inner surfaces of the bores 160, causing the bodies 158 of the implants 156 to expand within the voids 170, and in turn causing the teeth 168 to engage with the outside surfaces of the bones and/or bone segments 22a-c, thereby fixing the implants 156 in position within the voids 170. In order to ensure that the implant bodies 158 retain their expanded geometries, the shafts 40 of the expansion members 26 can be cut as described above, such that the mandrels 46 are retained within the bores 35 of the fixation members 24. It should be appreciated that fixation members 24 having differing shaft thickness T and/or anchoring regions 37 can be used with a single implant body configuration, for example to achieve varying degrees of expansion of the implant body 158 as desired. Furthermore, the implant body itself can be configured as the fixation member 24, such that the mandrels 46 are pulled through bores 35 formed within the implant body 158/fixation member 24, causing direct expansion thereof.

Figure 9L:
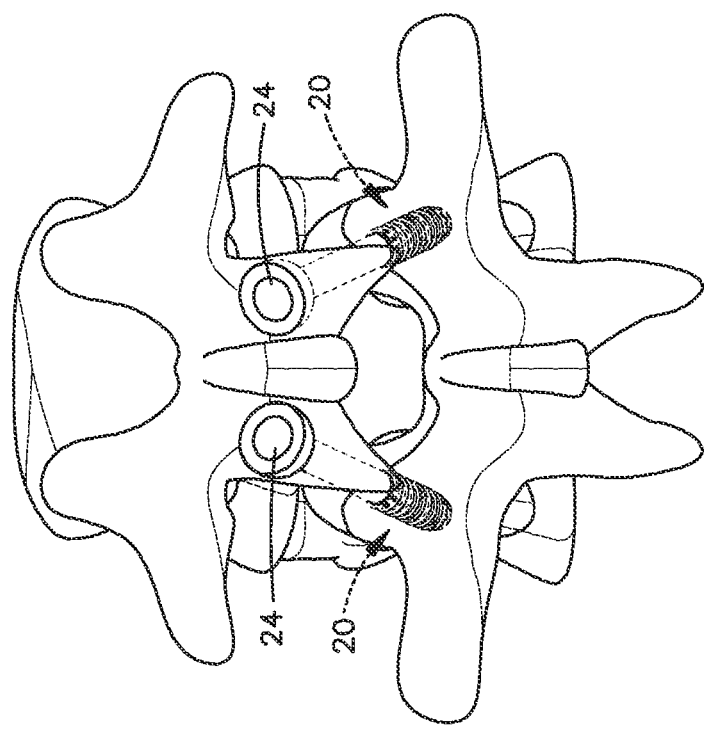
Figure 9O:
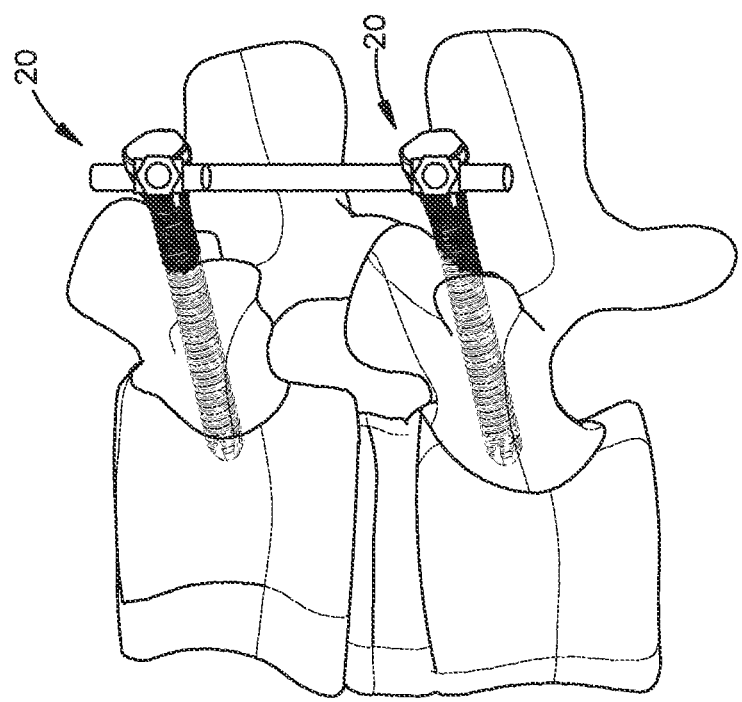
Figure 9N:
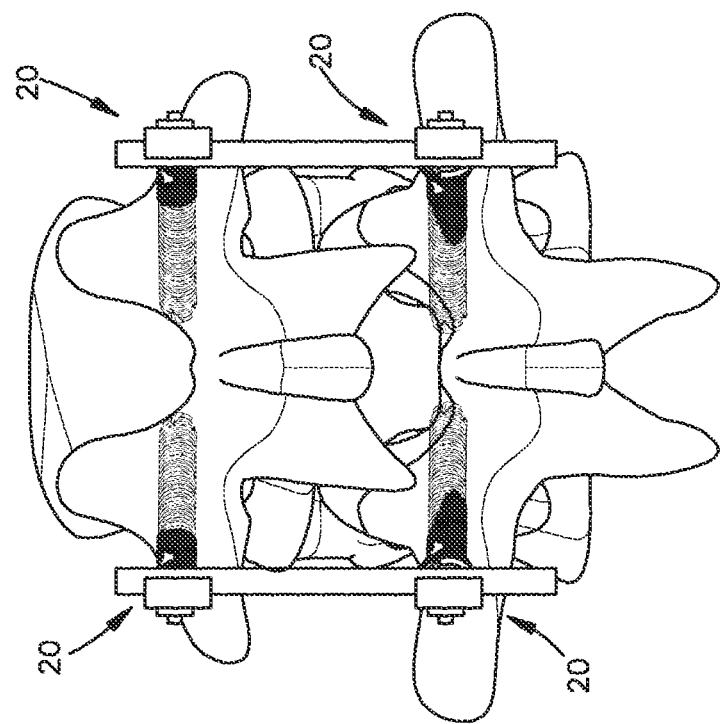

Referring now to FIGS. 9J-O, the expandable fixation assemblies 20 described herein can be used in spinal fixation procedures in place of typical fasteners used in such procedures such as bone screws, pedicle screws, and the like. For example expandable fixation assemblies 20 can be used in translaminar fixation as depicted in FIG. 9J, facet fixation as depicted in FIG. 9K, and pedicle/rod fixation constructs as depicted in FIG. 9L. Use of the expandable fixation assemblies 20 disclosed herein is desirable for deep recess procedures such as these because, unlike typical fasteners that can fall off the end of the insertion instrument, the expansion member 26 prevents the fixation member 24 from similarly falling off within the surgical site.

Referring now to FIGS. 9P-X, the expandable fixation assemblies 20 described herein can be used to anchor vertebral implants and/or spacers. For example, as depicted in FIGS. 9P-Q, a pair of fixation assemblies 20 are used to anchor an interspinous spacer 172 between adjacent spinous processes SP. The fixation members 24 may be inserted through the bores 80 in the bone plates 62 coupled to the spacer 172, and through pre-drilled bores 38 in the spinous processes SP. The mandrels 46 can then be pulled through the fixation members 24 as described above, thereby fixing the interspinous spacer 172 in place between the spinous processes SP. The inner surfaces of the bores 80 may be smooth, or may have anchoring geometries, such as threads 76, formed thereon, the anchoring geometries configured to engage complimentary engagement structures on the fixation members 24, such as threads 36.

Figure 9S:
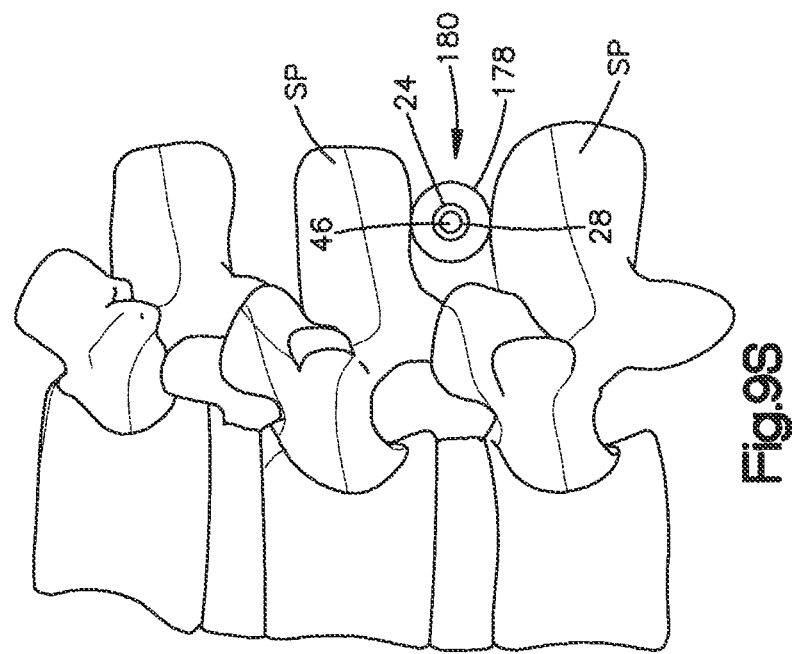
FIG. 9S is a side elevation view of an expandable interspinous spacer in accordance with an embodiment.
Figure 9R:
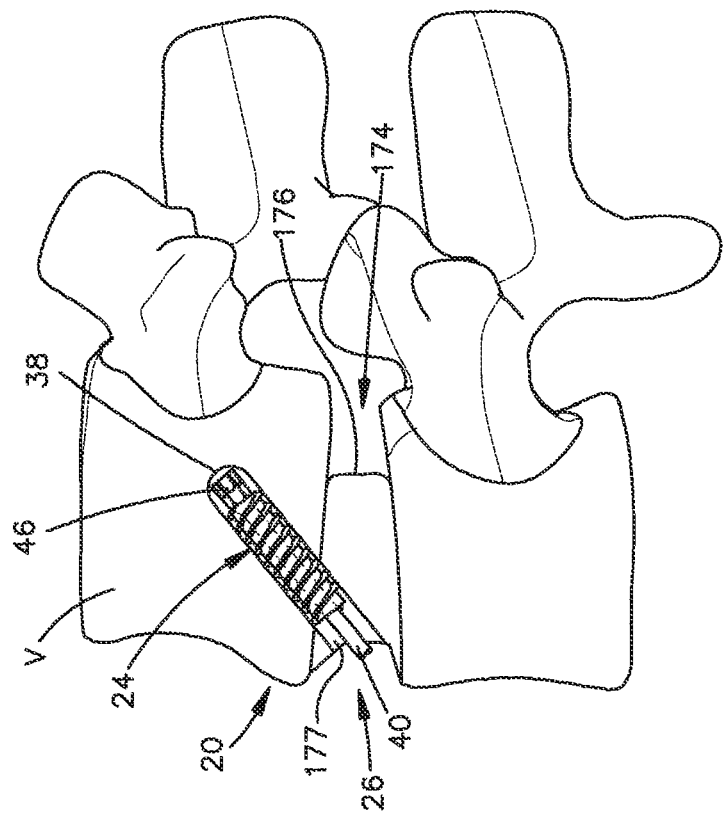
FIG. 9R is a side elevation view of an expandable fixation assembly inserted into an intervertebral implant in accordance with an embodiment.

In an alternative embodiment depicted in FIG. 9R, an expandable fixation assembly 20 is used to anchor an intervertebral implant 174 to an adjacent vertebral body V. The fixation member 24 is inserted through a bore 177 in the body 176 of the implant 174 and into a pre-drilled bore 38 in the adjacent vertebral body V. The mandrel 46 can then be pulled through the fixation member 24 as described above, thereby fixing the intervertebral implant 174 in place within the intervertebral space.

In still another alternative embodiment depicted in FIG. 9S, an expandable fixation member 24 is disposed within the body 178 of an interspinous spacer 180. The interspinous spacer 180 disposed within an interspinous space between two adjacent spinous processes SP. When the mandrel 46 is pulled through the shaft 28 of the fixation member 24, the shaft 28 expands radially outward, thereby expanding the body 178 of the interspinous spacer 180 within the interspinous space.

Figure 9T:
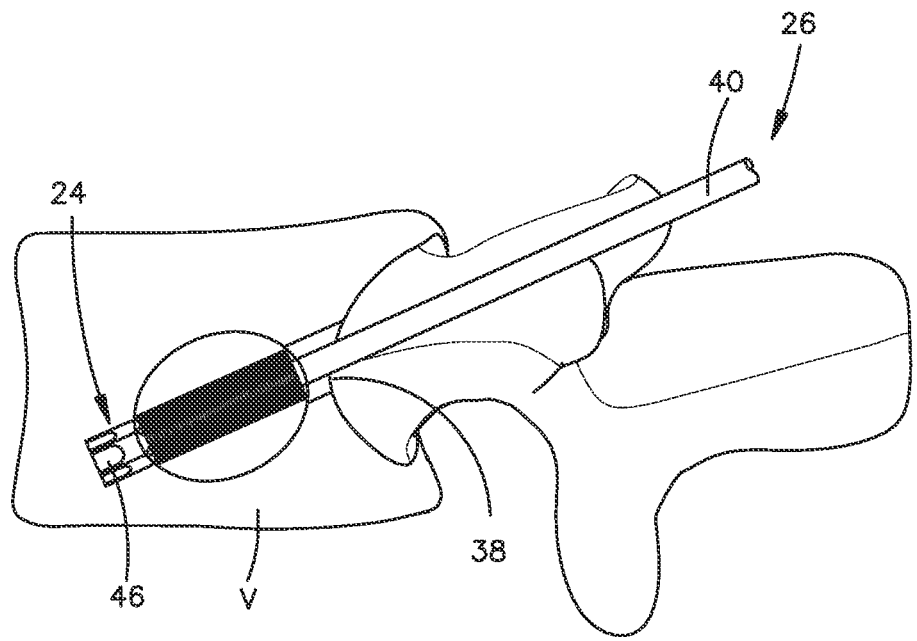
FIG. 9T is a side elevation view of an expandable vertebral stent in accordance with an embodiment, prior to expansion of the stent.
Figure 9U:
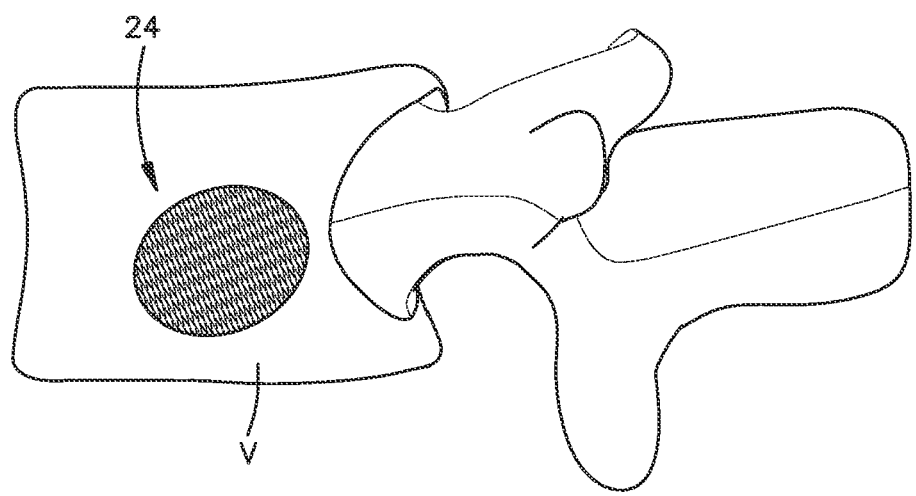
FIG. 9U is a side elevation view of the expandable vertebral stent illustrated in FIG. 9T, after expansion of the stent.

In yet another alternative embodiment depicted in FIGS. 9T-U, the fixation member 24 of an expandable fixation assembly 20 can be configured for used as a vertebral body stent. The expandable fixation assembly is disposed into a pre-drilled bore 38 within a vertebral body V. When the mandrel 46 is pulled through the shaft 28, the fixation member 24 expands radially outward, thereby stenting the vertebral body V.

In still another alternative embodiment depicted in FIGS. 9V-X, an expandable fixation assembly 20 can be used in a laminoplasty procedure. After the desired amount of material has been removed from the target lamina L, thereby creating a bore 38 in the lamina L, the fixation member 24 is disposed within the lamina L. As the mandrel 46 is pulled through the shaft 28, the fixation member 24 expands radially outward, thereby biasing the adjacent bone segments 22a-b of the lamina L outward, expanding the foramen, and causing the threads 36 on the outer surface of the shaft 28 of the fixation member 24 to engage with the surfaces of the adjacent bone segments 22a-b of the lamina L. It should be appreciated that the fixation member 24 and/or the expandable fixation assembly 20 can replace typical bone screws or other traditional anchors in any suitable surgical procedure as desired.

Referring now to FIGS. 10A-B, the fixation member 24 can be used for the purposes of grabbing and manipulating bone segments 22a-c, for instance of a mandible, into desired positions with respect to one or more adjacent bones or bone segments. In particular, the bore 38 can be drilled into the bone segment 22a, the distal end 34 of the shaft 28 can be inserted into the bore 38, and the mandrel 46 can be pulled into radial alignment with at least a portion of the expandable threads 36 such that the aligned threads 36 expand into the bone segment 22a. The shaft 40 of the expansion member 26 can then be used as a joystick, and can be manually maneuvered to manipulate the position of the bone segment 22a into a desired position. The bone segment 22a can then be fastened to the one or more adjacent bones or bone segments as desired. Once the bone segment 22a is securely fastened in place, a rotational force can be applied to the shaft 40 of the expansion member 26 in order to back the fixation member 24 out of the bore 38 for removal. Alternatively, the expansion member 26 can be pulled all the way through the shaft 28 so the fixation member 24 remains in the bore 38, for example if it is being used to hold a bone plate in place. These same steps can be applied to position the bone segments 22b-c for fixation. Fractures to which this method can be particularly applicable include but are not limited to subcondylar fractures, frontal sinus fractures, and the like.

Referring now to FIGS. 11A-B, the shaft 28 of the fixation member 24 can be axially divided into a plurality of circumferentially separated shaft segments, or legs, 28a-d. Thus, less force is required to pull the mandrel 46 through the shaft 28 since the mandrel encounters less resistance from the segmented shaft than it does from the circumferentially solid shaft 28 described above. The proximal end 30 of the fixation member 24 has a closed profile, such that the legs 28a-d are joined together at the proximal end 30 of the shaft 28. Accordingly, as the mandrel 46 is pulled into the bore 35 at the distal end 34 of the shaft 28, the outer surface of the mandrel 46 interferes with the inner surfaces of the legs 24a-d, causing the legs 28a-d to deflect radially outward, thereby causing the threads 36 on the outside surfaces of the legs 28a-d to bite into, or otherwise engage, the surrounding bone in the manner described above. Furthermore, after expansion, the shaft 40 of the expansion member 26 can be cut at a location aligned with, or recessed in, the proximal end 30 of the shaft, such that the mandrel 46 remains disposed in the bore 35 at a location aligned with the expanded threads 36, so as to maintain the biasing force of the mandrel 46 against the legs 28a-d, and thereby to maintain the engagement of the threads 36 with the surrounding bone.

Figure 12D:
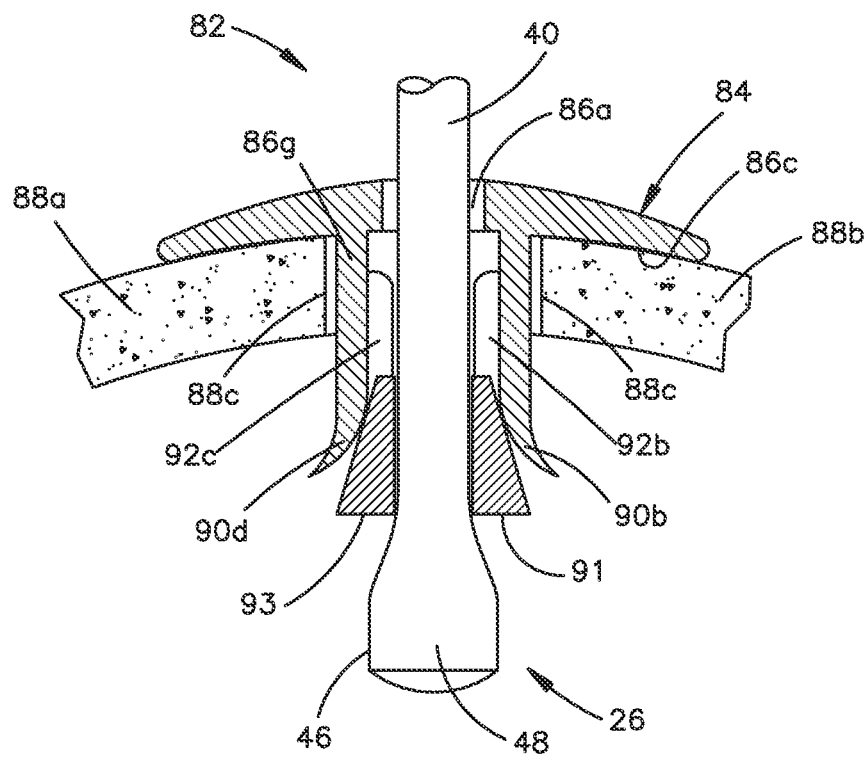
FIG. 12D is a sectional elevation view of the expandable cranial fixation assembly illustrated in FIG. 12B in accordance with an alternative embodiment, prior to expansion of the expandable cranial fixation member.

Referring now to FIGS. 12A-F, generally speaking, expandable fixation assemblies can be configured to secure two or more bone segments with respect to each other. For example, expandable fixation assemblies can be configured for use in cranial fixation procedures, for instance as expandable cranial fixation assemblies including expandable cranial fixation members configured as expandable cranial clamps for use in securing bone flaps in craniotomies. In general, expandable cranial fixation members such as cranial clamps can be configured using a variety of expandable fixation member bodies, as described in more detail below. In particular, as illustrated in FIGS. 12A-C, an expandable cranial fixation assembly 82 includes an expandable fixation member such as cranial clamp 84, and an expansion member 26. The cranial clamp 84 includes an expandable fixation member body, such as disc shaped body 86, the body 86 having a central aperture 86a with an inner diameter ID3 formed therethrough. The body 86 has an upper surface 86*b*, and an opposing lower surface 86*c*. The upper and lower surfaces 86*b* and 86*c*, respectively, can be configured to conform to a particular anatomical region, for example a particular area on the outer surface of the skull, so as to maximize contact between the lower surface 86*c* and underlying bone segments 88*a* and 88*b*, while simultaneously minimizing the profile of the upper surface 86*b* with respect to the outer surface of the bone segments 88*a* and 88*b*. In the illustrated embodiment, the upper surface 86*b* is convex, and the opposing lower surface 86*c* is concave. In an alternative embodiment, one or more of the upper and lower surfaces 86*b* and 86*c* can be flat. It should be noted that any alternative body geometry, surface profile, and/or aperture locations could be used as desired.

The body 82 of the cranial clamp 84 further includes a ductile cannulated shaft 86*d* having a proximal end 86*e* and an opposing distal end 86*f*, the shaft 86*d* extending in a downward, or caudal, direction from the proximal end 86*e* at the lower surface 86*c* along a central shaft axis S, the thickness of the shaft 86*d* defined by an outer diameter OD3 that is greater than, and an inner diameter ID4 that is smaller than, the inner diameter ID3 of the aperture 86*a*. Although the illustrated embodiment depicts the shaft 86*d* as having a uniform thickness between the proximal and distal ends 86*e* and 86*f*, it should be appreciated that the outer diameter OD3 and/or the inner diameter ID4 can be tapered, or otherwise varied, along one or more sections, or along the entirety, of the length of the shaft 86*d* between the proximal and distal ends 86*e* and 86*f*, respectively. The inner diameter ID4 may also be slightly smaller than the outer dimension of the outer surface 48 of the mandrel 46. The shaft 86*d* is divided into a plurality of radially separated shaft segments, or legs, 90*a-d*, for example by axial slots 92*a-d*. The slots begin at the distal end 86*f* of the shaft 86*d* and extend in an upward, or cranial, direction into the shaft, terminating in a circumferentially solid portion 86*g* of the shaft 86*d*. Although the illustrated embodiment has four axial slots defining four corresponding legs, any corresponding number of axial slots may be used to define a desired number of legs.

During use, the cranial fixation assembly 82 can be used to secure bone segments 88*a* and 88*b*, for example a bone flap that is being rejoined to a patient's skull. A plurality of cranial fixation assemblies 82 may be disposed within the gap between the bone flap and the skull at various locations along the perimeter of the bone flap as desired. Once a respective cranial fixation assembly 82 is disposed in a desired location, a downward, or caudal, biasing force is applied to the upper surface 86*b* of the cranial clamp 84, for example by an insertion instrument. An upward, or cranial, force is applied to the elongate shaft 40 of the expansion member 26, in the direction of arrow M, thereby drawing the mandrel 46 into the distal end 86*f* of the shaft 86*d*. As the mandrel 46 enters the distal end 86*f* of the shaft 86*d*, the outer surface 48 of the mandrel 46 interferes with the distal ends of the legs 90*a-d*, causing the legs to deflect outwardly from the advancing mandrel 46. The degree of curvature exhibited by the legs 90*a-d* may result from, for example, the radial thickness of the legs as defined by the outer and inner diameters OD3 and ID4 of the shaft 86*d*, the difference between the inner diameter ID4 of the shaft 86*d* and the outer dimension of the outer surface 48 of the mandrel 46, the material of manufacture of the cranial clamp 84, the speed with which the mandrel 46 is advanced within the shaft 86*d*, and other such factors. The deformation characteristics of the legs 90*a-d* may be tuned via variation of one or more of the above, and/or similar factors.

As the mandrel continues to travel upward within the shaft 86*d*, it leaves the portion of the shaft 86*d* including the legs 90*a-d* and enters the circumferentially solid portion 86*g* of the shaft 86*d* beyond the proximal ends of the slots 92*a-d*. The curvature imparted to the legs 90*a-d* may cause the outer surface of one or more of the legs 90*a-d* to engage the inner surface of the bone segments 88*a* and 88*b* in proximity to the edges 88*c*, thereby drawing the lower surface 86*c* of the cranial implant 84 against the outer surfaces of the bone segments 88*a* and 88*b*, and imparting a compressive, or clamping, force onto the surfaces of the bone segments 88*a* and 88*b* disposed between the lower surface 86*c* of the cranial implant 84 and the outer surface of the legs 90*a-d*.

As the mandrel 46 passes through the circumferentially solid portion 86*g* of the shaft 86*d* and out of the aperture 86*a*, the shaft 86*d* may expand radially outward, thereby augmenting the outer and inner diameters OD3 and ID4, respectively. The outer diameter OD3 may be augmented such that the outer surface of the circumferentially solid portion 86*g* of the shaft 86*d* engages at least a portion of the edges 88*c* of the bone segments 88*a* and 88*b*, inducing a friction fit of the cranial clamp 84 within the gap between the bone segments 88*a* and 88*b*. Additionally, the inner surface of the shaft 86*d* and/or the aperture 86*a* may deform to conform to the shape of the outer surface 48 of the mandrel 46.

Figure 12E:
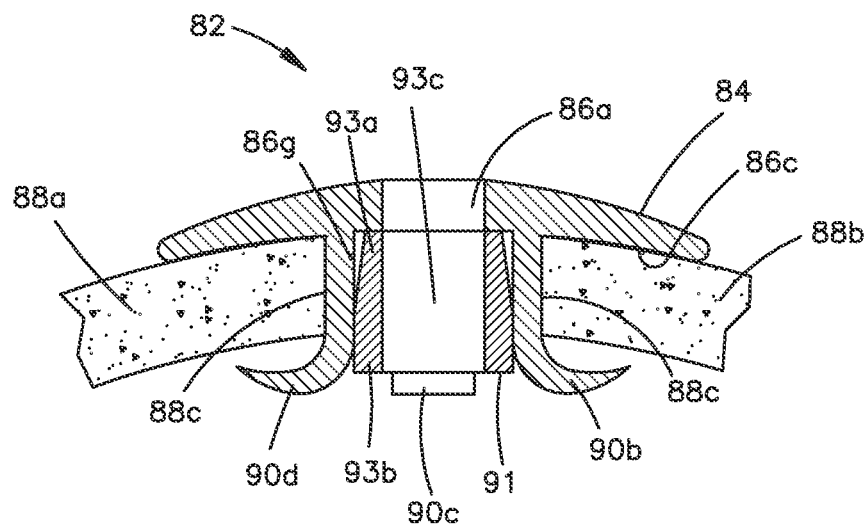
FIG. 12E is a sectional elevation view of the expandable cranial fixation assembly illustrated in FIG. 12D, after expansion of the expandable cranial fixation member.

In an alternative embodiment as depicted in FIGS. 12D-E, the cranial fixation assembly 82 further includes a retention structure, for example a retaining plug 91. The retaining plug 91 is configured to ensure retention of the cranial clamp 84 between the bone segments 88*a* and 88*b* after the mandrel 46 has been pulled through the shaft 86*d*. The retaining plug 91 has a generally conical shaped body 93 defined between a proximal end 93*a* and an opposing distal end 93*b*. The diameter of the body 93 at the proximal end 93*a* is slightly smaller than the inner diameter ID4 of the shaft 86*d*. The diameter of the body 93 increases gradually between the proximal end 93*a* and the distal end 93*b*. The retaining plug 91 has an axial bore 93*c* formed therethrough, the axial bore 93*a* having an inner diameter that is slightly smaller than the outer dimension of the outer surface 48 of the mandrel 46. The inner diameter ID4 of the shaft 86*d* may be enlarged so that the retaining plug 91 can be received in the shaft 86*d* as the mandrel 46 is pulled therethrough. Additionally, the distal ends of the legs 90*a-d* can be tapered, flared, or otherwise configured to facilitate engagement between the legs 90*a-d* and the outer surface of the retaining plug 91 as it enters the shaft 86*d*. The retaining plug 91 can be inserted onto the expansion member 26 and disposed within the cranial clamp 84 before the cranial fixation assembly 82 is disposed into a surgical site.

During use, as the mandrel 46 enters the distal end of the axial bore 93*c* of the retaining plug 91, the outer surface 48 of the mandrel 46 interferes with the inner surface of the axial bore 93*c*, causing the retaining plug 91 to be drawn upward into the shaft 86*d*. As the retaining plug 91 advances into the shaft 86*d*, the outer surface of the retaining plug interferes with the distal ends of the legs 90*a-d*, causing the legs to deflect outwardly from the advancing retaining plug 91 and to engage the inner surface of the bone segments 88*a* and 88*b* in proximity to the edges 88*c*, thereby resulting in a clamping force applied to the bone segments 88*a* and 88*b* as described above. The advancing retaining plug 91 can also cause radial expansion of the shaft 86*d*, thereby causing the outer surfaces of one or more of the legs 90*a-d* to engage the edges 88*c* of the bone segments 88*a* and 88*b*, thereby inducing a friction fit of the cranial clamp 84 within the gap between the bone segments 88a and 88b. As the retaining plug 91 enters the circumferentially solid portion 86g of the shaft 86d, the forces between the retaining plug and the legs 90a-d can activate the legs 90a-d into a locked configuration.

Figure 12F:
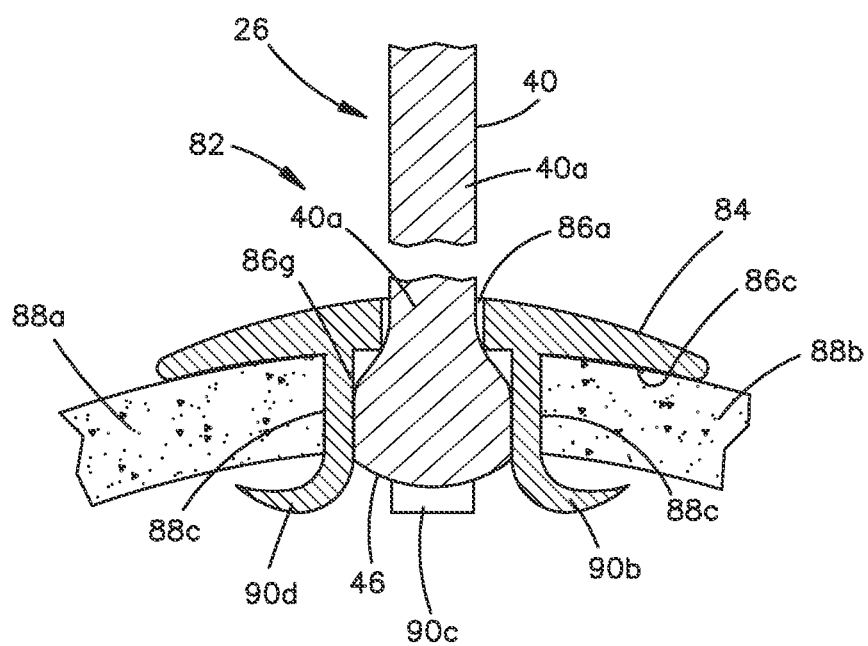
FIG. 12F is a sectional elevation view of the expandable cranial fixation assembly illustrated in FIG. 12B in accordance with still another alternative embodiment, after expansion of the expandable cranial fixation member.

In still another alternative embodiment depicted in FIG. 12F, the mandrel 46 can be configured to act as a retaining plug. For example, the mandrel 46 could have a narrow, or "necked in," section 40a, the diameter, or other outer dimension of the narrow section 40a configured to break when a desired level of biasing stress is reached in the shaft 40. In the illustrated embodiment, as the mandrel 46 is pulled into the circumferentially solid portion 86g of the shaft 86d, the biasing stress would cause the shaft 40 of the expansion member 26 to break at the narrow section 40a, thereby leaving the mandrel 46 disposed within the shaft 86d, to act as a retaining plug to activate the legs 90a-d into a locked configuration.

Figure 13A:
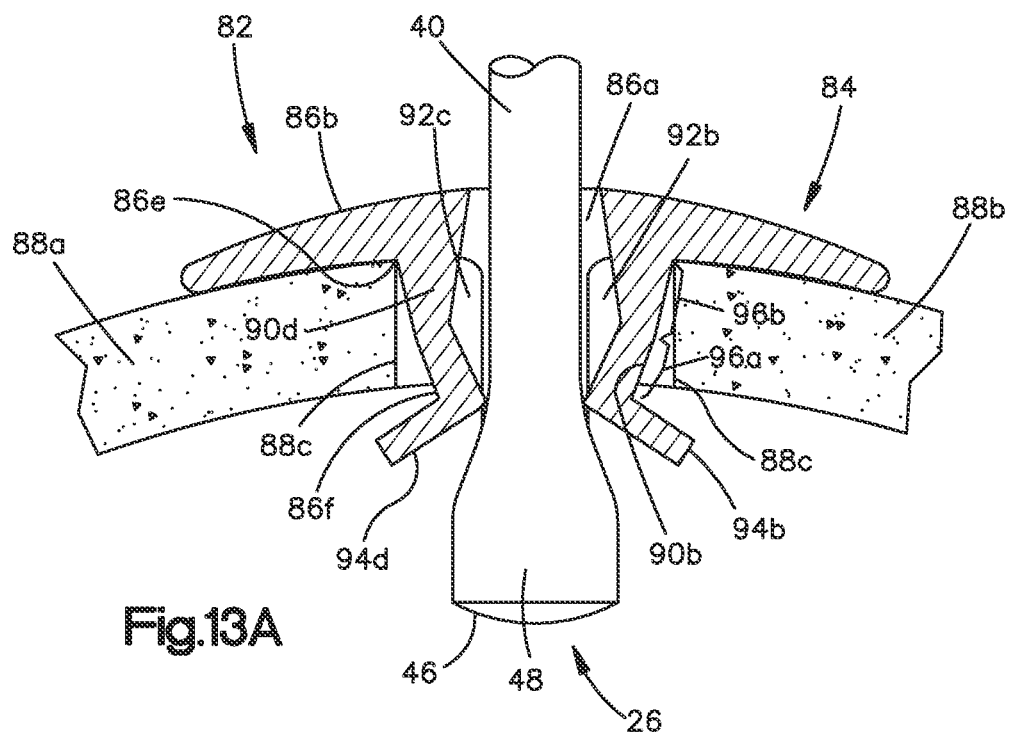
FIG. 13A is a sectional elevation view of an expandable cranial fixation assembly in accordance with an alternative embodiment, prior to expansion of the expandable cranial fixation member.
Figure 13B:
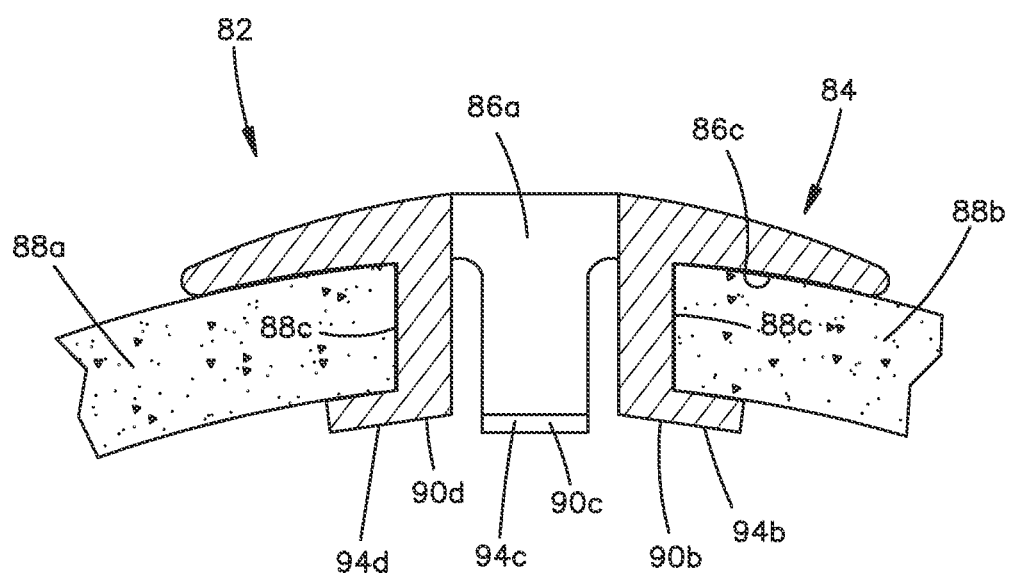
FIG. 13B is a sectional elevation view of the expandable cranial fixation assembly illustrated in FIG. 13A, after expansion of the expandable cranial fixation member.

Referring now to FIGS. 13A-B, the cranial fixation assembly 82 and the cranial clamp 84 are illustrated in accordance with another embodiment. In the illustrated embodiment, the axial slots 92a-d extend along the entire length of the shaft 86d between the proximal and distal ends 86e and 86f, respectively. The thickness of the legs 90a-d, as defined by the outer and inner diameters OD3 and ID4 of the shaft 86d, can be varied over at least of a portion of the length of the shaft 86d between the proximal and distal ends 86e and 86f thereof. Varying the thickness of the legs 90a-d may determine the deformation behavior of the legs 90a-d as the mandrel 46 is advanced in the shaft 86d, as explained in more detail below. In the illustrated embodiment, the thickness of the legs 90a-b is uniform throughout a first intermediate section 96a of the length to the shaft 86d that begins at the distal end 86f of the shaft and extends in an upward direction into the shaft 86d. In a second intermediate section 96b, extending between the end of the first intermediate section 96a and the proximal end 86e of the shaft 86, the thickness of the legs 90a-d gradually increases, and is greatest at the proximal end 86e of the shaft 86d. Additionally, the distal ends of the legs 90a-d include bone engagement structures, such as feet 94a-d, formed at the distal ends thereof, the feet configured to engage the bone segments 88a and 88b.

During use, the illustrated embodiment of the cranial fixation assembly 82 can be used to secure bone segments 88a and 88b. Once a respective cranial fixation assembly 82 is disposed in a desired location, a downward, or caudal, biasing force is applied to the upper surface 86b of the cranial clamp 84, for example by an insertion instrument. An upward, or cranial, force is applied to the elongate shaft 40 of the expansion member 26, thereby drawing the mandrel 46 into the distal end 86f of the shaft 86d. As the mandrel 46 enters the distal end 86f of the shaft 86d and advances into the first intermediate portion 96a, the outer surface 48 of the mandrel 46 interferes with the distal ends of the legs 90a-d, causing the legs to deflect outwardly from the advancing mandrel 46. Furthermore, the deflection of the legs 90a-d can cause the upper surfaces of the feet 94b and 94d to engage with the lower, or inner, surfaces of the bone segments 88a and 88b, thereby drawing the lower surface 86c of the cranial implant 84 against the outer surfaces of the bone segments 88a and 88b, and imparting a compressive, or clamping, force onto the surfaces of the bone segments 88a and 88b disposed between the lower surface 86c of the cranial implant 84 and the upper surfaces of the feet 94b and 94d.

As the mandrel 46 advances further into the shaft 86d, and into the second intermediate portion 96b, the legs 90a-d may continue to deflect from the mandrel 46, and the increasing thickness of the legs 90a-d in the second intermediate portion 96b may cause the shaft 86d to expand radially outward as described above, causing the outer surfaces of one or more of the legs 90a-d to engage the edges 88c of the bone segments 88a and 88b, thereby inducing a friction fit of the cranial clamp 84 within the gap between the bone segments 88a and 88b. It should be appreciated that while the illustrated embodiment depicts engagement by only the feet 94b and 94d, the feet 94a-d can be so configured, and the cranial fixation assembly 82 can be so oriented during insertion, that any combination of one or more, including all, of the feet 94a-d engage the lower surfaces and/or the edges 88c of the bone segments 88a and 88b as the mandrel 46 is pulled through the shaft 86d.

Referring now to FIGS. 14A-D, the cranial fixation assembly 82 and the cranial clamp 84 are illustrated in accordance with still another embodiment. In the illustrated embodiment, the axial slots 92a-d are defined along a portion of the length of the shaft 86d between opposing circumferentially solid portions 86g located at the proximal and distal ends 86e and 86f of the shaft 86d, respectively. The sections of the shaft 86d defined between the opposing circumferentially solid portions 86g and the axial slots 92a-d can be hinged in one or more locations along their respective lengths, forming one or more jointed legs sections of jointed legs 98a-d. The jointed legs 98a-d can be configured to define one or more bone engagement structures, such as cutting tips 100a-d, the cutting tips 100a-d configured to cut into underlying structure of the bone segments 88a and 88b. In the embodiment illustrated in FIGS. 14A-B, the jointed legs 98a-d are of such a length that when the cranial clamp 84 is disposed within a surgical site, the cutting tips 100a-d define radial insertion trajectories that approximately bisect the edges 88c of the bone segments 88a and 88b. Such trajectories can be used to direct the cutting tips into cancellous bone. In the alternative embodiment illustrated in FIGS. 14C-D, the jointed legs 98a-d are of such a length that when the cranial clamp 84 is disposed within a surgical site, the cutting tips 100a-d define insertion trajectories into the lower, or inner, surfaces of the bone segments 88a and 88b. It should be appreciated that the jointed legs 98a-d can be configured so as to define any alternate insertion trajectory into the bone segments 88a and 88b as desired.

Figure 14A:
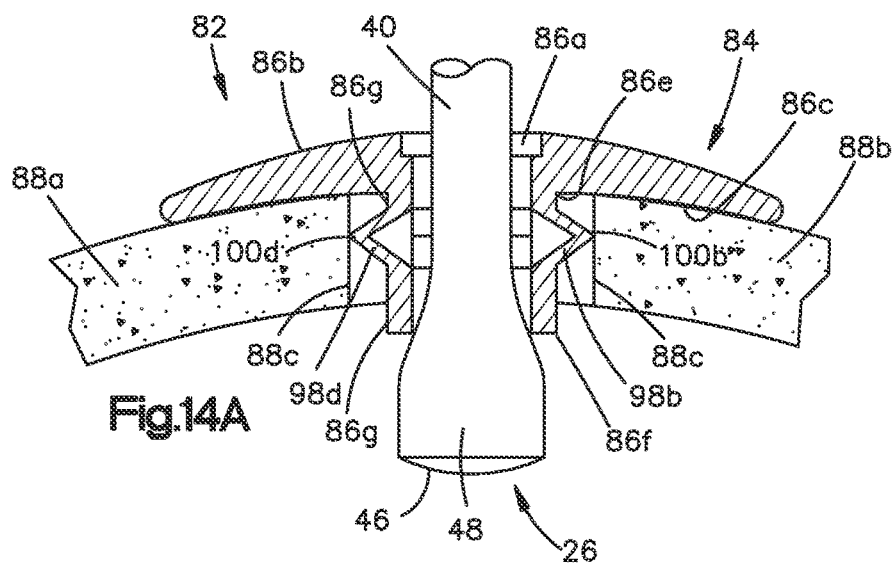
FIG. 14A is a sectional elevation view of an expandable cranial fixation assembly in accordance with an alternative embodiment, prior to expansion of the expandable cranial fixation member.
Figure 14B:
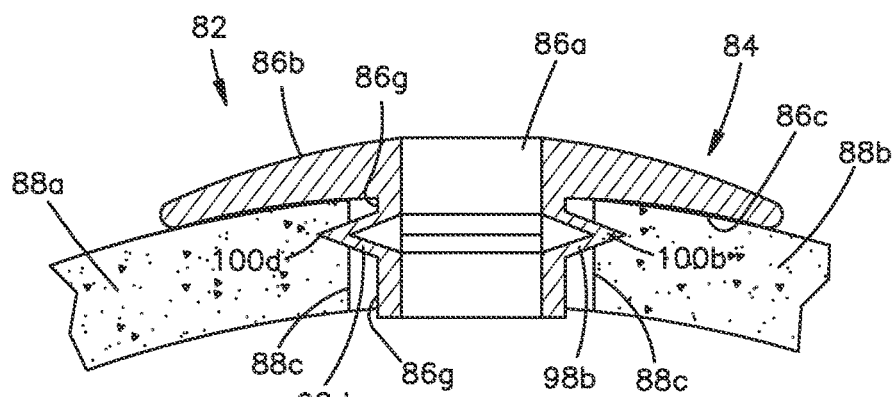
FIG. 14B is a sectional elevation view of the expandable cranial fixation assembly illustrated in FIG. 14A, after expansion of the expandable cranial fixation member.
Figure 14C:
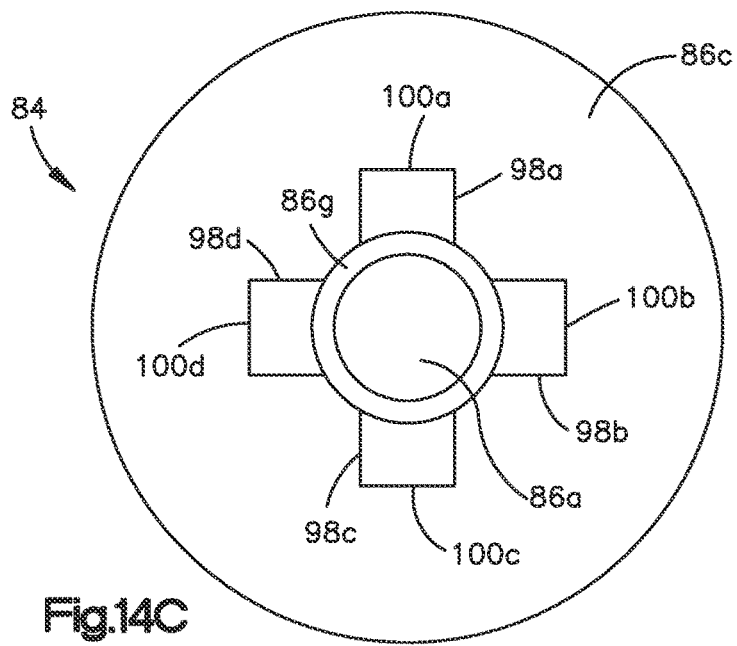
FIG. 14C is a bottom elevation view of the expandable cranial fixation assembly illustrated in FIG. 14A.
Figure 14D:
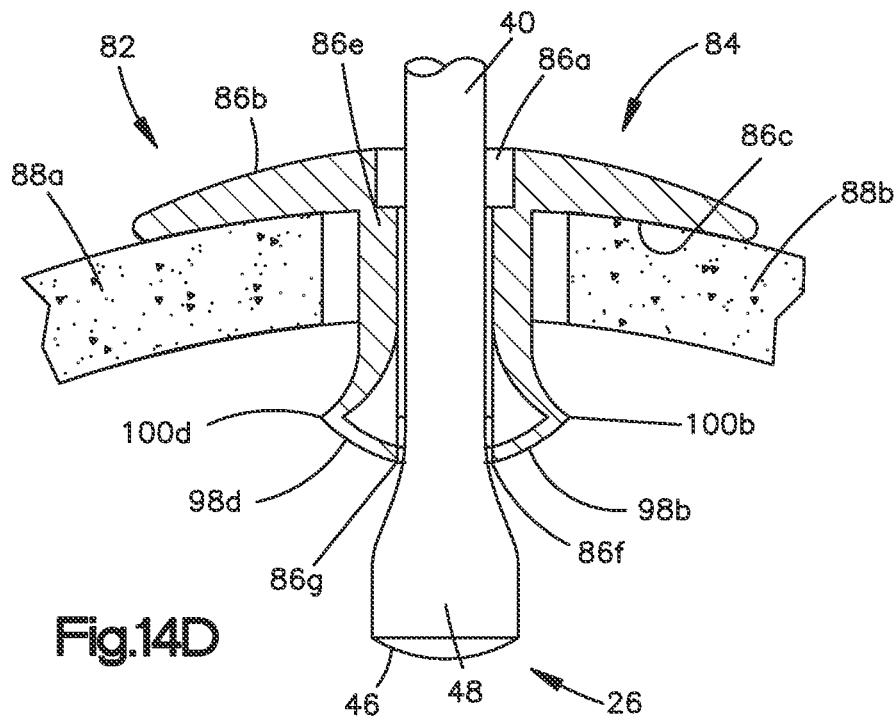
FIG. 14D is a sectional elevation view of the expandable cranial fixation assembly illustrated in FIG. 14A in accordance with an alternative embodiment, prior to expansion of the expandable cranial fixation member.
Figure 14E:
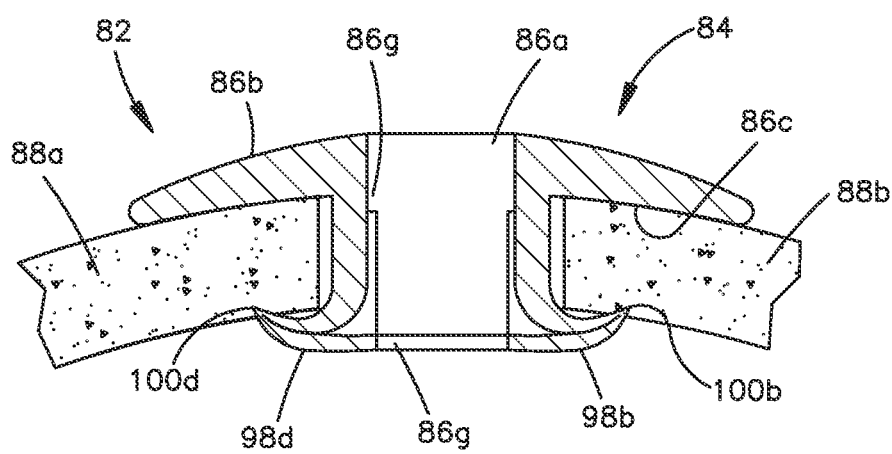
FIG. 14E is a sectional elevation view of the expandable cranial fixation assembly illustrated in FIG. 14D, after expansion of the expandable cranial fixation member.

During use, the illustrated embodiments of the cranial fixation assembly 82 can be used to secure bone segments 88a and 88b. Once a respective cranial fixation assembly 82 is disposed in a desired location, a downward, or caudal, biasing force is applied to the upper surface 86b of the cranial clamp 84, for example by an insertion instrument. An upward, or cranial, force is applied to the elongate shaft 40 of the expansion member 26, thereby drawing the mandrel 46 into the distal end 86f of the shaft 86d. As the mandrel 46 enters the distal end 86f of the shaft 86d, the outer surface 48 of the mandrel 46 interferes with the lower of the opposing circumferentially solid portions 86g, causing the jointed legs 98a-d to collapse in upon each other, thereby driving the cutting tips 100b and 100d into the bone segments 88a and 88b, as depicted in FIG. 14B or 14D. As the mandrel 46 advances further into the shaft 86d and the cutting tips 100b and 100d are driven further into the bone segments 88a and 88b, thereby anchoring the cranial clamp 84 within the gap between the bone segments 88a and 88b. Additionally, the continued collapsing of the jointed legs 98a-d can draw the lower surface 86c of the cranial implant 84 against the outer surfaces of the bone segments 88*a* and 88*b*, imparting a compressive, or clamping, force between the upper surfaces of the bone segments 88*a* and 88*b* engaged by the lower surface 86*c* of the cranial implant 84 and the jointed legs 98*b* and 98*d*. It should be appreciated that while the illustrated embodiment depicts only the cutting tips 100*b* and 100*d* engaging the bone segments 88*a* and 88*b*, the jointed legs 98*a*-*d* can be so configured, and the cranial fixation assembly 82 can be so oriented during insertion, that any combination of one or more, including all, of the cutting tips 100*a*-*d* cut into the bone segments 88*a* and 88*b* as the mandrel 46 is pulled through the shaft 86*d*.

Figure 15A:
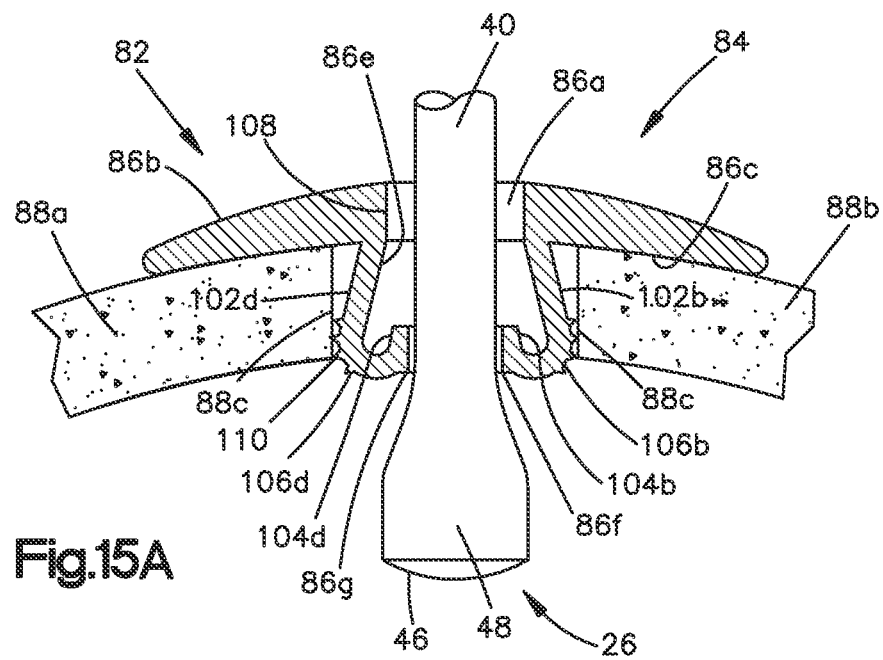
FIG. 15A is a sectional elevation view of an expandable cranial fixation assembly in accordance with an alternative embodiment, prior to expansion of the expandable cranial fixation member.
Figure 15B:
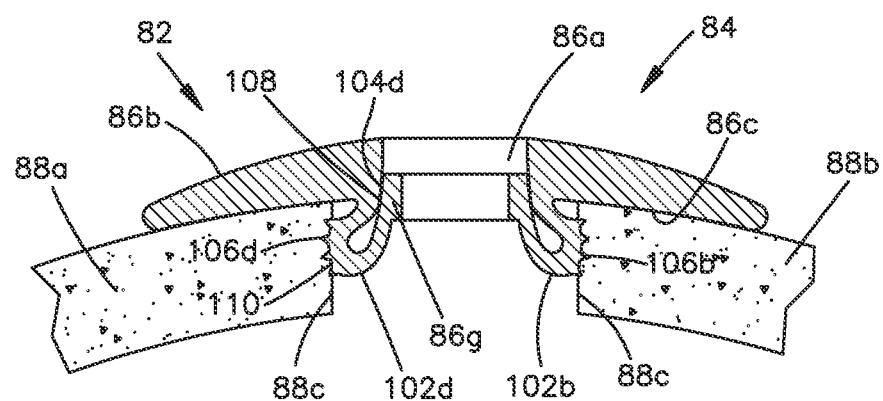
FIG. 15B is a sectional elevation view of the expandable cranial fixation assembly illustrated in FIG. 15A, after expansion of the expandable cranial fixation member.
Figure 15C:
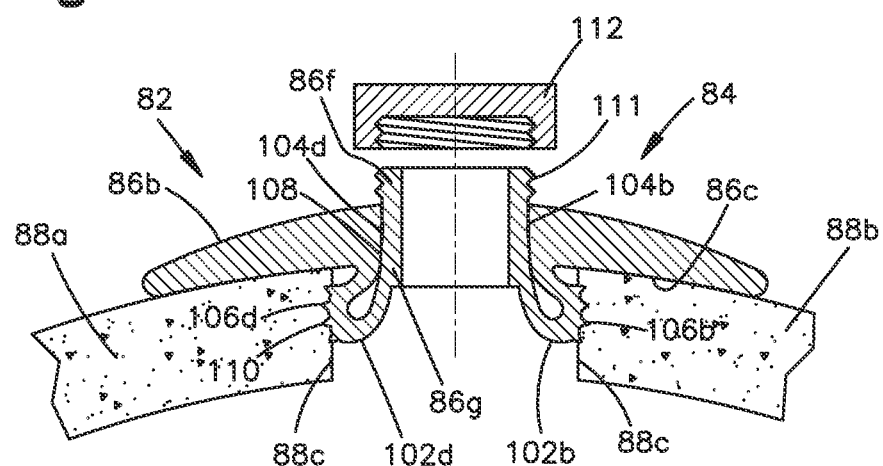
FIG. 15C is a sectional elevation view of the expandable cranial fixation assembly illustrated in FIG. 15A in accordance with an alternative embodiment, after expansion of the expandable cranial fixation member.

Referring now to FIGS. 15A-C, the cranial fixation assembly 82 and the cranial clamp 84 are illustrated in accordance with yet another embodiment. In the illustrated embodiment, the axial slots 92*a*-*d* are defined along a portion of the length of the shaft 86*d* between the lower surface 86*c* of the cranial cap 84 and an opposing circumferentially solid portion 86*g* located at the distal end 86*f* of the shaft 86*d*, respectively. Each of flexible legs 102*a*-*d*, defined by the axial slots 92*a*-*d*, extend in a downward, or caudal, direction from the lower surface 86*c*, bend back upon themselves to form engagement loops 106*a*-*d*, and terminate in the circumferentially solid portion 86*g*, forming exterior collar surfaces 104*a*-*d*, the collar surfaces 104*a*-*d* configured to engage with a neck 108 defined at the proximal end 86*e* of the shaft 86*d*. The outer surface of the engagement loops 106*a*-*d* have one or more bone engagement structures formed thereon, such as teeth 110, the teeth 110 configured to cut into underlying structure of the bone segments 88*a* and 88*b*.

During use, the illustrated embodiment of the cranial fixation assembly 82 can be used to secure bone segments 88*a* and 88*b*. Once a respective cranial fixation assembly 82 is disposed in a desired location, a downward, or caudal, biasing force is applied to the upper surface 86*b* of the cranial clamp 84, for example by an insertion instrument. An upward, or cranial, force is applied to the elongate shaft 40 of the expansion member 26, thereby drawing the mandrel 46 into the distal end 86*f* of the shaft 86*d*. As the mandrel 46 enters the distal end 86*f* of the shaft 86*d*, the outer surface 48 of the mandrel 46 interferes with the circumferentially solid portion 86*g*, causing the circumferentially solid portion 86*g* to be drawn upward and causing the flexible legs 102*a*-*d* to collapse upon themselves such that the teeth 110 of the engagement loops 106*b* and 106*d* engage the bone segments 88*a* and 88*b*, cutting into the edges 88*c* thereof.

As the mandrel 46 advances further, the teeth 110 are driven further into the edges 88*c* of the bone segments 88*a* and 88*b*, thereby anchoring the cranial clamp 84 within the gap between the bone segments 88*a* and 88*b*. Additionally, the collapsing of the flexible legs 102*a*-*d* can draw the lower surface 86*c* of the cranial implant 84 against the outer surfaces of the bone segments 88*a* and 88*b*, imparting a compressive, or clamping, force between the upper surfaces of the bone segments 88*a* and 88*b* engaged by the lower surface 86*c* of the cranial implant 84 and the flexible legs 102*b* and 102*d*. As the mandrel 46 advances near the aperture 86*a* at the proximal end 86*e* of the shaft, the collar surfaces 104*a*-*d* can engage the inner surfaces of the neck 108, thereby creating a friction force that activates the flexible legs 102*a*-*d* into a locked configuration.

In an alternative embodiment depicted in FIG. 15C, the circumferentially solid portion 86*g* is of sufficient length that it protrudes from the aperture 86*a* when the mandrel 46 has been pulled through the shaft 86*d*. The protruding portion of the circumferentially solid portion 86*g* can have helical threads 111 formed along its outer surface at the distal end 86*f* of the shaft 86*d*, the threads 111 configured to engage with complimentary threads of a locking nut 112. The locking nut 112 can be installed on the distal end 86*f* of the shaft 86*d* in order to prevent the collar surfaces 104*a*-*d* of the circumferentially solid portion 86*g* from backing out of the neck 108, thereby activating the flexible legs 102*a*-*d* to an unlocked configuration. It should be appreciated that while the illustrated embodiment depicts only the engaging loops 106*b* and 106*d* engaging the bone segments 88*a* and 88*b*, the flexible legs 102*a*-*d* can be so configured, and the cranial fixation assembly 82 can be so oriented during insertion, that any combination of one or more, including all, of the engagement loops 106*a*-*d* engage the bone segments 88*a* and 88*b* as the mandrel 46 is pulled through the shaft 86*d*. If it is subsequently desired to distract the cranial clamp 84 from a surgical site, the flexible legs 102*a*-*d* can be activated to an unlocked configuration by depressing the circumferentially solid portion 86*g* downward and out of the neck 108 (having first removed the locking nut 112 if applicable). When the flexible legs 102*a*-*d* are in the unlocked configuration, the cranial clamp 84 can be removed.

Referring now to FIGS. 16A-G, the cranial fixation assembly 82 and the cranial clamp 84 are illustrated in accordance with still another embodiment. In the illustrated embodiment, the shaft 86*d* is circumferentially solid along its entire length between the proximal and distal ends 86*e* and 86*f*, respectively. The body 86 of the cranial clamp 84 further includes a bottom disc 86*h* formed at the distal end 86*f* thereof. The bottom disc 86*h* can have one or more bone engagement structures extending radially therefrom, such as points 114, the points 114 configured to cut into or otherwise engage with the bone segments 88*a* and 88*b* as described in more detail below. In the illustrated embodiment, five points 114 are spaced apart equally around the circumference of the bottom disc 86*h*, but more or less points 114 could be circumferentially arranged in any pattern on the bottom disc 86*h* as desired. The outer surface of the shaft may have optional bone engagement structures, such as teeth 116, formed thereon, the teeth 116 configured to engage the edges 88*c* of the bone segments 88*a* and 88*b*. The thickness of the shaft 86*d*, defined by the outer and inner diameters OD3 and ID4 of the shaft 86*d*, can be configured to allow varying degrees of axial compression as the mandrel 46 is pulled though of the shaft 86*d*. A greater degree of axial compression allows the shaft 86*d* of the cranial clamp 84 to be manufactured in such a length that the cranial fixation system 82 can be utilized to secure bone segments of a variety of thicknesses.

During use, the cranial fixation assembly 82 can be used to secure bone segments 88*a* and 88*b*. Once a respective cranial fixation assembly 82 is disposed in a desired location, a downward, or caudal, biasing force is applied to the upper surface 86*b* of the cranial clamp 84, for example by an insertion instrument. An upward, or cranial, force is applied to the elongate shaft 40 of the expansion member 26, thereby drawing the mandrel 46 into the distal end 86*f* of the shaft 86*d*. In the embodiment depicted in FIGS. 16A-B, as the mandrel 46 enters the distal end 86*f* of the shaft 86*d*, the outer surface 48 of the mandrel 46 interferes with the inner surface of the shaft 86*d*, causing the shaft 86*d* to compress axially towards the proximal end 86*e* and/or to expand radially outward as described above. Axial compression of the shaft 86*d* causes the points 114 to be drawn upwards and to engage with the lower surfaces of the bone segments 88*a* and 88*b*, thereby drawing the lower surface 86*c* of the cranial implant 84 against the outer surfaces of the bone segments 88a and 88b, and imparting a compressive, or clamping, force onto the surfaces of the bone segments 88a and 88b disposed between the lower surface 86c of the cranial implant 84 and the points 114. Radial expansion of the shaft 86d can cause the outer surface of the shaft 86d, and optional teeth 116 if present, to engage the edges 88c of the bone segments 88a and 88b, thereby inducing a friction fit of the cranial clamp 84 within the gap between the bone segments 88a and 88b. It should be appreciated that the lower disc 86h can be formed without the points 114, for example to augment the amount of available surface area of the lower disc 86h for engaging with the lower surfaces of the bone segments 88a and 88b.

Figure 16A:
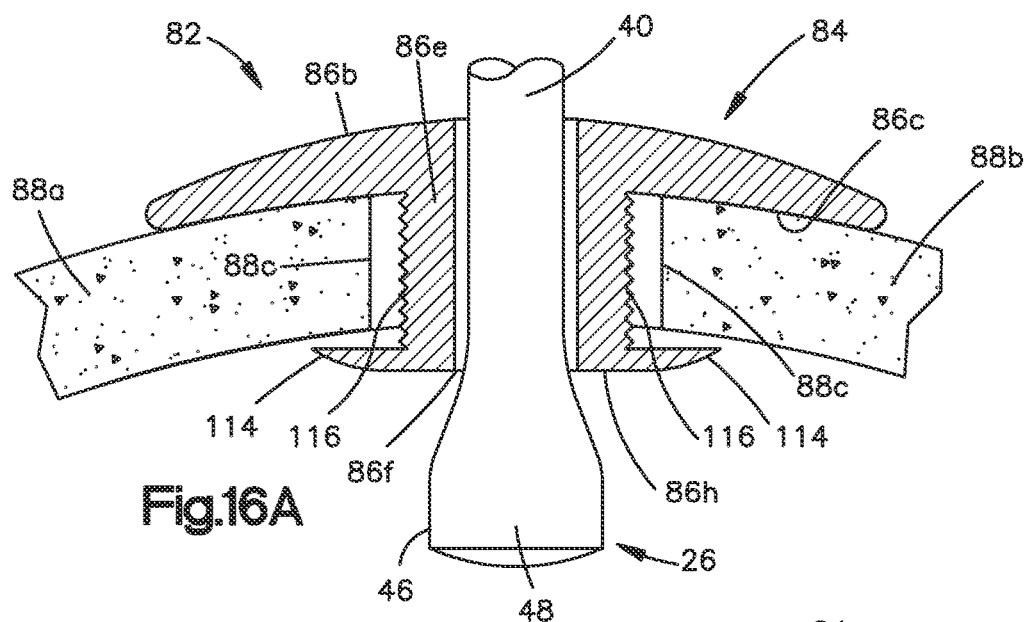
FIG. 16A is a sectional elevation view of an expandable cranial fixation assembly in accordance with an alternative embodiment, prior to expansion of the expandable cranial fixation member.
Figure 16B:
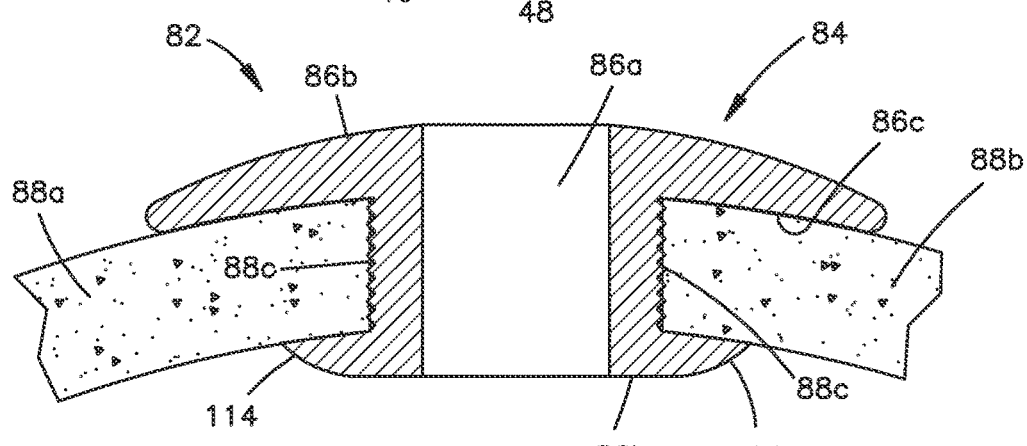
FIG. 16B is a sectional elevation view of the expandable cranial fixation assembly illustrated in FIG. 16A, after expansion of the expandable cranial fixation member.
Figure 16C:
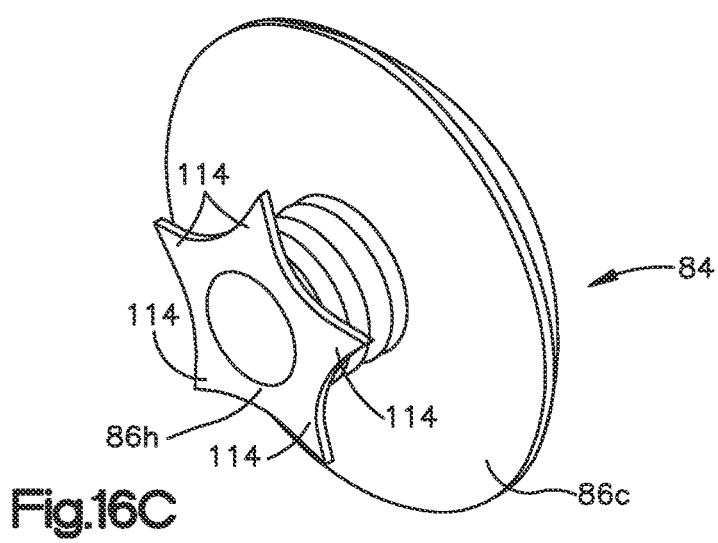
FIG. 16C is a perspective view of the expandable cranial fixation assembly illustrated in FIG. 16A.
Figure 16D:
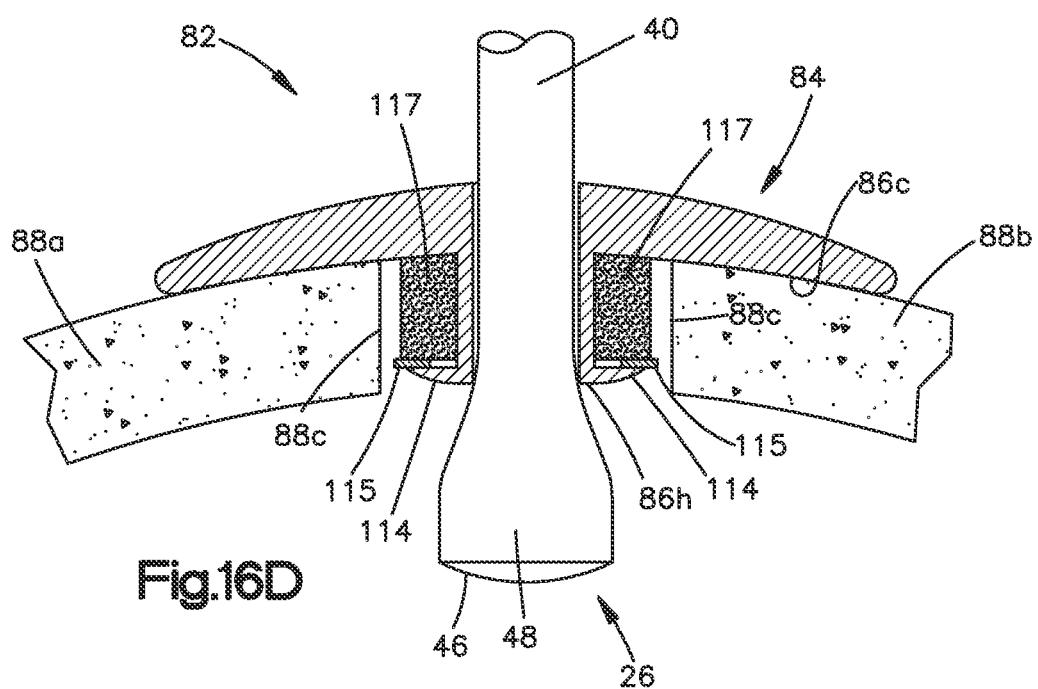
FIG. 16D is a sectional elevation view of the expandable cranial fixation assembly illustrated in FIG. 16A in accordance with an alternative embodiment, prior to expansion of the expandable cranial fixation member.
Figure 16E:
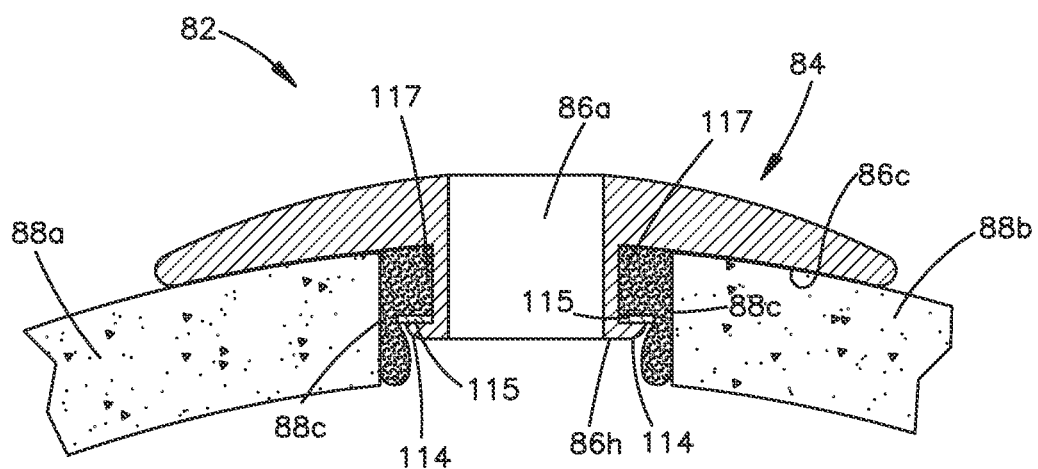
FIG. 16E is a sectional elevation view of the expandable cranial fixation assembly illustrated in FIG. 16D, after expansion of the expandable cranial fixation member.

In an alternative embodiment as depicted in FIGS. 16D-E, the cranial fixation assembly further includes an auxiliary fixation member, such as a spreading disc 115, the spreading disc 115 configured to be carried by the points 114. The spreading disc has an outer diameter that is smaller than the width of the gap between the bone segments 88a and 88b, and an inner diameter that is greater than the shaft 86d, such that the spreading disc 115 does not inhibit radial expansion of the shaft 86d as the mandrel 46 is pulled therethrough. The shaft 86d is of such a length that the spreading disc 115 can be carried around the shaft 86d by the points 114, while leaving a volume between the lower surface 86c of the cranial implant 84 and the spreading disc 115 that is filled with an deformable engagement material, such as a filler 117. The engagement material can act as an adhesive, or may otherwise provide added structural integrity to the expandable cranial fixation assembly. For example, the filler 117 may be made of an elastomeric material, an osteoinductive material, a combination thereof, or any other suitable material as desired. It should be appreciated that the lower disc 86h can be formed without the points 114, for example to augment the amount of available surface area of the lower disc 86h for engaging with the spreading disc 115.

During use, as the mandrel 46 enters the distal end 86f of the shaft 86d, the outer surface 48 of the mandrel 46 interferes with the inner surface of the shaft 86d, causing the shaft 86d to axially compress and/or expand radially outward as described above. Axial compression of the shaft 86d causes the spreading disc 115 to be drawn upward in the direction of the lower surface 86c of the cranial clamp 84, thereby compressing the filler 117 such that it expands radially outward between the cranial clamp 84 and the spreading disc 115, and engages the edges 88c of the bone segments 88a and 88b, thereby securing the cranial clamp 84 within the gap between the bone segments 88a and 88b. As the mandrel 46 advances further up the shaft 86d, the lower surface 86c of the cranial implant 84 is drawn against the outer surfaces of the bone segments 88a and 88b, thereby imparting a compressive, or clamping, force between the upper surfaces of the bone segments 88a and 88b engaged by the lower surface 86c of the cranial implant 84 and the filler 117 engaged along the edges 88c of the bone segments 88a and 88b.

Figure 16F:
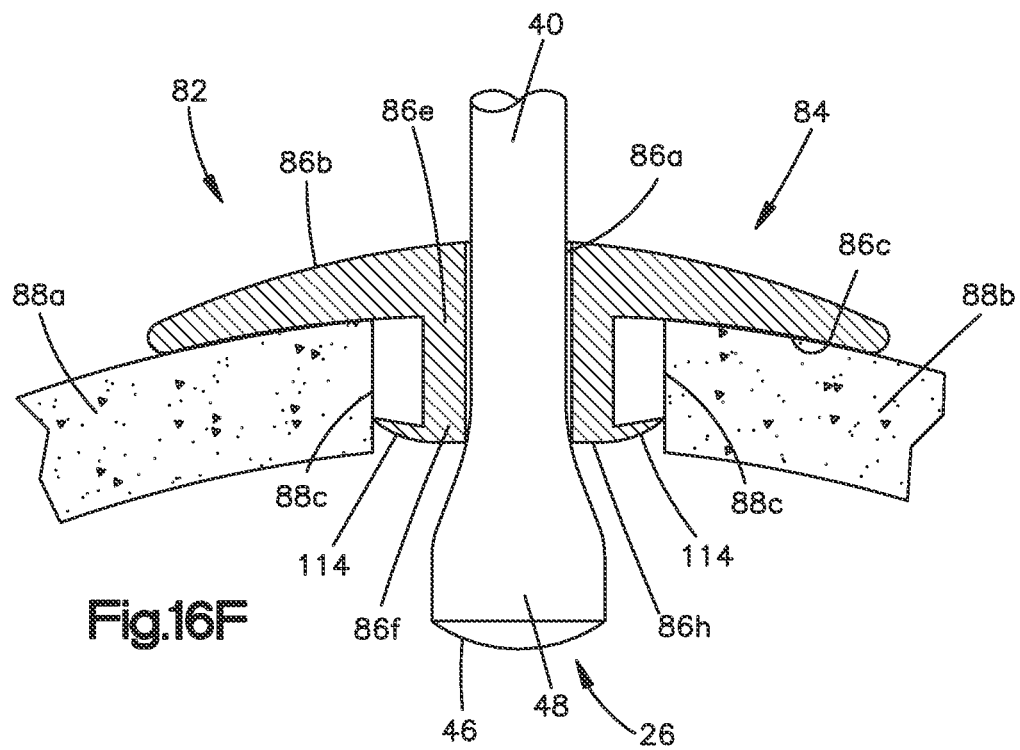
FIG. 16F is a sectional elevation view of the expandable cranial fixation assembly illustrated in FIG. 16A in accordance with an alternative embodiment, prior to expansion of the expandable cranial fixation member.
Figure 16G:
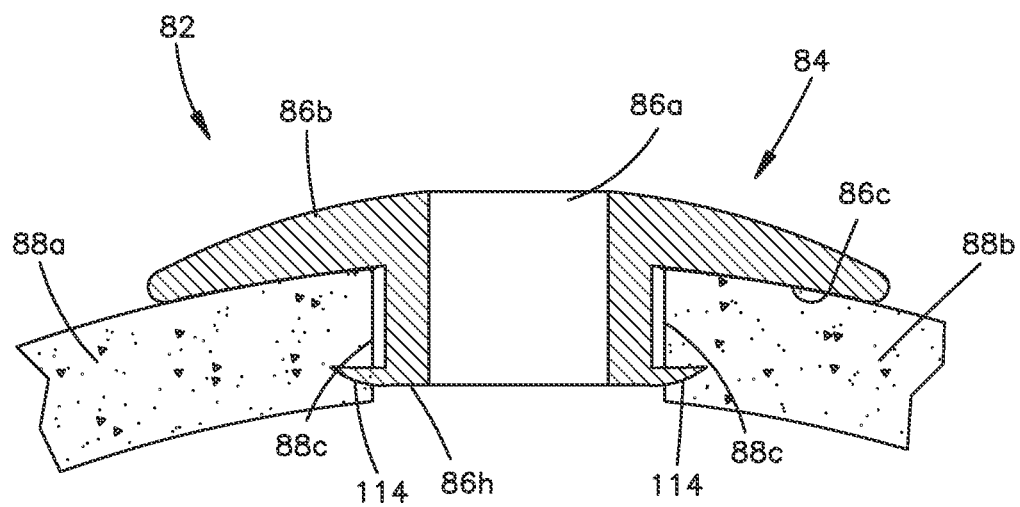
FIG. 16G is a sectional elevation view of the expandable cranial fixation assembly illustrated in FIG. 16F, after expansion of the expandable cranial fixation member.

In another alternative embodiment as depicted in FIGS. 16F-G, the shaft 86d is of a thickness such that axial compression during pull-though of the mandrel is minimized, and is of such a length that when the cranial clamp 84 is disposed within a surgical site, the points 114 define insertion trajectories into the edges 88c of the bone segments 88a and 88b. In this embodiment, as the mandrel 46 enters the distal end 86f of the shaft 86d, the outer surface 48 of the mandrel 46 interferes with the inner surface of the shaft 86d, causing the shaft 86d to expand radially outward as described above. Radial expansion of the shaft 86d causes the points 114 to cut into the edges 88c of the bone segments 88a and 88b, for example into cancellous bone, thereby securing the cranial clamp 84 within the gap between the bone segments 88a and 88b. As the mandrel 46 advances further up the shaft 86d, the lower surface 86c of the cranial implant 84 is drawn against the outer surfaces of the bone segments 88a and 88b, thereby imparting a compressive, or clamping, force between the upper surfaces of the bone segments 88a and 88b engaged by the lower surface 86c of the cranial implant 84 and the points 114 engaged in the edges 88c of the bone segments 88a and 88b. As the mandrel 46 is drawn through the shaft 86d, the shaft 86d undergoes radial expansion. It should be noted that the shaft 86d can be designed to limit or restrict the amount of axial compression towards the proximal end 86e, for example by tapering the thickness of the shaft 86d between the proximal and distal ends 86e and 86f, and the like.

Referring now to FIGS. 17A-G, the cranial fixation assembly 82 and the cranial clamp 84 are illustrated in accordance with yet another embodiment. In the illustrated embodiment, the shaft 86d defines an oblong radial cross section, and is circumferentially solid along its entire length between the proximal and distal ends 86e and 86f, respectively, of the body 86. The outer surface of the shaft 86d has bone engagement structures, such as raised ridges 118, formed thereon. Furthermore, the aperture 86a is extended as an axial bore through the entirety of the shaft 86d along a concentric longitudinal axis C that is offset from the central shaft axis S.

Figure 17C:
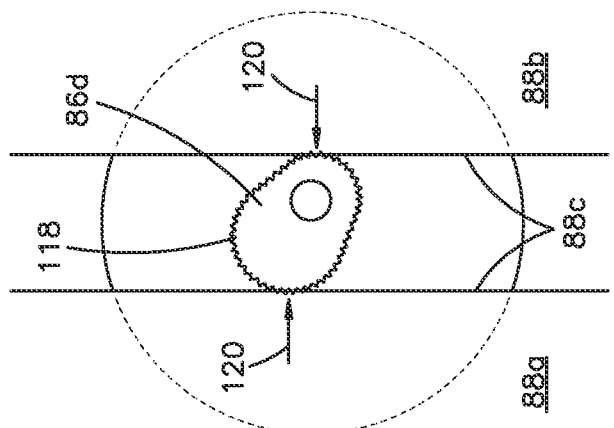
FIG. 17C is a bottom elevation view of the expandable cranial fixation assembly illustrated in FIG. 17B, with the expandable cranial fixation member rotated.
Figure 17B:
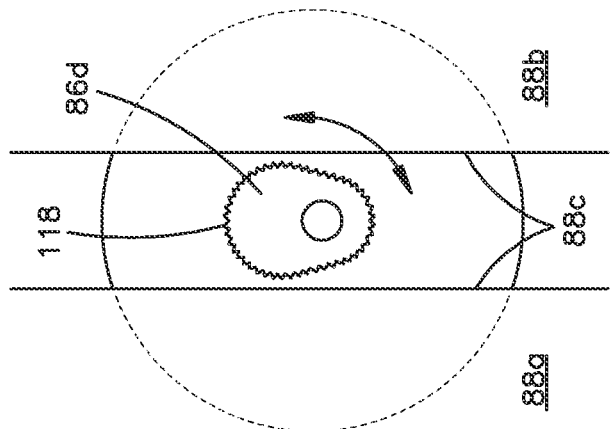
FIG. 17B is a bottom elevation view of the expandable cranial fixation assembly illustrated in FIG. 17A disposed between bone segments.
Figure 17A:
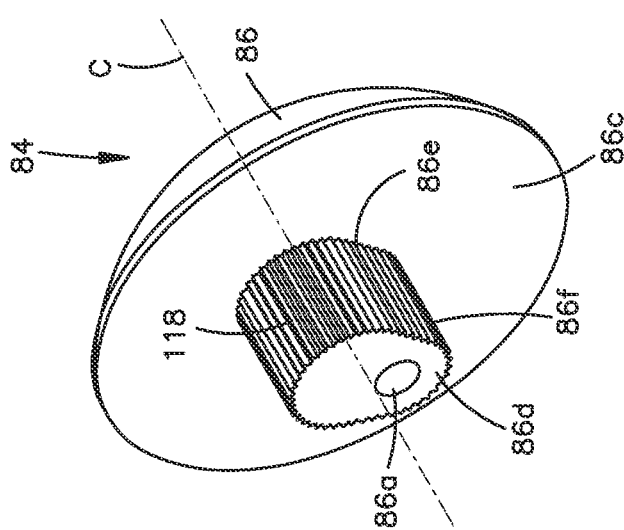
FIG. 17A is a perspective view of an expandable cranial fixation assembly in accordance with an alternative embodiment.

During use, the cranial fixation assembly 82 can be used to secure bone segments 88a and 88b. The oblong shape of the shaft 86d allows for the cranial clamp 84 to be optionally pre-fixed in a desired insertion position before the mandrel 46 is pulled through. This is accomplished by inserting the cranial fixation assembly 82 into a gap between bone segments 88a and 88b such that the narrow portion of the oblong shaft 86d is disposed in the gap between the bone segments 88a and 88b, as depicted in FIG. 17B. The cranial fixation assembly 82 can then be rotated in either a clockwise, or counter clockwise, direction, so that wider portion of the oblong shaft 86d, and the raised ribs 118 formed thereon, engages the edges 88c, for example at engagement points 120, of the bone segments 88a and 88b, as depicted in FIG. 17C. Of course the cranial fixation assembly 82 can be repositioned before the mandrel 46 is pulled through by counter-rotating the cranial implant 84 to disengage the raised ribs 118, positioning the cranial fixation assembly 82 in the new desired location, and pre-fixing it within the new location as described above.

Once the cranial fixation assembly 82 is disposed in the desired location, a downward, or caudal, biasing force is applied to the upper surface 86b of the cranial clamp 84, for example by an insertion instrument. An upward, or cranial, force is applied to the elongate shaft 40 of the expansion member 26, thereby drawing the mandrel 46 into the distal end 86f of the shaft 86d. In the embodiment depicted in FIGS. 17D-E, as the mandrel 46 enters the distal end 86f of the shaft 86d, the outer surface 48 of the mandrel 46 interferes with the inner surface of the shaft 86d, causing the shaft 86d to expand radially outward as described above. Radial expansion of the shaft 86d causes the outer surface of the shaft 86d and the raised ridges 118 to engage the edges 88c of the bone segments 88a and 88b, thereby inducing a friction fit of the cranial clamp 84 within the gap between the bone segments 88a and 88b.

In an alternative embodiment depicted in FIGS. 17F-G, the disc shaped portion of the body 86 is omitted, and the wall thickness of the shaft 86*d*, defined by the outer and inner diameters OD3 and ID4 of the shaft 86*d*, is thicker at the proximal and distal ends 86*e* and 86*f* of the shaft 86*d* than in the intermediate portion of the shaft 86*d* between the proximal and distal ends 86*e* and 86*f*. During use, the cranial clamp 84 is disposed within a gap between the bone segments 88*a* and 88*b*, and pre-fixed in position, as described above. As the mandrel 46 is drawn up and enters the distal end 86*f* of the shaft 86*d*, the outer surface 48 of the mandrel 46 interferes with the inner surface of the shaft 86*d*, causing the shaft 86*d* to expand radially outward as described above. Radial expansion of the shaft 86*d* causes the outer surface of the shaft 86*d* and the raised ridges 118 to engage the edges 88*c* of the bone segments 88*a* and 88*b*, thereby inducing a friction fit of the cranial clamp 84 within the gap between the bone segments 88*a* and 88*b*. Additionally, as the mandrel 46 is pulled through and radially expands the shaft 86*d*, the thicker portions of the shaft 86*d* at the proximal and distal ends 86*e* and 86*f* cause clamping tabs 122 to be formed on the upper and lower surfaces of the bone segments 88*a* and 88*b*. The clamping tabs 122 impart a compressive, or clamping, force onto the upper and lower surfaces of the bone segments 88*a* and 88*b* disposed between the clamping tabs 122.

Referring now to FIGS. 18A-L, the cranial fixation assembly 82 and the cranial clamp 84 are illustrated in accordance with still another embodiment. In the illustrated embodiment, the shaft 86*d* is circumferentially solid along its entire length between the proximal and distal ends 86*e* and 86*f*, respectively. The cranial fixation assembly 82 further includes an expandable auxiliary fixation member, such as the bottom disc 124. The bottom disc 124 includes a generally disc shaped body 126 with a convex upper surface 126*a*, and an opposing convex lower surface 126*b*. The concavity and convexity of the upper and lower surfaces 126*a* and 126*b*, respectively, can be configured to conform to a particular anatomical region, for example a particular area on the inner surface of the skull, so as to maximize contact between the upper surface 126*a* and underlying bone segments 88*a* and 88*b*, while simultaneously minimizing the profile of the lower surface 126*b* with respect to the inner surface of the bone segments 88*a* and 88*b*. It should be noted that any alternative body geometry and/or surface profile can be used for the auxiliary clamping member, examples of which are described in more detail below.

The body 126 of the bottom disc 124 further includes a ductile cannulated shaft 126*c* having a proximal end 126*d* and an opposing distal end 126*e*, the shaft 126*d* extending in an upward, or cranial, direction from the distal end 126*e* at the upper surface 126*a* along a central shaft axis S. The shaft 126*c* is configured to be received by the shaft 86*d* of the cranial clamp 84. Accordingly, the outer diameter OD4 of the shaft 126*c* is slightly smaller than the inner diameter ID4 of the shaft 86*d*. The shaft 126*c* further includes an axial bore 126*f* formed therethrough along the longitudinal shaft axis S. The thickness of the shaft 126*c* is defined by the difference between the outer diameter OD4 of the shaft and the inner diameter ID5 defined by the axial bore 126*f*. The inner diameter ID5 of the shaft 126*c* can be just slightly smaller than the outer dimension of the outer surface 48 of the mandrel 46. It should be appreciated that while the illustrated embodiments of the cranial fixation assemblies 82 are described and depicted in corresponding figures herein with the shaft 126*c* of the bottom disc 124 configured to be received within the shaft 86*d* of the cranial clamp 84, the components could be configured in a reverse fashion, such that the shaft 86*d* of the cranial clamp 84 is configured to be received within the shaft 126*c* of the bottom disc 124. In surgical applications, any variety of these configurations could be used as desired.

During use, the cranial fixation assembly 82 can be used to secure bone segments 88*a* and 88*b*. For example a plurality of bottom discs 124, with corresponding expansion members 26 disposed within the shafts 126*c* of the bottom discs, are disposed in desired locations around the perimeter of an opening within a patient's skull. Once the bottom discs 124 of the plurality of cranial fixation assemblies 82 are positioned, a corresponding bone flap can be disposed within the skull opening, such that the shafts 126*c* of the bottom discs 124 are disposed within the gap between the bone flap and the surrounding bone of the skull. A corresponding plurality of cranial clamps 84 can then be inserted onto respective expansion members and positioned such that the shafts 126*c* of the bottom discs 124 are disposed within the shafts 86*d* of the cranial clamps 84.

Once the plurality of cranial fixation assemblies are positioned as desired, and for each respective cranial fixation assembly 82, a downward, or caudal, biasing force is applied to the upper surface 86*b* of the cranial clamp 84, for example by an insertion instrument. An upward, or cranial, force is applied to the elongate shaft 40 of the expansion member 26, thereby drawing the mandrel 46 into the axial bore 126*f* at the distal end 126*e* of the shaft 126*c*. In the embodiment depicted in FIGS. 18B-C, as the mandrel 46 enters the distal end 126*e* of the shaft 126*c*, the outer surface 48 of the mandrel 46 interferes with the inner surface of the axial bore 126*f*, causing the shaft 126*c* to compress axially towards the proximal end 126*d* and/or to expand radially outward as described above. Axial compression of the shaft 126*c* causes the shaft 126*c* of the bottom disc 124 to enter the shaft 86*d* of the cranial clamp 84, and causes the upper surface 126*a* of the bottom disc 124 to be drawn upwards and to engage with the lower surfaces of the bone segments 88*a* and 88*b*, thereby drawing the lower surface 86*c* of the cranial implant 84 against the outer surfaces of the bone segments 88*a* and 88*b*, and imparting a compressive, or clamping, force onto the surfaces of the bone segments 88*a* and 88*b* disposed between the lower surface 86*c* of the cranial implant 84 and the upper surface 126*a* of the bottom disc 124. As the mandrel 46 advances within the shaft 126*c*, the shaft 126*c* radially expands and engages with the shaft 86*d* of the cranial clamp 84, which in turn causes the shaft 86*d* to expand radially, thereby causing the outer surface of the shaft 86*d* to engage the edges 88*c* of the bone segments 88*a* and 88*b*, thereby inducing a friction fit of the bottom disc 124 and the cranial clamp 84 within the gap between the bone segments 88*a* and 88*b* and fixing the bottom disc 124 and the cranial clamp 84 with respect to each other.

Figure 18D:
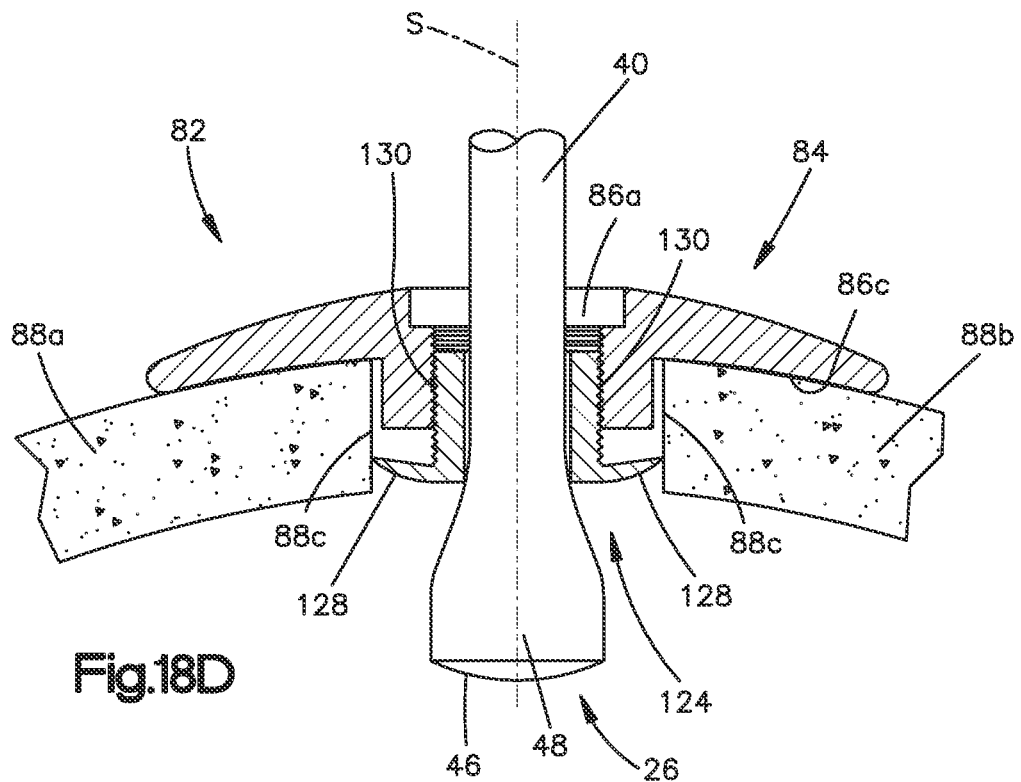
FIG. 18D is a sectional elevation view of the expandable cranial fixation assembly illustrated in FIG. 18A in accordance with an alternative embodiment, prior to expansion of the expandable cranial fixation member.
Figure 18E:
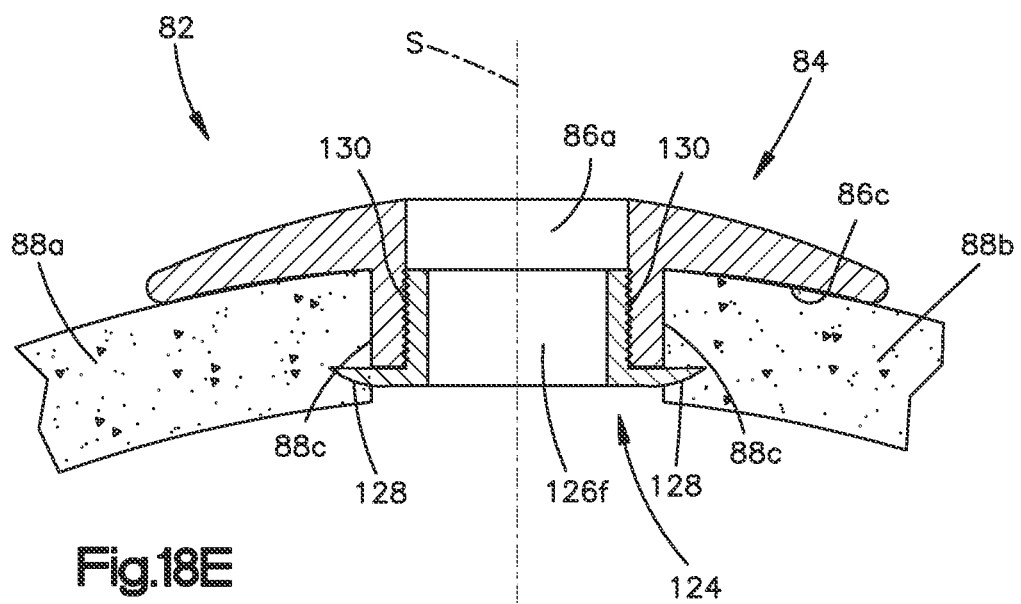
FIG. 18E is a sectional elevation view of the expandable cranial fixation assembly illustrated in FIG. 18D, after expansion of the expandable cranial fixation member.
Figure 18I:
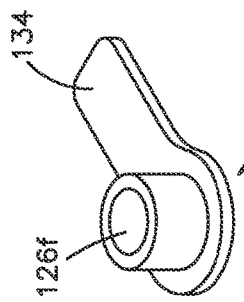
FIG. 18I is a perspective view of the expandable cranial fixation assembly component illustrated in FIG. 18F in accordance with another embodiment.
Figure 18J:
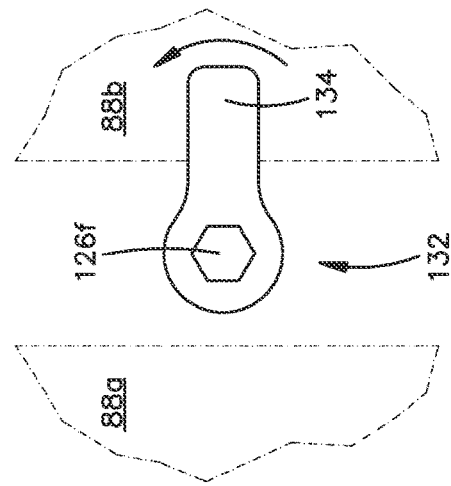
FIG. 18J is a bottom elevation view of the expandable cranial fixation assembly component illustrated in FIG. 18H disposed between bone segments.
Figure 18G:
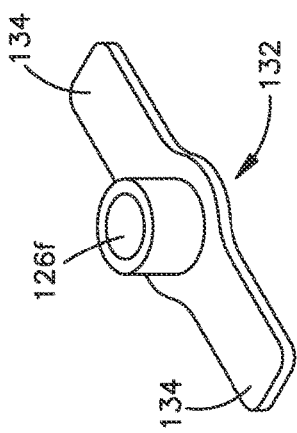
FIG. 18G is a perspective view of the expandable cranial fixation assembly component illustrated in FIG. 18F in accordance with another embodiment.
Figure 18H:
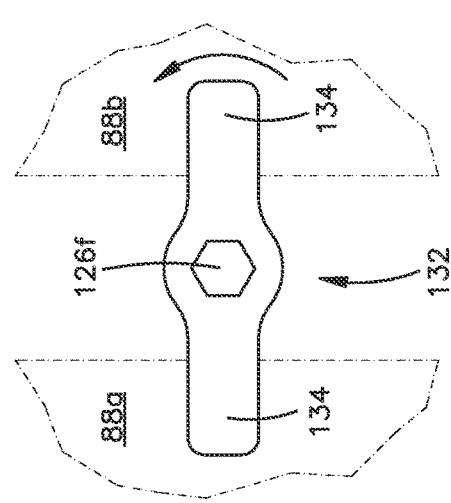
FIG. 18H is a bottom elevation view of the expandable cranial fixation assembly component illustrated in FIG. 18G disposed between bone segments.
Figure 18F:
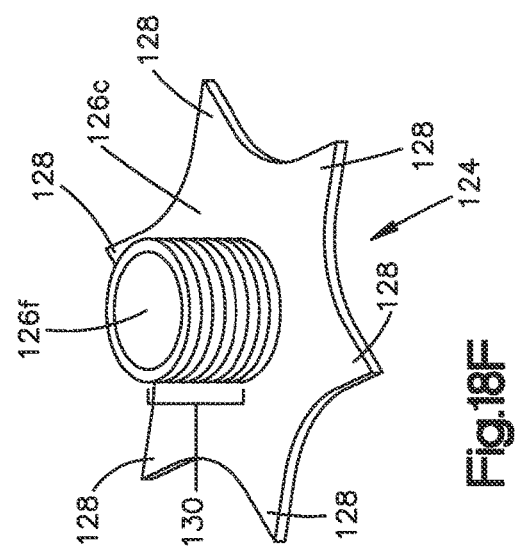
FIG. 18F is a perspective view of a component of the expandable cranial fixation assembly illustrated in FIG. 18D.

In an alternative embodiment as depicted in FIGS. 18D-F, the body 126 of the bottom disc 124 is configured with a plurality of bone engagement structures, such as points 128, that are formed within the disc shaped portion of the body 126, as illustrated in FIG. 18F. The points 128 are configured to cut into or otherwise engage with the bone segments 88*a* and 88*b*, as described in more detail below. In the illustrated embodiment, six points 128 are spaced apart equally around the circumference of the bottom disc 124, but more or less points 128 could be circumferentially arranged in any pattern on the bottom disc 124 as desired. The outer surface of the shaft 126*c* and the inner surface of the shaft 86*d* may have optional engagement structures, such as raised ridges 130, formed thereon, the raised ridges 130 configured to complimentarily engage each other as the shaft 126*c* of the bottom disc 124 enters the shaft 86*d* of the cranial clamp 84.

Of course other engagement structures, such as ratcheting teeth, or the like, could be used as desired. Use of the optional raised ridges 130 on the shafts 126c and 86d of the bottom disc 124 and/or the cranial clamp 84 allow those components to be manufactured in such a length that the cranial fixation system 82 can be utilized to secure bone segments of a variety of thicknesses. Additionally, the shaft 126c is of such a length that when the bottom disc 124 is disposed within the shaft 86d of the cranial clamp 84 within a surgical site, the points 128 define insertion trajectories into the edges 88c of the bone segments 88a and 88b.

In the embodiment depicted in FIGS. 18D-F, as the mandrel 46 enters the distal end 126e of the shaft 126c and, the outer surface 48 of the mandrel 46 interferes with the inner surface of the axial bore 126f, causing the shaft 126c to expand radially outward as described above. Radial expansion of the shaft 126c causes the points 128 to cut into the edges 88c of the bone segments 88a and 88b, thereby securing the bottom disc 124 within the gap between the bone segments 88a and 88b. As the mandrel 46 advances further up the shaft 126c, the lower surface 86c of the cranial implant 84 is drawn against the outer surfaces of the bone segments 88a and 88b, thereby imparting a compressive, or clamping, force between the upper surfaces of the bone segments 88a and 88b engaged by the lower surface 86c of the cranial implant 84 and the points 128 engaged in the edges 88c of the bone segments 88a and 88b.

Figure 18L:
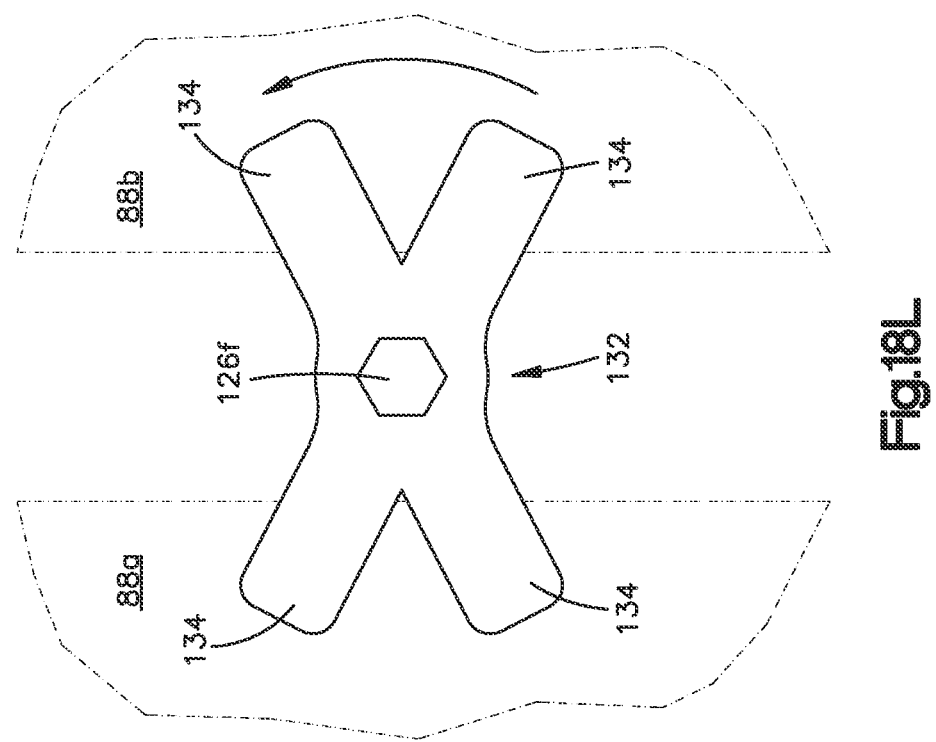
FIG. 18L is a bottom elevation view of the expandable cranial fixation assembly component illustrated in FIG. 18K disposed between bone segments.
Figure 18K:
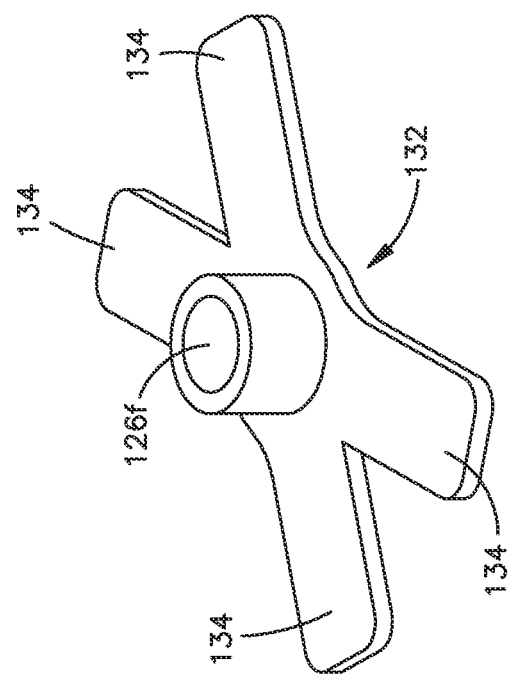
FIG. 18K is a perspective view of the expandable cranial fixation assembly component illustrated in FIG. 18F in accordance with another embodiment.

In another embodiment, alternative expandable auxiliary fixation members can be provided, for example the key lock bars 132, as illustrated in FIGS. 18G-L. The key lock bars 132 are constructed similarly to the bottom discs 124, with the disc shaped portion of the body 126 replaced by one or more wings 134. The wings are configured so as to allow the cranial fixation assembly to be distracted from a patient's skull, for example by inserting a distraction tool into the axial bore 126, and rotating the key lock bar 132 so that the blades 134 are oriented within the gap between the bone segments 88a and 88b, as illustrated in FIGS. 18H, 18J, and 18L. Thereafter, the cranial fixation assembly 82 can be easily removed from the skull. It should be appreciated that although the illustrated embodiments depict one, two, or four rectangular, planar blades 134, that any blade geometry and/or number of blades can be used as desired. During use, the key lock bars 132 can be secured to the bone segments 88a and/or 88b, so as to prevent rotation of the key lock bars 132 in situ, for example by the use of securing structures, for example retaining hooks passed through bores in the shaft 126c and/or the blades 134 and inserted into the bone segments 88a and/or 88b, retaining screws inserted through apertures in the blades 134 and into the bone segments 88a and/or 88b, or the like.

Referring now to FIGS. 19A-F, the cranial fixation assembly 82 and the cranial clamp 84 are illustrated in accordance with yet another embodiment. In the embodiment depicted in FIGS. 19A-C, an expandable engagement body, such as the generally rectangular expandable fixation block 136 extends from the lower surface 86c of the body 86 in place of the shaft 86d. It should be appreciated that the body of the fixation block 136 can take on any alternative geometry as desired. The thickness of the fixation block 136, as defined by the distance between opposing upper and lower ends 136a and 136b of the fixation block 136, can be defined to match the thickness of the bone segments 88a and 88b in a desired surgical insertion site. The fixation block 136 has a bore 136c, defined along the longitudinal shaft axis S, extending therethrough between opposing front and rear ends 136d and 136e, the longitudinal bore 136c having an inner diameter that is slightly smaller than the outer dimension of the outer surface 48 of the mandrel 46. It should be appreciated that the while a round bore 136c is depicted in the illustrated embodiment, that any other desired bore geometry can be used. The opposing sides 136f of the fixation block have bone engagement structures formed thereon, for example in the form of opposing rows of teeth 138, the teeth 138 configured to engage the bone segments 88a and 88b, for example by cutting into the edges 88c of the bone segments 88a and 88b.

During use, the cranial fixation assembly 82 can be used to secure bone segments 88a and 88b. Once a respective cranial fixation assembly 82 is disposed in a desired location, a downward, or caudal, biasing force is applied to the upper surface 86b of the cranial clamp 84, for example by an insertion instrument. A lateral force is applied to the elongate shaft 40 of the expansion member 26, thereby drawing the mandrel 46 into the bore 136c at the front end 136d of the fixation block 136. The lateral force can be applied, for example, by pulling a cable attached to the end of the elongate shaft 40 opposite the mandrel 46. As the mandrel 46 enters the bore 136c, the outer surface 48 of the mandrel 46 interferes with the inner surface of the bore 136c, causing widthwise expansion of the fixation block 136. As the fixation block 136 expands, the sides 136f of the fixation block engage the edges 88c of the bone segments 88a and 88b, causing the teeth 138 on the sides 136f of the fixation block 136 to engage with the edges 88c of the bone segments 88a and 88b, thereby inducing a friction fit of the cranial clamp 84 within the gap between the bone segments 88a and 88b, and anchoring the cranial clamp 84 within the gap between the bone segments 88a and 88b. As the teeth 138 cut into the edges 88c of the bone segments 88a and 88b, the lower surface 86c of the cranial implant 84 can be drawn against the outer surfaces of the bone segments 88a and 88b, thereby imparting a compressive, or clamping, force onto the surfaces of the bone segments 88a and 88b disposed between the lower surface 86c of the cranial implant 84 and the teeth 138.

Figure 19A:
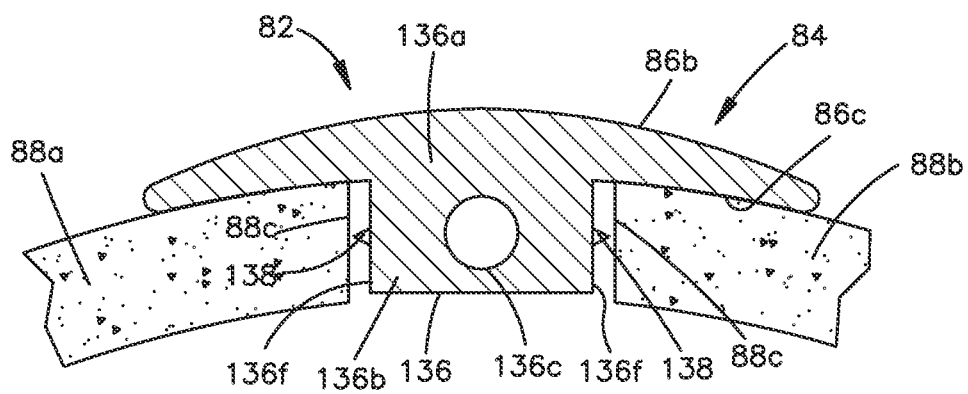
FIG. 19A is a sectional front elevation view of an expandable cranial fixation assembly in accordance with an alternative embodiment, prior to expansion of the expandable cranial fixation member.
Figure 19B:
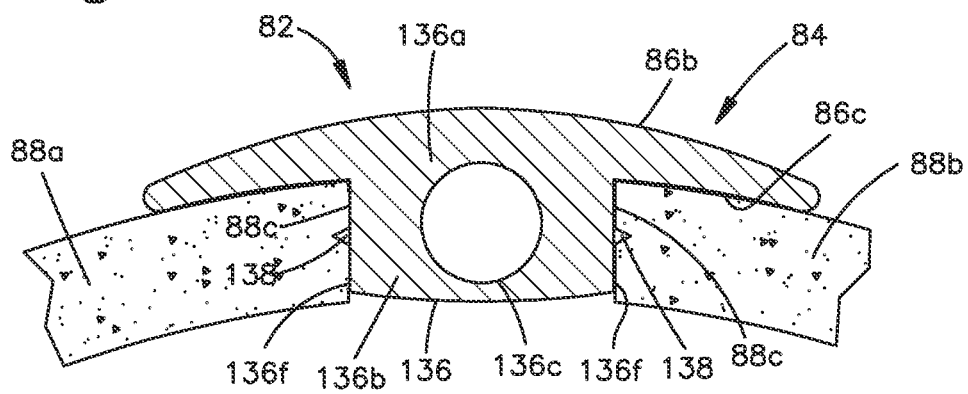
FIG. 19B is a sectional front elevation view of the expandable cranial fixation assembly illustrated in FIG. 19A, after expansion of the expandable cranial fixation member.
Figure 19C:
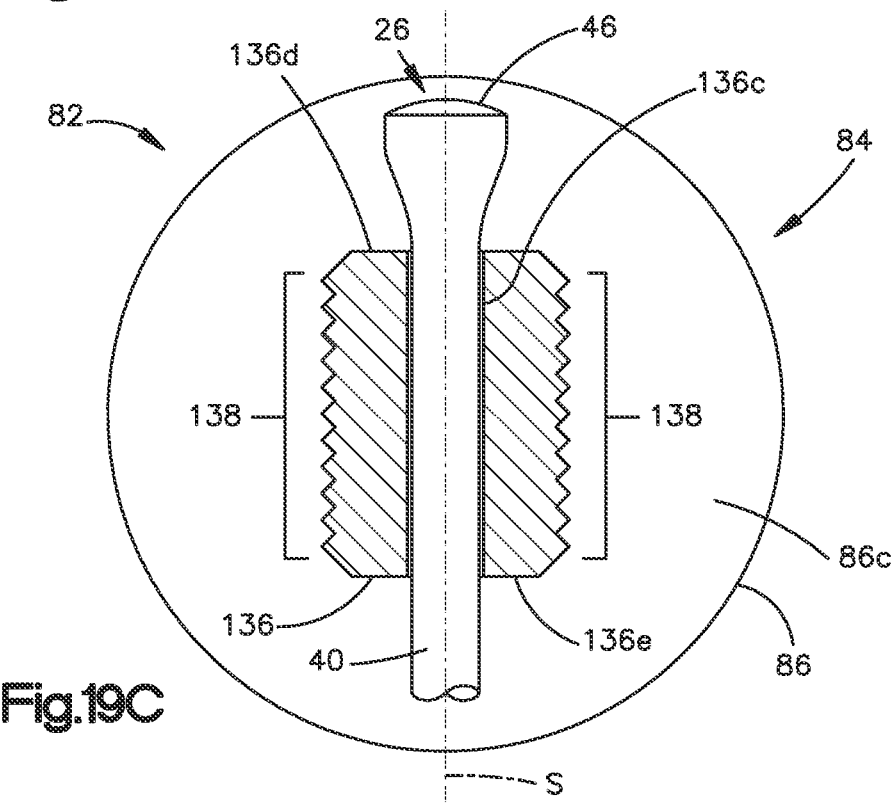
FIG. 19C is a sectional bottom elevation view of the expandable cranial fixation assembly illustrated in FIG. 19A, prior to expansion of the expandable cranial fixation member.
Figure 19D:
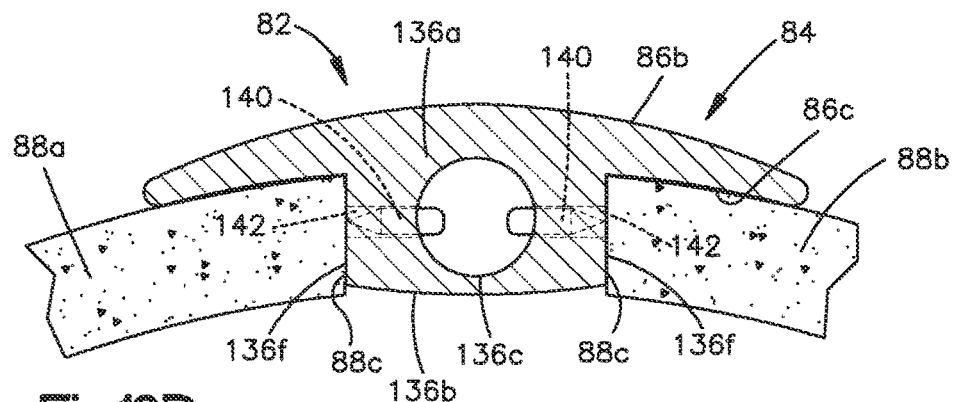
FIG. 19D is a sectional front elevation view of the expandable cranial fixation assembly illustrated in FIG. 19A in accordance with an alternative embodiment, prior to expansion of the expandable cranial fixation member.
Figure 19E:
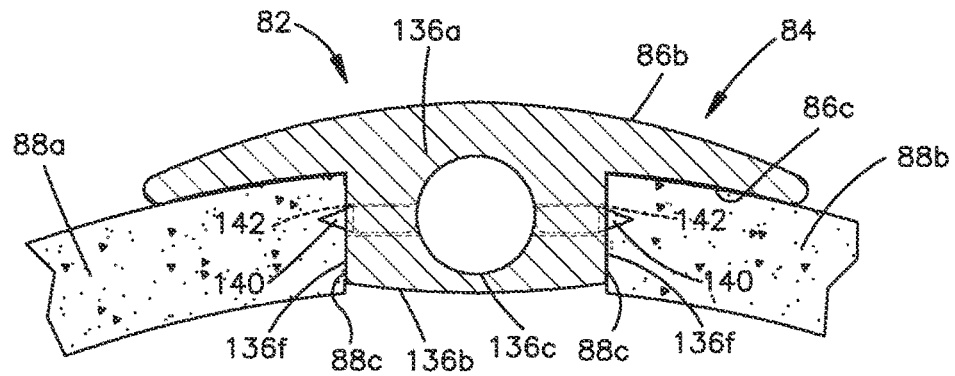
FIG. 19E is a sectional front elevation view of the expandable cranial fixation assembly illustrated in FIG. 19D, after expansion of the expandable cranial fixation member.
Figure 19F:
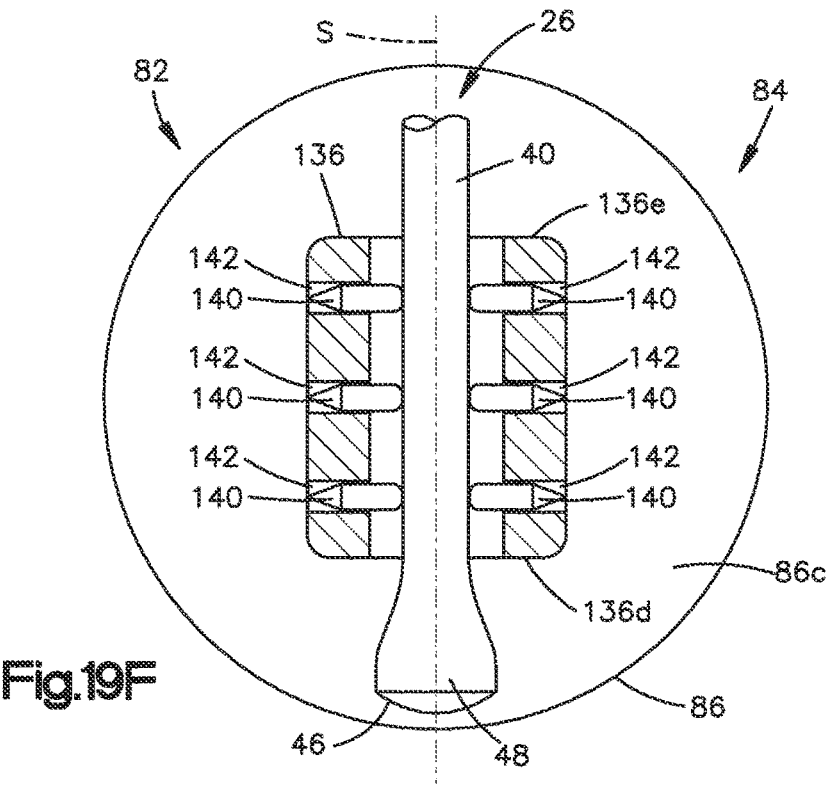
FIG. 19F is a sectional bottom elevation view of the expandable cranial fixation assembly illustrated in FIG. 19D, prior to expansion of the expandable cranial fixation member.

In an alternative embodiment depicted in FIGS. 19D-F, the rows of teeth 138 are replaced with alternative bone engagement structures, such as a plurality of spikes 140. The spikes 140 are carried in a respective plurality of cross bores 142 that intersect with the bore 136c and extend between the opposing sides 136f of the fixation block 136. The spikes 140 are disposed within the cross bores 142 such that the dull ends of the spikes protrude into the bore 136c, with the pointed ends of the spikes 140 facing the sides 136f of the fixation block 136. During use, as the mandrel 46 advances through the bore 136c, the outer surface 48 of the mandrel 46 interferes with the dull ends of the spikes 140, thereby causing spikes 140 to translate outwardly within the cross bores 142, such that the pointed ends of the spikes 140 protrude from the cross bores 142 on the sides 136f of the fixation block, and cut into the edges 88c of the bone segments 88a and 88b, thereby anchoring the cranial clamp 84 within the gap between the bone segments 88a and 88b. As the spikes 140 cut into the edges 88c of the bone segments 88a and 88b, the lower surface 86c of the cranial implant 84 can be drawn against the outer surfaces of the bone segments 88a and 88b, thereby imparting a compressive, or clamping, force onto the surfaces of the bone segments 88a and 88b disposed between the lower surface 86c of the cranial implant 84 and the spikes 140.

Referring now to FIGS. 20A-B, the cranial fixation assembly 82 and the cranial clamp 84 are illustrated in accordance with still another embodiment. In the illustrated embodiment, the cranial clamp 84 includes an expandable engagement body comprised of ductile upper and lower fixation members 144 and 146, each of the upper and lower fixation members 144 and 146 having opposing proximal and distal ends 144a and 144b, and 146a and 146b, respectively. The fixation members 144 and 146 of the illustrated embodiment have annular bodies, but any other suitable body geometry could be used as desired. The lower fixation member 146 is configured to be received within the upper fixation member 144. In the illustrated embodiment, the upper and lower fixation members 144 and 146 have cylindrically shaped bodies, but any other suitable body geometry could be used as desired. The outer surface of the lower fixation member 146 can have optional engagement structures configured to engage the inner surface of the upper fixation member 144 formed thereon, for example raised ridges 148. The inner surface of the upper fixation member 144 can have optional complimentary raised ridges 148 formed therein. The inner diameter of the lower fixation member 146 is slightly smaller than the outer dimension of the outer surface 48 of the mandrel 46.

The lower fixation member 146 may have a greater length as defined between its proximal and distal ends 146a and 146b, than the length of the upper fixation member 144 as defined between its proximal and distal ends 144a and 144b. The upper and lower fixation members 144 and 146 can be manufactured in varying lengths, for example based on the width of the gap between the bone segments 88a and 88b in which the cranial clamp 84 will be disposed. The proximal end 144a of the upper fixation member 144 is connected to the distal end 146b of the lower fixation member 146 by one or more flexible curved arms 150. The outer surfaces of the curved arms 150 have bone engagement structures formed thereon, for example teeth 152. In a pre-installed configuration, the proximal end 146a of the lower fixation member 146 can be engaged within the distal end 144b of the upper fixation member 144. It should be appreciated that while the cranial clamp 84 is illustrated as having two flexible arms 150, any number of flexible arms 150 could be used as desired, or alternatively, one continuous flexible arm 150 could be formed around the entire perimeter of the upper and lower fixation members 144 and 146.

During use, the cranial fixation assembly 82 can be used to secure bone segments 88a and 88b. Once a respective cranial fixation assembly 82 is disposed in a desired location, a downward, or caudal, biasing force is applied against the proximal end 144a of the upper fixation member 144, for example by an insertion instrument. An upward, or cranial, force is applied to the elongate shaft 40 of the expansion member 26, thereby drawing the mandrel 46 into the distal end 146b of the lower fixation member 146. As the mandrel 46 advances upwardly within the lower fixation member 146, the upper and lower fixation members 144 and 146 are drawn together, thereby causing the flexible arms 150 to collapse outwardly towards each other such that the teeth 152 engage the bone segments 88a and 88b, thereby anchoring the cranial clamp 84 within the gap between the bone segments 88a and 88b. As the mandrel 46 advances through the lower fixation member 146, the lower fixation member 146 may expand in a radial direction, causing the optional raised ridges 148 on the outer surface of the lower fixation member 146 to engage with the inner surface of the upper fixation member 144, thereby activating the cranial fixation assembly 82 into a locked configuration.

Figure 21A:
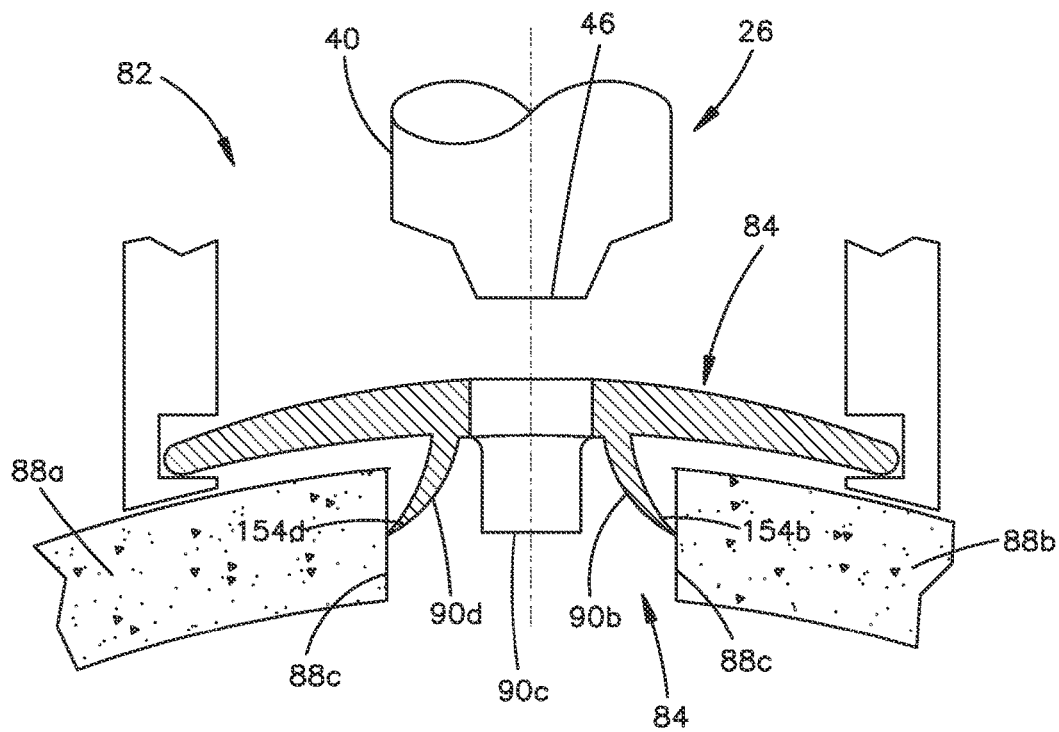
FIG. 21A is a sectional elevation view of an expandable cranial fixation assembly in accordance with an alternative embodiment, prior to expansion of the expandable cranial fixation member.
Figure 21B:
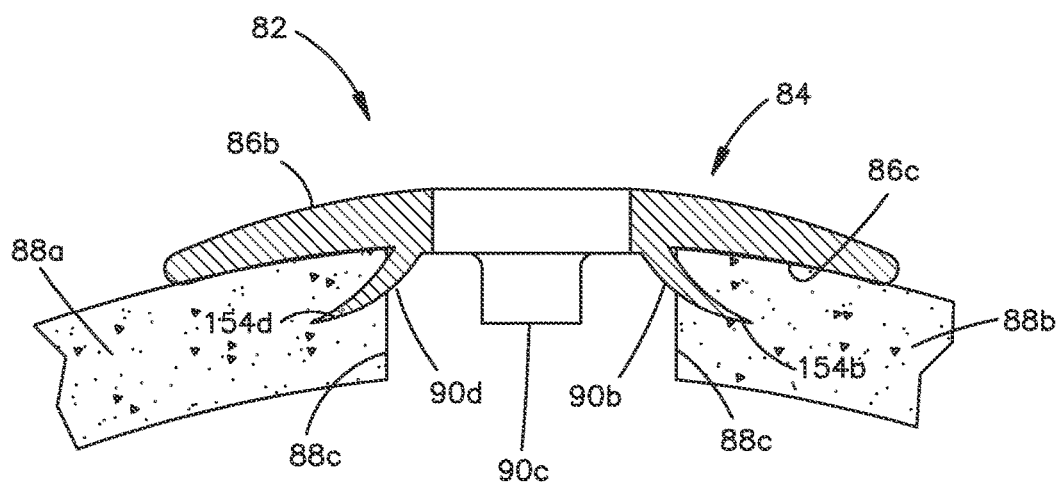
FIG. 21B is a sectional elevation view of the expandable cranial fixation assembly illustrated in FIG. 21A, after expansion of the expandable cranial fixation member.

Referring now to FIGS. 21A-B, the cranial fixation assembly 82 and the cranial clamp 84 are illustrated in accordance with still another embodiment. In the illustrated embodiment, the mandrel 46 is pushed into, rather than pulled through, the shaft 86d. Additionally, the legs 90a-d have bone engagement structures formed at the distal ends thereof, for example cutting tips 154a-d. The legs 90a-d are of such a length that when the cranial clamp 84 is disposed within a surgical site, the distal ends of the legs, and consequently the cutting tips 154a-d define insertion trajectories into the edges 88c of the bone segments 88a and 88b.

During use, the cranial fixation assembly 82 can be used to secure bone segments 88a and 88b. Once a respective cranial fixation assembly 82 is disposed in a desired location, the cranial clamp 84 is held in position, for example by an insertion instrument. A downward, or caudal, force is applied to the elongate shaft 40 of the expansion member 26, thereby causing the mandrel 46 to enter the proximal end 86e of the shaft 86d. As the mandrel 46 enters the shaft 86d, the outer surface 48 of the mandrel 46 interferes with the inner surface of the shaft 86d, causing the shaft 86d to expand radially outward as described above. Radial expansion of the shaft 86d causes the legs 90a-d to deflect outwardly, in turn causing the cutting tips 154b and 154d of the legs 90b and 90d to cut into the edges 88c of the bone segments 88a and 88b, thereby securing the cranial clamp 84 within the gap between the bone segments 88a and 88b. As the cutting tips 154b and 154d of the legs 90b and 90d cut into the bone segments 88a and 88b, the lower surface 86c of the cranial implant 84 is drawn against the outer surfaces of the bone segments 88a and 88b, thereby imparting a compressive, or clamping, force between the upper surfaces of the bone segments 88a and 88b engaged by the lower surface 86c of the cranial implant 84 and the legs 90b and 90d engaging the edges 88c of the bone segments 88a and 88b via the cutting tips 154b and 154d. It should be appreciated that while the illustrated embodiment depicts only the cutting tips 154b and 154d engaging the bone segments 88a and 88b, the legs 90a-d can be so configured, and the cranial fixation assembly 82 can be so oriented during insertion, that any combination of one or more, including all, of the cutting tips 154a-d cut into the bone segments 88a and 88b as the mandrel 46 advances downwardly into the shaft 86d.

It should be appreciated that a variety of kits can be provided that include one or more components of the expandable fixation assemblies 20, the expandable cranial fixation assemblies 82, and/or the expandable intervertebral implant assemblies 157. The components of the kits may be configured the same or differently. For example, within a single anchor kit, varying numbers of expandable fixation members 24 having variable shaft widths, lengths, and anchoring region profiles may be provided along with expansion members 26 having varying mandrels 46, and so on, depending for example on the type of procedure being performed by a surgeon, or on the particular anatomies of individual patients. In another example, a cranial fixation kit can be provided with a plurality of expandable cranial clamps 84 in accordance with the various embodiments described herein. Furthermore, the kits may also be configured differently with respect to which components of the individual systems are included in the kits. For example, a kit of expandable fixation assemblies 20 intended for fracture reduction may include one or more fixation members with offset shaft axes in addition to fixation members 24 with central shaft axes. Some of the fixation members 24 may have locking features formed on the heads 32 thereof, and the kit may also include one or more bone plates 62 intended for the particular type of fracture reduction procedure. In another example, one or more expandable intervertebral implant assemblies 157, configured the same or differently, can be provided in a spinal fixation kit along with one or more fixation members 24, one or more traditional pedicle screws, fixation rods, and the like.

Although the expandable fixation members and the other components of the expandable fixation assembly 20, the expandable cranial fixation assembly 82, and the expandable intervertebral implant assembly 157 have been described herein with reference to preferred embodiments and/or preferred methods, it should be understood that the words which have been used herein are words of description and illustration, rather than words of limitation. For example, it should be appreciated that the structures and/or features of components of the expandable fixation assembly 20 may be combined with or otherwise integrated with the structures and/or features of the expandable intervertebral implant assembly 157, and so on, unless otherwise indicated. Furthermore, it should be noted that although the expandable fixation assembly 20, the expandable cranial fixation assembly 82, and the expandable intervertebral implant assembly 157 have been described herein with reference to particular structure, methods, and/or embodiments, the scope of the instant disclosure is not intended to be limited to those particulars, but rather is meant to extend to all structures, methods, and/or uses of the expandable fixation assembly 20, the expandable cranial fixation assembly 82, and the expandable intervertebral implant assembly 157. Those skilled in the relevant art, having the benefit of the teachings of this specification, may effect numerous modifications to the expandable fixation assembly 20, the expandable cranial fixation assembly 82, and the expandable intervertebral implant assembly 157 as described herein, and changes may be made without departing from the scope and spirit of the instant disclosure, for instance as recited in the appended claims.

What is claimed:

1. An expandable intervertebral implant assembly configured to be implanted into an intervertebral space between first and second vertebrae that are spaced from one another along a first direction, the assembly comprising:
    an intervertebral implant comprising an implant body having upper and lower surfaces configured to face the first and second vertebrae, respectively, the upper and lower surfaces spaced from one another along the first direction such that at least a portion of the implant body is solid from the upper surface to the lower surface, the implant body further having first and second ends that are spaced from one another along a second direction, perpendicular to the first direction, the implant body defining at least a first bore that extends into the first end towards the second end along a bore axis that extends along the second direction; and
    a first expansion member,
    wherein the assembly is configured such that, when the first expansion member is biased through the first bore along the bore axis in the second direction, the first expansion member causes the expandable intervertebral implant assembly to expand along the first direction and engage with the first and second vertebrae, and the assembly is configured such that the expandable intervertebral implant assembly remains expanded after the first expansion member is removed from the first bore.

2. The expandable intervertebral implant assembly of claim 1, wherein at least one of the upper and lower surfaces of the implant body has one or more bone engagement structures formed thereon.

3. The expandable intervertebral implant assembly of claim 2, wherein the bone engagement structures include teeth.

4. The expandable intervertebral implant assembly of claim 1, wherein the assembly comprises at least a first expandable fixation assembly disposed within the first bore, wherein the first expandable fixation assembly includes the first expansion member.

5. The expandable intervertebral implant assembly of claim 1, wherein the implant body further includes at least a first slot formed therethrough, the first slot intersecting with the first bore, and
    wherein the expandable intervertebral implant assembly further includes at least a first pair of engagement structures, the first pair of engagement structures disposed within the first slot on opposite sides of the first expansion member.

6. The expandable intervertebral implant assembly of claim 5, wherein:
    the first pair of engagement structures includes first and second engagement structures that define upper and lower bone engagement surfaces, respectively; and
    when the first expansion member is biased through the internal bore, the first expansion member causes at least one of the first and second engagement structures to move away from the other of the at least one of the first and second engagement structures.

7. The expandable intervertebral implant assembly of claim 6, wherein the upper and lower bone engagement surfaces have bone engagement structures formed thereon.

8. The expandable intervertebral implant assembly of claim 7, wherein the bone engagement structures are teeth.

9. The expandable intervertebral implant assembly of claim 4, wherein the first expandable fixation assembly further includes a first fixation member that defines an axial bore, and the first expansion member is disposed within the axial bore of the first fixation member.

10. The expandable intervertebral implant assembly of claim 1, wherein, the assembly is configured such that, when the first expansion member is biased through the first bore, the first expansion member causes at least one of the upper and lower surfaces of the implant body to move away from the other of the at least one of the upper and lower surfaces of the implant body.

11. The expandable intervertebral implant assembly of claim 1, wherein the first expansion member comprises an elongate shaft having a proximal end and an opposing distal end, and further comprises a mandrel that extends from the distal end.

12. The expandable intervertebral implant assembly of claim 11, wherein the elongate shaft has a maximum cross-sectional dimension in a select direction that is perpendicular to an axis of the elongate shaft, and the mandrel has a maximum cross-sectional dimension in the select direction that is greater than the maximum cross-sectional dimension of the elongate shaft.

13. The expandable intervertebral implant assembly of claim 1, wherein:
    the implant body defines a second bore that extends into the first end towards the second end along a second bore axis; and
    the assembly further comprises a second expansion member,
    wherein the assembly is configured such that, when the second expansion member is biased through the second bore along the second bore axis, the second expansion member causes the expandable intervertebral implant assembly to expand along the first direction and engage with the first and second vertebrae.

14. The expandable intervertebral implant assembly of claim 13, wherein the second bore is spaced from the first bore along a third direction, perpendicular to both the first and second directions.

15. The expandable intervertebral implant assembly of claim 13, wherein the second bore is spaced from the first bore along the first direction.

16. An expandable intervertebral implant assembly configured to be implanted into an intervertebral space between first and second vertebrae that are spaced from one another along a first direction, the assembly comprising:
   an intervertebral implant comprising an implant body having upper and lower surfaces configured to face the first and second vertebrae, respectively, the upper and lower surfaces spaced from one another along the first direction such that at least a portion of the implant body is solid from the upper surface to the lower surface, the implant body further having first and second ends that are spaced from one another along a second direction, perpendicular to the first direction, the implant body defining at least a first bore that extends into the first end towards the second end along a bore axis; and
   at least a first expandable fixation assembly disposed within the first bore, wherein the first expandable fixation assembly includes a first expansion member and includes a first fixation member that defines an axial bore, the first expansion member being disposed within the axial bore of the first fixation member, wherein:
   the axial bore of the first fixation member has an inner dimension, and the first expansion member has an outer dimension that is greater than the inner dimension such that, when the first expansion member is biased through the axial bore of the first fixation member, the first expansion member causes the first fixation member to expand; and
   the assembly is configured such that, when the first expansion member is biased through the first bore along the bore axis, the first expansion member causes the expandable intervertebral implant assembly to expand along the first direction and engage with the first and second vertebrae.

17. The expandable intervertebral implant assembly of claim 16, wherein expansion of the first expansion member causes the expandable intervertebral implant assembly to expand.

18. The expandable intervertebral implant assembly of claim 16, wherein:
   the implant body further includes a first slot formed therethrough, the first slot intersecting with the first bore;
   the expandable intervertebral implant assembly further includes first and second engagement structures disposed within the first slot on opposite sides of the first expansion member; and
   when the first expansion member is biased through the axial bore of the first fixation member, expansion of the first expansion member causes at least one of the first and second engagement structures to move away from the other of the at least one of the first and second engagement structures.

19. The expandable intervertebral implant assembly of claim 16, wherein expansion of the first expansion member causes at least one of the upper and lower surfaces of the implant body to move away from the other of the at least one of the upper and lower surfaces of the implant body.

* * * * *